(12) United States Patent
Schultz et al.

(10) Patent No.: US 12,370,085 B2
(45) Date of Patent: Jul. 29, 2025

(54) SHUNTING SYSTEMS WITH ROTATION-BASED FLOW CONTROL ASSEMBLIES, AND ASSOCIATED SYSTEMS AND METHODS

(71) Applicant: Shifamed Holdings, LLC, Campbell, CA (US)

(72) Inventors: Eric Schultz, Los Altos, CA (US); Robert Chang, Belmont, CA (US); Tom Saul, Moss Beach, CA (US); Richard Lilly, San Jose, CA (US); Michael Drews, Palo Alto, CA (US); Claudio Argento, Felton, CA (US); Katherine Sapozhnikov, Campbell, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 742 days.

(21) Appl. No.: 17/684,544

(22) Filed: Mar. 2, 2022

(65) Prior Publication Data
US 2022/0387216 A1    Dec. 8, 2022

Related U.S. Application Data

(63) Continuation of application No. 17/175,332, filed on Feb. 12, 2021, now Pat. No. 11,291,585.
(Continued)

(51) Int. Cl.
*A61F 9/007*    (2006.01)

(52) U.S. Cl.
CPC .. *A61F 9/00781* (2013.01); *A61F 2210/0014* (2013.01)

(58) Field of Classification Search
CPC ............... A61M 27/002; A61F 9/00781
See application file for complete search history.

(56) References Cited

U.S. PATENT DOCUMENTS

| 4,401,107 A | 8/1983 | Harber et al. |
| 4,402,681 A | 9/1983 | Haas et al. |

(Continued)

FOREIGN PATENT DOCUMENTS

| AU | 2014200171 | 1/2014 |
| AU | 2014201621 B2 | 3/2016 |
| AU | 2016201445 B2 | 3/2016 |
| AU | 2018200325 A1 | 2/2018 |
| AU | 2017274654 | 12/2018 |
| AU | 2020201818 | 4/2020 |
| AU | 2017439185 | 5/2020 |

OTHER PUBLICATIONS

International Search Report and Written Opinion received for PCT Application No. PCT/US23/80290, filed on Nov. 17, 2023, Applicant: Shifamed Holdings, LLC, Date of Mailing: May 15, 2024, 12 pages.
(Continued)

*Primary Examiner* — Leslie R Deak
(74) *Attorney, Agent, or Firm* — Perkins Coie LLP

(57) ABSTRACT

The present technology relates to intraocular shunting systems and methods. In some embodiments, the present technology includes intraocular shunting systems that include a drainage element having an inflow portion configured for placement within an anterior chamber of the eye outside of an optical field of view of the patient and an outflow portion configured for placement at a different location of the eye. The system can also include a flow control assembly having a rotational control element operably coupled to the drainage element. The flow control assembly can further include an actuation structure coupled to the rotational control element and configured to selectively change an orientation of the rotational control element. An amount of fluid through the inflow portion and/or the outflow portion can vary based on the selected orientation of the rotational control element.

8 Claims, 26 Drawing Sheets

Related U.S. Application Data

(60) Provisional application No. 63/140,543, filed on Jan. 22, 2021, provisional application No. 63/116,674, filed on Nov. 20, 2020, provisional application No. 62/981,411, filed on Feb. 25, 2020, provisional application No. 62/976,890, filed on Feb. 14, 2020.

(56) References Cited

U.S. PATENT DOCUMENTS

| | | | |
|---|---|---|---|
| 4,595,390 A * | 6/1986 | Hakim | A61F 2/0036 604/9 |
| 5,070,697 A | 12/1991 | Van Zeggeren | |
| 5,123,906 A | 6/1992 | Kelman | |
| 5,476,445 A | 12/1995 | Baerveldt et al. | |
| 5,601,094 A | 2/1997 | Reiss | |
| 5,792,118 A | 8/1998 | Kurth et al. | |
| 6,077,298 A | 6/2000 | Tu et al. | |
| 6,077,299 A | 6/2000 | Adelberg et al. | |
| 6,203,513 B1 | 3/2001 | Yaron et al. | |
| 6,261,256 B1 | 7/2001 | Ahmed | |
| 6,450,984 B1 | 9/2002 | Lynch et al. | |
| 6,508,779 B1 | 1/2003 | Suson | |
| 6,589,203 B1 | 7/2003 | Mitrev | |
| 6,626,858 B2 | 9/2003 | Lynch et al. | |
| 6,638,239 B1 | 10/2003 | Bergheim et al. | |
| 6,666,841 B2 | 12/2003 | Gharib et al. | |
| 6,736,791 B1 | 5/2004 | Tu et al. | |
| 6,789,447 B1 | 9/2004 | Zinck | |
| 7,025,740 B2 | 4/2006 | Ahmed | |
| 7,207,965 B2 | 4/2007 | Simon | |
| 7,354,416 B2 | 4/2008 | Quiroz-Mereado et al. | |
| 7,458,953 B2 | 12/2008 | Peyman | |
| 7,699,882 B2 | 4/2010 | Stamper et al. | |
| 7,717,872 B2 | 5/2010 | Shetty | |
| 7,947,008 B2 | 5/2011 | Grahn et al. | |
| 8,012,134 B2 | 9/2011 | Claude et al. | |
| 8,206,333 B2 | 6/2012 | Schmidt et al. | |
| 8,206,440 B2 | 6/2012 | Guarnieri | |
| 8,298,240 B2 | 10/2012 | Giger et al. | |
| 8,308,701 B2 | 11/2012 | Horvath et al. | |
| 8,414,635 B2 | 4/2013 | Hyodoh et al. | |
| 8,506,515 B2 | 8/2013 | Burns et al. | |
| 8,540,659 B2 | 9/2013 | Berlin | |
| 8,579,848 B2 | 11/2013 | Field et al. | |
| 8,585,629 B2 | 11/2013 | Grabner et al. | |
| 8,663,303 B2 | 3/2014 | Horvath et al. | |
| 8,702,639 B2 | 4/2014 | Van Der Mooren et al. | |
| 8,721,702 B2 | 5/2014 | Romoda et al. | |
| 8,753,305 B2 | 6/2014 | Field et al. | |
| 8,758,290 B2 | 6/2014 | Horvath et al. | |
| 8,765,210 B2 | 7/2014 | Romoda et al. | |
| 8,771,220 B2 | 7/2014 | Nissan et al. | |
| 8,801,766 B2 | 8/2014 | Reitsamer et al. | |
| 8,828,070 B2 | 9/2014 | Romoda et al. | |
| 8,852,136 B2 | 10/2014 | Horvath et al. | |
| 8,852,137 B2 | 10/2014 | Horvath et al. | |
| 8,852,256 B2 | 10/2014 | Horvath et al. | |
| 8,882,781 B2 | 11/2014 | Smedley et al. | |
| 8,915,877 B2 | 12/2014 | Cunningham et al. | |
| 8,932,247 B2 | 1/2015 | Stergiopulos | |
| 8,974,511 B2 | 3/2015 | Horvath et al. | |
| 9,017,276 B2 | 4/2015 | Horvath et al. | |
| 9,095,411 B2 | 8/2015 | Horvath et al. | |
| 9,095,413 B2 | 8/2015 | Romoda et al. | |
| 9,113,994 B2 | 8/2015 | Horvath et al. | |
| 9,125,723 B2 | 9/2015 | Horvath et al. | |
| 9,192,516 B2 | 11/2015 | Horvath et al. | |
| 9,226,851 B2 | 1/2016 | Gunn | |
| 9,271,869 B2 | 3/2016 | Horvath et al. | |
| 9,283,115 B2 | 3/2016 | Lind et al. | |
| 9,283,116 B2 | 3/2016 | Romoda et al. | |
| 9,289,324 B2 * | 3/2016 | Johnson | A61F 9/00781 |
| 9,326,891 B2 | 5/2016 | Horvath et al. | |
| 9,375,347 B2 | 6/2016 | Stergiopulos | |
| 9,393,153 B2 | 7/2016 | Horvath et al. | |
| 9,555,410 B2 | 1/2017 | Brammer et al. | |
| 9,585,789 B2 | 3/2017 | Silvestrini et al. | |
| 9,585,790 B2 | 3/2017 | Horvath et al. | |
| 9,592,154 B2 | 3/2017 | Romoda et al. | |
| 9,610,195 B2 | 4/2017 | Horvath | |
| 9,636,254 B2 | 5/2017 | Yu et al. | |
| 9,636,255 B2 | 5/2017 | Haffner et al. | |
| 9,655,778 B2 | 5/2017 | Tyler | |
| 9,655,779 B2 | 5/2017 | Bigler et al. | |
| 9,693,900 B2 | 7/2017 | Gallardo Inzunza | |
| 9,693,901 B2 | 7/2017 | Horvath et al. | |
| 9,757,276 B2 | 9/2017 | Penhasi | |
| 9,808,373 B2 | 11/2017 | Horvath et al. | |
| 9,877,866 B2 | 1/2018 | Horvath et al. | |
| 9,883,969 B2 | 2/2018 | Horvath et al. | |
| 9,980,854 B2 | 5/2018 | Horvath et al. | |
| 10,004,638 B2 | 6/2018 | Romoda et al. | |
| 10,080,682 B2 | 9/2018 | Horvath et al. | |
| 10,085,884 B2 | 10/2018 | Reitsamer et al. | |
| 10,154,924 B2 | 12/2018 | Clauson et al. | |
| 10,159,600 B2 | 12/2018 | Horvath et al. | |
| 10,195,078 B2 | 2/2019 | Horvath et al. | |
| 10,195,079 B2 | 2/2019 | Horvath et al. | |
| 10,231,871 B2 | 3/2019 | Hill | |
| 10,238,536 B2 | 3/2019 | Olson et al. | |
| 10,285,853 B2 | 5/2019 | Rangel-Friedman et al. | |
| 10,307,293 B2 | 6/2019 | Horvath et al. | |
| 10,314,743 B2 | 6/2019 | Romoda et al. | |
| 10,322,267 B2 | 6/2019 | Hakim | |
| 10,369,048 B2 | 8/2019 | Horvath et al. | |
| 10,405,903 B1 | 9/2019 | Biesinger et al. | |
| 10,335,030 B2 | 10/2019 | Alhourani | |
| 10,342,703 B2 | 11/2019 | Siewert et al. | |
| 10,463,537 B2 | 11/2019 | Horvath et al. | |
| 10,470,927 B2 | 11/2019 | Horvath et al. | |
| 10,363,168 B2 | 12/2019 | Schieber et al. | |
| 10,492,948 B2 | 12/2019 | Baerveldt | |
| 10,524,959 B2 | 1/2020 | Horvath | |
| 10,524,958 B2 | 3/2020 | Camras et al. | |
| 10,596,035 B2 | 4/2020 | Stergiopulos et al. | |
| 10,758,412 B2 | 4/2020 | Velasquez | |
| 10,716,663 B2 | 7/2020 | Salahieh et al. | |
| 11,122,975 B2 | 1/2021 | Rodger et al. | |
| 10,912,675 B2 | 2/2021 | Lubatschowski | |
| 11,166,847 B2 | 2/2021 | Badawi et al. | |
| 10,952,897 B1 | 3/2021 | Smith | |
| 10,960,074 B2 | 3/2021 | Berdahl | |
| 11,007,061 B2 | 5/2021 | Passman et al. | |
| 11,039,954 B2 | 6/2021 | Cohen et al. | |
| 11,058,581 B2 | 7/2021 | Mixter et al. | |
| 11,065,154 B1 | 7/2021 | Sponsel et al. | |
| 11,083,624 B2 | 8/2021 | Stein et al. | |
| 11,166,848 B2 | 11/2021 | Mixter et al. | |
| 11,166,849 B2 | 11/2021 | Mixter et al. | |
| 11,291,585 B2 | 4/2022 | Schultz et al. | |
| 11,517,477 B2 | 12/2022 | Lilly et al. | |
| 11,529,258 B2 | 12/2022 | Chang et al. | |
| 11,596,550 B2 | 3/2023 | Chang et al. | |
| 11,737,920 B2 | 8/2023 | Chang et al. | |
| 11,766,355 B2 | 9/2023 | Argento et al. | |
| 11,865,283 B2 | 1/2024 | Schultz et al. | |
| 2001/0011585 A1 | 8/2001 | Cassidy et al. | |
| 2002/0177891 A1 | 11/2002 | Miles et al. | |
| 2002/0193725 A1 | 12/2002 | Odrich | |
| 2003/0079329 A1 | 5/2003 | Yaron et al. | |
| 2003/0127090 A1 | 7/2003 | Gifford et al. | |
| 2003/0163079 A1 | 8/2003 | Burnett | |
| 2003/0183008 A1 | 10/2003 | Bang et al. | |
| 2004/0010219 A1 | 1/2004 | McCusker et al. | |
| 2004/0162545 A1 | 8/2004 | Brown et al. | |
| 2004/0190153 A1 | 9/2004 | Esch | |
| 2004/0193095 A1 | 9/2004 | Shadduck | |
| 2004/0254520 A1 | 12/2004 | Porteous et al. | |
| 2005/0049578 A1 | 3/2005 | Tu et al. | |
| 2005/0059956 A1 | 3/2005 | Varner et al. | |
| 2005/0182350 A1 | 8/2005 | Nigam | |
| 2005/0196424 A1 | 9/2005 | Chappa | |
| 2006/0004317 A1 | 1/2006 | Mauge et al. | |
| 2006/0069340 A1 | 3/2006 | Simon | |

(56) References Cited

U.S. PATENT DOCUMENTS

| | | |
|---|---|---|
| 2006/0155300 A1 | 7/2006 | Stamper et al. |
| 2006/0212113 A1 | 9/2006 | Shaolian et al. |
| 2006/0276739 A1 | 12/2006 | Brown |
| 2007/0010837 A1 | 1/2007 | Tanaka |
| 2007/0078371 A1 | 4/2007 | Brown et al. |
| 2007/0088432 A1 | 4/2007 | Solovay et al. |
| 2007/0265646 A1 | 11/2007 | McCoy et al. |
| 2007/0299487 A1 | 12/2007 | Shadduck |
| 2008/0077071 A1 | 3/2008 | Yaron et al. |
| 2008/0103440 A1 | 5/2008 | Ferren et al. |
| 2008/0119891 A1 | 5/2008 | Miles et al. |
| 2008/0125691 A1 | 5/2008 | Yaron et al. |
| 2008/0277332 A1 | 11/2008 | Liu |
| 2009/0012483 A1 | 1/2009 | Blott et al. |
| 2009/0036818 A1 | 2/2009 | Grahn et al. |
| 2009/0043321 A1 | 2/2009 | Conston et al. |
| 2009/0243956 A1 | 10/2009 | Keilman et al. |
| 2009/0259236 A2 | 10/2009 | Burnett et al. |
| 2009/0287136 A1 | 11/2009 | Castillejos |
| 2009/0314970 A1 | 12/2009 | McAvoy et al. |
| 2009/0326432 A1 | 12/2009 | Schmidt et al. |
| 2009/0326517 A1 | 12/2009 | Bork et al. |
| 2010/0114006 A1 | 5/2010 | Baerveldt |
| 2010/0234791 A1 | 9/2010 | Lynch et al. |
| 2010/0241077 A1 | 9/2010 | Geipel et al. |
| 2010/0249691 A1 | 9/2010 | Van Der Mooren et al. |
| 2011/0105986 A1 | 5/2011 | Bronstein et al. |
| 2012/0035525 A1 | 2/2012 | Silvestrini |
| 2012/0065570 A1 | 3/2012 | Yeung et al. |
| 2012/0078220 A1 | 3/2012 | Fallin et al. |
| 2012/0089073 A1 | 4/2012 | Cunningham, Jr. |
| 2012/0232461 A1 | 9/2012 | Seaver et al. |
| 2013/0085440 A1 | 4/2013 | Bohm et al. |
| 2013/0131577 A1 | 5/2013 | Bronstein et al. |
| 2013/0150773 A1 | 6/2013 | Nissan et al. |
| 2013/0150776 A1 | 6/2013 | Bohm et al. |
| 2013/0158381 A1 | 6/2013 | Rickard |
| 2013/0197621 A1 | 8/2013 | Ryan et al. |
| 2013/0199646 A1 | 8/2013 | Brammer et al. |
| 2013/0205923 A1 | 8/2013 | Brammer et al. |
| 2013/0211312 A1 | 8/2013 | Gelvin |
| 2013/0267887 A1 | 10/2013 | Kahook et al. |
| 2013/0317412 A1 | 11/2013 | Dacquay et al. |
| 2013/0338564 A1 | 12/2013 | Rickard et al. |
| 2014/0046439 A1 | 2/2014 | Dos Santos et al. |
| 2014/0081195 A1 | 3/2014 | Clauson et al. |
| 2014/0236068 A1 | 8/2014 | Van Der Mooren et al. |
| 2014/0309611 A1 | 10/2014 | Wilt et al. |
| 2015/0011926 A1 | 1/2015 | Reitsamer et al. |
| 2015/0034217 A1 | 2/2015 | Vad |
| 2015/0045716 A1 | 2/2015 | Gallardo Inzunza |
| 2015/0142049 A1 | 5/2015 | Delgado et al. |
| 2015/0230843 A1 | 8/2015 | Palmer et al. |
| 2015/0257931 A1 | 9/2015 | Sanchez et al. |
| 2015/0265469 A1 | 9/2015 | Olson et al. |
| 2015/0313603 A1 | 11/2015 | Bodewadt et al. |
| 2016/0058615 A1 | 3/2016 | Camras et al. |
| 2016/0067093 A1 | 3/2016 | Johnson et al. |
| 2016/0151179 A1 | 6/2016 | Favier et al. |
| 2016/0220794 A1 | 8/2016 | Negre |
| 2016/0256317 A1 | 9/2016 | Horvath et al. |
| 2016/0256318 A1 | 9/2016 | Horvath et al. |
| 2016/0256319 A1 | 9/2016 | Horvath et al. |
| 2016/0256320 A1 | 9/2016 | Horvath et al. |
| 2016/0287439 A1 | 10/2016 | Stergiopulos |
| 2016/0354244 A1 | 12/2016 | Horvath et al. |
| 2016/0354245 A1 | 12/2016 | Horvath et al. |
| 2017/0027582 A1 | 2/2017 | Khoury et al. |
| 2017/0071791 A1 | 3/2017 | Piven |
| 2017/0087016 A1 | 3/2017 | Camras |
| 2017/0172797 A1 | 6/2017 | Horvath et al. |
| 2017/0172798 A1 | 6/2017 | Horvath et al. |
| 2017/0172799 A1 | 6/2017 | Horvath |
| 2017/0312125 A1 | 11/2017 | Clauson et al. |
| 2017/0348149 A1 | 12/2017 | Stergiopulos et al. |
| 2017/0348150 A1 | 12/2017 | Horvath et al. |
| 2018/0014828 A1 | 1/2018 | Fonte et al. |
| 2018/0028361 A1 | 2/2018 | Haffner et al. |
| 2018/0028366 A1 | 2/2018 | Tout et al. |
| 2018/0092775 A1 | 4/2018 | de Juan, Jr. et al. |
| 2018/0147089 A1 | 5/2018 | Horvath et al. |
| 2018/0177633 A1 | 6/2018 | Haffner et al. |
| 2018/0206878 A1 | 7/2018 | Uspenski et al. |
| 2018/0250166 A1 | 9/2018 | Lubatschowski |
| 2018/0333296 A1 | 11/2018 | Heitzmann et al. |
| 2019/0000673 A1 | 1/2019 | Fjield et al. |
| 2019/0021907 A1 | 1/2019 | Horvath et al. |
| 2019/0038462 A1 | 2/2019 | Vandiest et al. |
| 2019/0038463 A1 | 2/2019 | Kasic |
| 2019/0046356 A1 | 2/2019 | Laroche |
| 2019/0060118 A1 | 2/2019 | Hill |
| 2019/0133826 A1 | 3/2019 | Horvath et al. |
| 2019/0121278 A1 | 4/2019 | Kawamura et al. |
| 2019/0142632 A1 | 5/2019 | Badawi et al. |
| 2019/0151079 A1 | 5/2019 | Zaldivar |
| 2019/0167475 A1 | 6/2019 | Horvath et al. |
| 2019/0240069 A1 | 8/2019 | Horvath et al. |
| 2019/0247231 A1 | 8/2019 | McClunan |
| 2019/0254873 A1 | 8/2019 | Camras et al. |
| 2019/0274881 A1 | 9/2019 | Romoda et al. |
| 2019/0274882 A1 | 9/2019 | Romoda et al. |
| 2019/0307608 A1 | 10/2019 | Lee et al. |
| 2019/0344057 A1 | 11/2019 | Cima et al. |
| 2019/0350758 A1 | 11/2019 | Horvath et al. |
| 2019/0353269 A1 | 11/2019 | Ossmer et al. |
| 2019/0358086 A1 | 11/2019 | Camras et al. |
| 2019/0374384 A1 | 12/2019 | Xie et al. |
| 2020/0069469 A1 | 3/2020 | Horvath et al. |
| 2020/0085620 A1 | 3/2020 | Euteneuer et al. |
| 2020/0121503 A1 | 4/2020 | Badawi et al. |
| 2020/0121504 A1 | 4/2020 | Stegmann et al. |
| 2020/0129332 A1 | 4/2020 | Van Der Mooren et al. |
| 2020/0170839 A1 | 6/2020 | Borrmann et al. |
| 2020/0179171 A1 | 6/2020 | Crimaldi et al. |
| 2020/0214891 A1 | 7/2020 | Bigler et al. |
| 2020/0229977 A1 | 7/2020 | Mixter et al. |
| 2020/0229980 A1 | 7/2020 | Horvath |
| 2020/0229981 A1 | 7/2020 | Mixter et al. |
| 2020/0229982 A1 | 7/2020 | Mixter et al. |
| 2020/0246188 A1 | 8/2020 | Horvath et al. |
| 2020/0253725 A1 | 8/2020 | Hadba et al. |
| 2020/0261271 A1 | 8/2020 | Horvath et al. |
| 2020/0276050 A1 | 9/2020 | Simons et al. |
| 2020/0306086 A1 | 10/2020 | Da Silva Curiel et al. |
| 2020/0345549 A1 | 11/2020 | Lu et al. |
| 2020/0376239 A1 | 12/2020 | Heilman et al. |
| 2021/0015665 A1 | 1/2021 | Hacker et al. |
| 2021/0030590 A1 | 2/2021 | Blanda et al. |
| 2021/0038158 A1 | 2/2021 | Haffner et al. |
| 2021/0069486 A1 | 3/2021 | Hakim |
| 2021/0106462 A1 | 4/2021 | Sherwood et al. |
| 2021/0128357 A1 | 5/2021 | de Juan, Jr. et al. |
| 2021/0137736 A1 | 5/2021 | Cavuto et al. |
| 2021/0137737 A1 | 5/2021 | Burns et al. |
| 2021/0161713 A1 | 6/2021 | Bouremel et al. |
| 2021/0196516 A1 | 7/2021 | Ianchulev |
| 2021/0205132 A1 | 7/2021 | Horvath et al. |
| 2021/0212858 A1 | 7/2021 | Tran et al. |
| 2021/0251806 A1 | 8/2021 | Schultz et al. |
| 2021/0282922 A1 | 9/2021 | Cohen-Tzemaeh et al. |
| 2021/0298948 A1 | 9/2021 | Haffner et al. |
| 2021/0315806 A1 | 10/2021 | Haffner |
| 2021/0330499 A1 | 10/2021 | Wardle et al. |
| 2022/0087865 A1 | 3/2022 | Argento et al. |
| 2022/0142818 A1 | 5/2022 | Chang et al. |
| 2022/0160545 A1 | 5/2022 | Mixter et al. |
| 2022/0160546 A1 | 5/2022 | Mixter et al. |
| 2022/0168146 A1 | 6/2022 | Badawi et al. |
| 2022/0202613 A1 | 6/2022 | Chang et al. |
| 2022/0203078 A1 | 6/2022 | May |
| 2022/0241565 A1 | 8/2022 | Nae et al. |
| 2022/0265974 A1 | 8/2022 | Saul et al. |
| 2022/0273491 A1 | 9/2022 | Brown |
| 2022/0339035 A1 | 10/2022 | Lilly et al. |

(56) References Cited

U.S. PATENT DOCUMENTS

| | | |
|---|---|---|
| 2022/0354695 A1 | 11/2022 | Badawi et al. |
| 2022/0387217 A1 | 12/2022 | Argento et al. |
| 2023/0086856 A1 | 3/2023 | Chang et al. |
| 2023/0092196 A1 | 3/2023 | Argento et al. |
| 2023/0201544 A1 | 6/2023 | Schultz et al. |
| 2023/0233378 A1 | 7/2023 | Chang et al. |
| 2023/0240891 A1 | 8/2023 | Lilly et al. |
| 2023/0285192 A1 | 9/2023 | Chang et al. |
| 2024/0139029 A1 | 5/2024 | Chang et al. |
| 2024/0173169 A1 | 5/2024 | Schultz et al. |
| 2024/0277522 A1 | 8/2024 | Schultz et al. |
| 2024/0277523 A1 | 8/2024 | Schultz et al. |
| 2024/0325697 A1 | 10/2024 | Schultz et al. |
| 2024/0399122 A1 | 12/2024 | Bronez et al. |

FOREIGN PATENT DOCUMENTS

| | | |
|---|---|---|
| AU | 2018412569 | 10/2020 |
| BR | 112017025859 A2 | 8/2018 |
| BR | 112020008969 | 10/2020 |
| CA | 2987953 A1 | 12/2016 |
| CA | 3067172 | 12/2018 |
| CA | 3080713 | 5/2019 |
| CA | 3093160 | 9/2019 |
| CN | 101360523 A | 2/2009 |
| CN | 101965211 A | 2/2011 |
| CN | 103476371 | 12/2013 |
| CN | 104490515 | 4/2015 |
| CN | 106726124 | 5/2017 |
| CN | 108743016 A | 11/2018 |
| CN | 111405875 | 7/2020 |
| CO | 2020011460 | 11/2020 |
| DE | 10217061 | 3/2003 |
| DE | 102010015447 A1 | 10/2011 |
| DE | 102017124885 A1 | 4/2019 |
| DE | 102018112065 A1 | 11/2019 |
| DE | 102019204846 A1 | 10/2020 |
| EP | 1292256 A1 | 3/2003 |
| EP | 1737531 A2 | 1/2007 |
| EP | 2552369 | 1/2017 |
| EP | 3302381 A1 | 4/2018 |
| EP | 1765234 | 10/2019 |
| EP | 2999430 | 11/2019 |
| EP | 2677981 | 4/2020 |
| EP | 3659495 | 6/2020 |
| EP | 3518846 | 8/2020 |
| EP | 3666236 | 8/2020 |
| EP | 3687374 | 8/2020 |
| EP | 3706653 | 9/2020 |
| EP | 3730104 | 10/2020 |
| EP | 3735947 | 11/2020 |
| EP | 3773377 | 2/2021 |
| EP | 3846747 | 7/2021 |
| EP | 3846748 | 7/2021 |
| EP | 3329884 | 8/2021 |
| EP | 2389138 | 9/2021 |
| EP | 3870120 | 9/2021 |
| EP | 3313335 | 11/2021 |
| ES | 2725550 | 9/2019 |
| GB | 2602434 | 9/2022 |
| HK | 1252748 | 5/2019 |
| HU | E043303 | 8/2019 |
| JP | 2001-523519 | 11/2001 |
| JP | 2013505065 | 2/2013 |
| JP | 5576427 B2 | 8/2014 |
| JP | 2018-501010 | 1/2018 |
| JP | 2018519892 | 7/2018 |
| JP | 2018130580 | 8/2018 |
| JP | 2018529466 | 10/2018 |
| JP | 2019517366 | 6/2019 |
| JP | 2019205934 | 12/2019 |
| JP | 2020049361 | 4/2020 |
| KR | 2018015684 A | 2/2018 |
| KR | 20190019966 | 2/2019 |
| KR | 20200021551 | 2/2020 |
| KR | 20200059305 | 5/2020 |
| PL | 2640455 | 8/2019 |
| PT | 2640455 | 5/2019 |
| RU | 2687764 | 5/2019 |
| RU | 2018142990 | 6/2020 |
| SG | 11202008604 | 10/2020 |
| TR | 201906873 | 6/2019 |
| WO | WO1996019249 | 6/1996 |
| WO | WO2004073564 | 9/2004 |
| WO | WO2004081613 | 9/2004 |
| WO | WO2007011302 A1 | 1/2007 |
| WO | WO2007087061 | 8/2007 |
| WO | WO2009111645 | 9/2009 |
| WO | WO2010111528 | 9/2010 |
| WO | WO2011034740 | 3/2011 |
| WO | WO2012040380 | 3/2012 |
| WO | WO2012113450 | 8/2012 |
| WO | WO2014130574 | 8/2014 |
| WO | WO2016100500 | 6/2016 |
| WO | WO2016149425 | 9/2016 |
| WO | WO2016196841 A1 | 12/2016 |
| WO | WO2017058656 | 4/2017 |
| WO | WO2018229766 | 12/2018 |
| WO | WO2019018807 | 1/2019 |
| WO | WO2019094004 A1 | 5/2019 |
| WO | WO2019165053 | 8/2019 |
| WO | WO2019172940 | 9/2019 |
| WO | WO2020049508 | 3/2020 |
| WO | WO2020150663 | 7/2020 |
| WO | WO2020215068 | 10/2020 |
| WO | WO2020223491 | 11/2020 |
| WO | WO2020231993 | 11/2020 |
| WO | WO2020247365 | 12/2020 |
| WO | WO2020261184 | 12/2020 |
| WO | WO2021007294 | 1/2021 |
| WO | WO2021007296 | 1/2021 |
| WO | WO2021028703 | 2/2021 |
| WO | WO2021068078 | 4/2021 |
| WO | WO2021072315 | 4/2021 |
| WO | WO2021072317 | 4/2021 |
| WO | WO2021113730 | 6/2021 |
| WO | WO2021142255 | 7/2021 |
| WO | WO2021151007 | 7/2021 |
| WO | WO2021163566 | 8/2021 |
| WO | WO2021168130 | 8/2021 |
| WO | WO2021174298 | 9/2021 |
| WO | WO2021176332 | 9/2021 |
| WO | WO2021188952 | 9/2021 |
| WO | WO2021204312 | 10/2021 |
| WO | WO2021212007 | 10/2021 |
| WO | WO2021230887 | 11/2021 |
| WO | WO2022159723 | 7/2022 |
| WO | WO2022175681 | 8/2022 |
| WO | WO2022220861 | 10/2022 |
| WO | WO2023004067 | 1/2023 |
| WO | WO2023278452 | 1/2023 |
| WO | WO2023009366 | 2/2023 |
| WO | WO2023063961 | 4/2023 |
| WO | WO2023064491 | 4/2023 |
| WO | WO2023091307 | 5/2023 |
| WO | WO2023107486 | 6/2023 |
| WO | WO2023215461 | 11/2023 |
| WO | WO2024026397 | 2/2024 |
| WO | WO2024030949 | 2/2024 |
| WO | WO2024097723 | 5/2024 |
| WO | WO2024097743 | 5/2024 |
| WO | WO2024220861 | 10/2024 |
| ZA | 201708295 | 5/2020 |

OTHER PUBLICATIONS

English translation of Japanese Office Action received for Application No. 2022-521301, Applicant: Shifamed Holdings, LLC, Date of Mailing: Jun. 3, 2024, 3 pages.

International Search Report and Written Opinion received for PCT Application No. PCT/US22/52002, filed on Dec. 6, 2022, Applicant: Shifamed Holdings, LLC, Date of Mailing: Mar. 21, 2023, 11 pages.

(56) References Cited

OTHER PUBLICATIONS

International Search Report and Written Opinion received for PCT Application No. PCT/US22/46604, filed on Oct. 13, 2022, Applicant: Shifamed Holdings, LLC, Date of Mailing: Mar. 30, 2023, 11 pages.
International Search Report and Written Opinion received for PCT Application No. PCT/US24/25489, Applicant: Shifamed Holdings, LLC, Date of Mailing: Sep. 9, 2024, 18 pages.
International Search Report and Written Opinion received for PCT Application No. PCT/US22/35324, filed on Jun. 28, 2022, Applicant: Shifamed Holdings, LLC, Date of Mailing: Nov. 22, 2022, 12 pages.
International Search Report and Written Opinion received for PCT Application No. PCT/US22/37917, filed on Jul. 21, 2022, Applicant: Shifamed Holdings, LLC, Date of Mailing: Dec. 15, 2022, 15 pages.
Keulegan et al. "Pressure Losses for Fluid Flow in Curved Pipes," Journal of Research of the National Bureau of Standards, vol. 18, Jan. 31, 1937 (Jan. 31, 1937), 26 pages.
Olsen et al. "Human sclera: thickness and surface area," American Journal of Ophthalmology, vol. 125, Issue. 2, https://pubmed.nobl.nim.nih.gov/9467451, Feb. 1, 1998 (Feb. 1, 1998), 1 page.
International Search Report and Written Opinion received for PCT Application No. PCT/US22/048863, filed on Nov. 3, 2022, Applicant: Shifamed Holdings, LLC, Date of Mailing: Feb. 16, 2023, 13 pages.
Extended European Search Report received for EP Application No. 21744394.4, Applicant: Shifamed Holdings, LLC, Date of Mailing: Jan. 26, 2024, 7 pages.
Extended European Search Report received for EP Application No. 22743262.2; Applicant: Shifamed Holdings, LLC, Date of Mailing: Oct. 28, 2024, 8 pages.
Collins Dictionary, Textured definition and meaning, 2024, Collins Dictionary, https://www.collinsdictionary.com/dictionary/english/textured, Year: 2024, 1 page.
English translation of Chinese Office Action received for CN Application No. 201880060989.1; Applicant: Shifamed Holdings, LLC, Date of Mailing: Oct. 18, 2024, 9 pages.
Extended European Search Report received for EP Application No. 23158246.1, Applicant: Shifamed Holdings, LLC, Date of Mailing: Aug. 7, 2023, 7 pages.
International Search Report and Written Opinion received for PCT Application No. PCT/US23/64636, filed on Mar. 17, 2023, Applicant: Shifamed Holdings, LLC, Date of Mailing: Sep. 5, 2023, 9 pages.
International Search Report and Written Opinion received for PCT Application No. PCT/US23/20973, filed on May 4, 2023, Applicant: Shifamed Holdings, LLC, Date of Mailing: Sep. 21, 2023, 15 pages.
Extended European Search Report received for EP Application No. 20874212.2, Applicant: Shifamed Holdings, LLC, Date of Mailing: Oct. 18, 2023, 8 pages.
Extended European Search Report received for EP Application No. 20875070.3, Applicant: Shifamed Holdings, LLC, Date of Mailing: Dec. 19, 2023, 7 pages.
International Search Report and Written Opinion received for PCT Application No. PCT/US23/71501, filed on Aug. 2, 2023, Applicant: Shifamed Holdings, LLC, Date of Mailing: Jan. 18, 2024, 20 pages.
Extended European Search Report received for EP Application No. 21787751.3; Applicant: Shifamed Holdings, LLC, Date of Mailing: Mar. 15, 2024, 8 pages.
International Search Report and Written Opinion received for PCT Application No. PCT/US23/71106, filed on Jul. 27, 2023, Applicant: Shifamed Holdings, LLC, Date of Mailing: Mar. 1, 2024, 12 pages.
International Search Report and Written Opinion received for PCT Application No. PCT/US18/43158, filed on Jul. 20, 2018, Applicant: Shifamed Holdings, LLC, Date of Mailing: Nov. 23, 2018, 12 pages.
International Search Report and Written Opinion received for PCT Application No. PCT/US20/41159, filed on Jul. 8, 2020, Applicant: Shifamed Holdings, LLC, Date of Mailing: Oct. 28, 2020, 13 pages.
International Search Report and Written Opinion received for PCT Application No. PCT/US20/41152, filed on Jul. 8, 2020, Applicant: Shifamed Holdings, LLC, Date of Mailing: Oct. 28, 2020, 13 pages.
International Search Report and Written Opinion received for PCT Application No. PCT/US20/14186, filed on Jan. 17, 2020, Applicant: Shifamed Holdings, LLC, Date of Mailing: Jun. 4, 2020, 13 pages.
International Search Report and Written Opinion received for PCT Application No. PCT/US21/17962, filed on Feb. 12, 2021, Applicant: Shifamed Holdings, LLC, Date of Mailing: Jun. 7, 2021, 12 pages.
International Search Report and Written Opinion received for PCT Application No. PCT/US21/27742, filed on Apr. 16, 2021, Applicant: Shifamed Holdings, LLC, Date of Mailing: Oct. 7, 2021, 13 pages.
International Search Report and Written Opinion received for PCT Application No. PCT/US21/49140, filed on Sep. 3, 2021, Applicant: Shifamed Holdings, LLC, Date of Mailing: Dec. 7, 2021, 22 pages.
International Search Report and Written Opinion received for PCT Application No. PCT/US21/55258, filed on Oct. 15, 2021, Applicant: Shifamed Holdings, LLC, Date of Mailing: Feb. 28, 2022, 18 pages.
International Search Report and Written Opinion received for PCT Application No. PCT/US22/13336, filed on Jan. 21, 2022, Applicant: Shifamed Holdings, LLC, Date of Mailing: Apr. 11, 2022, 9 pages.

* cited by examiner

SHUNTING SYSTEMS WITH ROTATION-BASED FLOW CONTROL ASSEMBLIES, AND ASSOCIATED SYSTEMS AND METHODS

CROSS-REFERENCE TO RELATED APPLICATION(S)

The present application is a continuation of U.S. patent application Ser. No. 17/175,332, filed Feb. 12, 2021, which claims priority to the following provisional applications:

U.S. Provisional Patent Application No. 62/976,890, filed Feb. 14, 2020;

U.S. Provisional Patent Application No. 62/981,411, filed Feb. 25, 2020;

U.S. Provisional Patent Application No. 63/116,674, filed Nov. 20, 2020; and

U.S. Provisional Patent Application No. 63/140,543, filed Jan. 22, 2021.

All of the foregoing applications are incorporated herein by reference in their entireties. Further, components and features of embodiments disclosed in the applications incorporated by reference may be combined with various components and features disclosed and claimed in the present application.

TECHNICAL FIELD

The present technology generally relates to implantable medical devices and, in particular, to intraocular shunting systems and associated methods for selectively controlling fluid flow between different portions of a patient's eye.

BACKGROUND

Glaucoma is a degenerative ocular condition involving damage to the optic nerve that can cause progressive and irreversible vision loss. Glaucoma is frequently associated with ocular hypertension, an increase in pressure within the eye resultant from an increase in production of aqueous humor ("aqueous") within the eye and/or a decrease in the rate of outflow of aqueous from within the eye into the blood stream. Aqueous is produced in the ciliary body at the boundary of the posterior and anterior chambers of the eye. It flows into the anterior chamber and eventually into the capillary bed in the sclera of the eye. Glaucoma is typically caused by a failure in mechanisms that transport aqueous out of the eye and into the blood stream.

BRIEF DESCRIPTION OF THE DRAWINGS

Many aspects of the present technology can be better understood with reference to the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

DETAILED DESCRIPTION

Figure 1A:
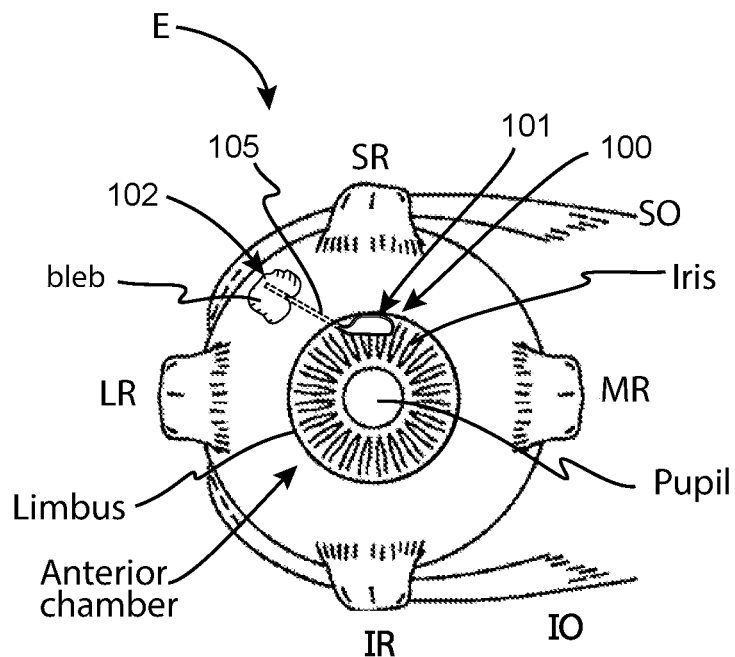
FIG. 1A is a simplified front view of an eye with an implanted shunt configured in accordance with an embodiment of the present technology.

The present technology is generally directed to shunting systems for selectively controlling the flow of fluid between a first body region of a patient, such as an anterior chamber of the patient's eye, and a second body region of the patient, such as a bleb space. The shunting systems disclosed herein can include a drainage element having a channel extending therethrough for transporting fluid from the first body region to the second body region. The shunting systems can also include a flow control assembly or actuator having a control element rotatably moveable relative to the drainage element, and at least one shape memory actuation element that, when actuated, pivots or otherwise rotates the control element relative to the drainage element. Pivoting/rotating the control element can change the fluid resistance through one or more apertures (e.g., fluid inlets) in fluid communication with the channel, thereby changing the drainage rate through the drainage element. As described in detail below, use of a rotational motion to control the flow of fluid through a shunting system is expected to provide several advantages over flow control elements that rely on linear motion.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1-17.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%. Reference throughout this specification to the term "resistance" refers to fluid resistance unless the context clearly dictates otherwise. The terms "drainage rate," "flow rate," and "flow" are used interchangeably to describe the movement of fluid through a structure.

Although certain embodiments herein are described in terms of shunting fluid from an anterior chamber of an eye, one of skill in the art will appreciate that the present technology can be readily adapted to shunt fluid from and/or between other portions of the eye, or, more generally, from and/or between a first body region and a second body region. Moreover, while the certain embodiments herein are described in the context of glaucoma treatment, any of the embodiments herein, including those referred to as "glaucoma shunts" or "glaucoma devices" may nevertheless be used and/or modified to treat other diseases or conditions, including other diseases or conditions of the eye or other body regions. For example, the systems described herein can be used to treat diseases characterized by increased pressure and/or fluid build-up, including but not limited to heart failure (e.g., heart failure with preserved ejection fraction, heart failure with reduced ejection fraction, etc.), pulmonary failure, renal failure, hydrocephalus, and the like. Moreover, while generally described in terms of shunting aqueous, the systems described herein may be applied equally to shunting other fluid, such as blood or cerebrospinal fluid, between the first body region and the second body region.

The headings provided herein are for convenience only and do not interpret the scope or meaning of the claimed present technology.

A. Intraocular Shunts for Glaucoma Treatment

Glaucoma refers to a group of eye diseases associated with damage to the optic nerve which eventually results in vision loss and blindness. As noted above, glaucoma is a degenerative ocular condition characterized by an increase in pressure within the eye resulting from an increase in production of aqueous within the eye and/or a decrease in the rate of outflow of aqueous from within the eye into the blood stream. The increased pressure leads to injury of the optic nerve over time. Unfortunately, patients often do not present with symptoms of increased intraocular pressure until the onset of glaucoma. As such, patients typically must be closely monitored once increased pressure is identified even if they are not symptomatic. The monitoring continues over the course of the disease so clinicians can intervene early to stem progression of the disease. Monitoring pressure requires patients to visit a clinic site on a regular basis which is expensive, time-consuming, and inconvenient. The early stages of glaucoma are typically treated with drugs (e.g., eye drops) and/or laser therapy. When drug/laser treatments no longer suffice, however, surgical approaches can be used. Surgical or minimally invasive approaches primarily attempt to increase the outflow of aqueous from the anterior chamber to the blood stream either by the creation of alternative fluid paths or the augmentation of the natural paths for aqueous outflow.

Figure 1B:
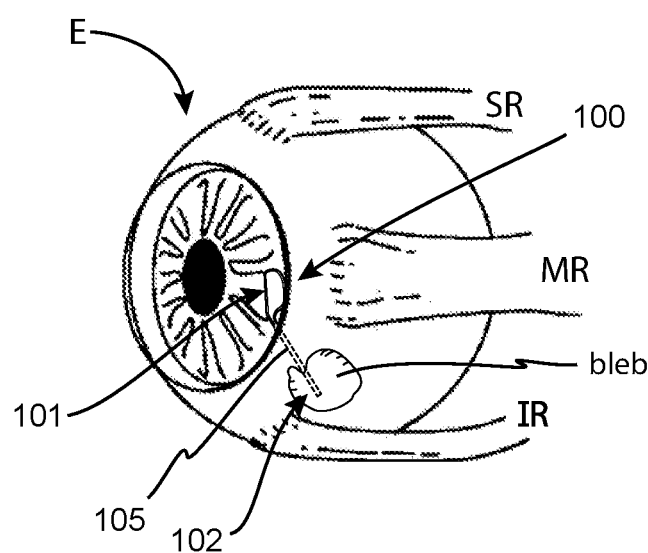
FIG. 1B is an isometric view of the eye and implanted shunt of FIG. 1A.

FIGS. 1A and 1B illustrate a human eye E and suitable location(s) in which a shunt may be implanted within the eye E in accordance with embodiments of the present technology. More specifically, FIG. 1A is a simplified front view of the eye E with an implanted shunt 100, and FIG. 1B is an isometric view of the eye E and the shunt 100 of FIG. 1A. Referring first to FIG. 1A, the eye E includes a number of muscles to control its movement, including a superior rectus SR, inferior rectus IR, lateral rectus LR, medial rectus MR, superior oblique SO, and inferior oblique IO. The eye E also includes an iris, pupil, and limbus.

Referring to FIGS. 1A and 1B together, the shunt 100 can have a drainage element 105 (e.g., a drainage tube) positioned such that an inflow portion 101 is positioned in an anterior chamber of the eye E, and an outflow portion 102 is positioned at a different location within the eye E, such as a bleb space. The shunt 100 can be implanted in a variety of orientations. For example, when implanted, the drainage element 105 may extend in a superior, inferior, medial, and/or lateral direction from the anterior chamber. Depending upon the design of the shunt 100, the outflow portion 102 can be placed in a number of different suitable outflow locations (e.g., between the choroid and the sclera, between the conjunctiva and the sclera, etc.).

Outflow resistance can change over time for a variety of reasons, e.g., as the outflow location goes through its healing process after surgical implantation of a shunt (e.g., shunt 100) or further blockage in the drainage network from the anterior chamber through the trabecular meshwork, Schlemm's canal, the collector channels, and eventually into the vein and the body's circulatory system. Accordingly, a clinician may desire to modify the shunt after implantation to either increase or decrease the outflow resistance in response to such changes or for other clinical reasons. For example, in many procedures the shunt is modified at implantation to temporarily increase its outflow resistance. After a period of time deemed sufficient to allow for healing of the tissues and stabilization of the outflow resistance, the modification to the shunt is reversed, thereby decreasing the outflow resistance. In another example, the clinician may implant the shunt and after subsequent monitoring of intraocular pressure determine a modification of the drainage rate through the shunt is desired. Such modifications can be invasive, time-consuming, and/or expensive for patients. If such a procedure is not followed, however, there is a high likelihood of creating hypotony (excessively low eye pressure), which can result in further complications, including damage to the optic nerve. In contrast, intraocular shunting systems configured in accordance with embodiments of the present technology allow the clinician to selectively adjust the flow of fluid through the shunt after implantation without additional invasive surgical procedures.

The shunts described herein can be implanted having a first drainage rate and subsequently remotely adjusted to achieve a second, different drainage rate. The adjustment can be based on the needs of the individual patient. For example, the shunt may be implanted at a first lower flow rate and subsequently adjusted to a second higher flow rate as clinically necessary. The shunts described herein can be delivered using either ab interno or ab externo implant techniques, and can be delivered via needles. The needles can have a variety of shapes and configurations to accommodate the various shapes of the shunts described herein. Details of the implant procedure, the implant devices, and bleb formation are described in greater detail in International Patent Application No. PCT/US20/41152, the disclosure of which is incorporated by reference herein for all purposes.

In many of the embodiments described herein, the flow control assemblies are configured to introduce features that selectively impede or attenuate fluid flow through the shunt during operation. In this way, the flow control assemblies can incrementally or continuously change the flow resistance through the shunt to selectively regulate pressure and/or flow. The flow control assemblies configured in accordance with the present technology can accordingly adjust the level of interference or compression between a number of different positions, and accommodate a multitude of variables (e.g., IOP, aqueous production rate, native aqueous outflow resistance, and/or native aqueous outflow rate) to precisely regulate flow rate through the shunt.

The disclosed flow control assemblies can be operated using energy. This feature allows such devices to be implanted in the patient and then modified/adjusted over time without further invasive surgeries or procedures for the patient. Further, because the devices disclosed herein may be actuated via energy from an external energy source (e.g., a laser), such devices do not require any additional power to maintain a desired orientation or position. Rather, the actuators/fluid resistors disclosed herein can maintain a desired position/orientation without power. This can significantly increase the usable lifetime of such devices and enable such devices to be effective long after the initial implantation procedure.

B. Operation of Actuation Elements

Some embodiments of the present technology include actuation assemblies (e.g., flow control assemblies, flow control mechanisms, etc.) that have at least one actuation element coupled to a moveable control element (e.g., an arm, a gating element, a projection, etc.). As described in detail below, the moveable control element can be configured to interface with (e.g., at least partially block) a corresponding port or aperture. The port can be an inflow port or an outflow port. Movement of the actuation element(s) generates (e.g., translational and/or rotational) movement of the moveable element.

The actuation element(s) can include a shape memory material (e.g., a shape memory alloy, or a shape memory polymer). Movement of the actuation element(s) can be generated through applied stress and/or use of a shape memory effect (e.g., as driven by a change in temperature). The shape memory effect enables deformations that have altered an element from its preferred geometric configuration (e.g., original or fabricated configuration, shape-set configuration, heat-set configuration, etc.) to be largely or entirely reversed during operation of the flow control assembly. For example, thermal actuation (heating) can reverse deformation(s) by inducing a change in state (e.g., phase change) in the actuator material, inducing a temporary elevated internal stress that promotes a shape change toward the preferred geometric configuration. For a shape memory alloy, the change in state can be from a martensitic phase (alternatively, R-phase) to an austenitic phase. For a shape memory polymer, the change in state can be via a glass transition temperature or a melting temperature. The change in state can reverse deformation(s) of the material—for example, deformation with respect to its preferred geometric configuration—without any (e.g., externally) applied stress to the actuation element. That is, a deformation that is present in the material at a first temperature (e.g., body temperature) can be (e.g., thermally) recovered and/or altered by raising the material to a second (e.g., higher) temperature. Upon cooling (and changing state, e.g., back to martensitic phase), the actuation element retains its preferred geometric configuration. With the material in this relatively cooler-temperature condition it may require a lower force or stress to thermoelastically deform the material, and any subsequently applied external stress can cause the actuation element to once again deform away from the original geometric configuration.

The actuation element(s) can be processed such that a transition temperature at which the change in state occurs (e.g., the austenite start temperature, the austenite final temperature, etc.) is above a threshold temperature (e.g., body temperature). For example, the transition temperature can be set to be about 45 deg. C., about 50 deg. C., about 55 deg. C., or about 60 deg. C. In some embodiments, the actuator material is heated from body temperature to a temperature above the austenite start temperature (or alternatively above the R-phase start temperature) such that an upper plateau stress (e.g., "UPS_body temperature") of the material in a first state (e.g., thermoelastic martensitic phase, or thermoelastic R-phase at body temperature) is lower than an upper plateau stress (e.g., "UPS_actuated temperature") of the material in a heated state (e.g., superelastic state), which achieves partial or full free recovery. For example, the actuator material can be heated such that UPS_actuated temperature>UPS_body temperature. In some embodiments, the actuator material is heated from body temperature to a temperature above the austenite start temperature (or alternatively above the R-phase start temperature) such that an upper plateau stress of the material in a first state (e.g., thermoelastic martensite or thermoelastic R-phase at body temperature) is lower than a lower plateau stress (e.g., "LPS") of the material in a heated state (e.g., superelastic state), which achieves partial or full free recovery. For example, the actuator material can be aged such that LPS_activated temperature>UPS_body temperature. In some embodiments, the actuator material is heated from body temperature to a temperature above the austenite start temperature (or alternatively above the R-phase start temperature) such that an upper plateau stress of the material in a first state (e.g., thermoelastic martensite or thermoelastic R-phase) is higher than a lower plateau stress of the material in a heated state, which achieves partial free recovery. For example, the actuator material can be aged such that LPS_activated temperature<UPS_body temperature.

The flow control assembly can be formed such that the actuation elements have substantially the same preferred geometric configuration (e.g., memory shape, or length, L0). The flow control assembly can be assembled such that, upon introduction into a patient (e.g., implantation), at least one (e.g., a first) actuation element/shape memory element has been deformed with respect to its preferred geometric configuration (e.g., to have L1≠L0), while at least one other opposing (e.g., a second) actuation element/shape memory element positioned adjacent to the first actuation element is substantially at its preferred geometric configuration (e.g., L0). In other embodiments, however, both the first and second actuation elements may be deformed with respect to their corresponding preferred geometric configuration upon introduction into the patient (e.g., the first actuation element is contracted relative to its preferred geometric configuration and the second actuation element is expanded relative to its preferred geometric configuration).

In some embodiments of the present technology, L1>L0—for example, the deformed first actuation element is elongated with respect to its preferred "shape memory" length. In some embodiments, L1<L0—for example, the deformed first actuation element is compressed with respect to its preferred shape memory length. The flow control assembly can be formed such that, in operation, its overall dimension (e.g., overall length) is substantially fixed (e.g., L0+L1=a constant). For example, (e.g., outermost) ends of the actuation elements can be fixed, such that movement of the actuation elements occurs between the points of fixation. The overall geometry of the actuation elements, along with the lengths, can be selected such that, in operation, deformation within the actuation elements remains below about 10%, about 9%, about 8%, about 7%, or about 6%.

The (e.g., first and second) actuation elements are arranged such that a movement (e.g., deflection or deformation) of the first actuation element/first shape memory element is accompanied by (e.g., causes) an opposing movement of the second actuation element/second shape memory element. The movement can be a deflection or a deformation. In operation, selective heating of the first actuation element of the flow control assembly causes it to move to and/or toward its preferred geometric configuration (e.g., revert from L1 to L0), moving the coupled moveable element. At the same time, the elongation of the first actuation element is accompanied by (e.g., causes) a compression of the second actuation element (e.g., from L0 to L1). The second actuation element is not heated (e.g., remains at body temperature), and therefore the second actuation element deforms (e.g., remains martensitic and compresses). The first actuation element cools following heating, and returns to a state in which it can be plastically deformed. To reverse the configuration of the flow control assembly (e.g., the position of the moveable element), the second actuation element is heated to move to and/or toward its preferred geometric configuration (e.g., from L1 to L0). The return of the second actuation element to its preferred geometric configuration causes the moveable element to move back to its prior position, and compresses the first actuation element (e.g., from L0 to L1). The position of the moveable element for the flow control assembly can be repeatably toggled (e.g., between open and closed) by repeating the foregoing operations. The heating of an actuation element can be accomplished via application of incident energy (e.g., via a laser or inductive coupling). Further, as mentioned above, the source of the incident energy may be external to the patient (e.g., non-invasive).

C. Flow Control Assemblies for Intraocular Shunting Systems

As provided above, the present technology is generally directed to intraocular shunting systems. Such systems include a drainage element (e.g., an elongated flow tube or plate) configured to shunt fluid away from the anterior chamber of the eye. For example, the drainage element can include an inflow portion configured for placement within the anterior chamber (e.g., at a location away from the optical field of view) and an outflow portion configured for placement at a different location of the eye (e.g., at a subconjunctival bleb space). To selectively control fluid flow through the drainage element (e.g., post-implantation), the system can further include a flow control assembly operably coupled to the drainage element. In some embodiments, the flow control assembly includes a rotational control element operably coupled to a portion of the drainage element (e.g., to the outflow or to the inflow portion). The rotational control element can be or include a cam, plate, lever, gate valve, or any other structure capable of rotating to a plurality of different orientations. The orientation of the rotational control element or a component thereof can affect the amount of fluid flow through the portion of the drainage element.

Figure 2:
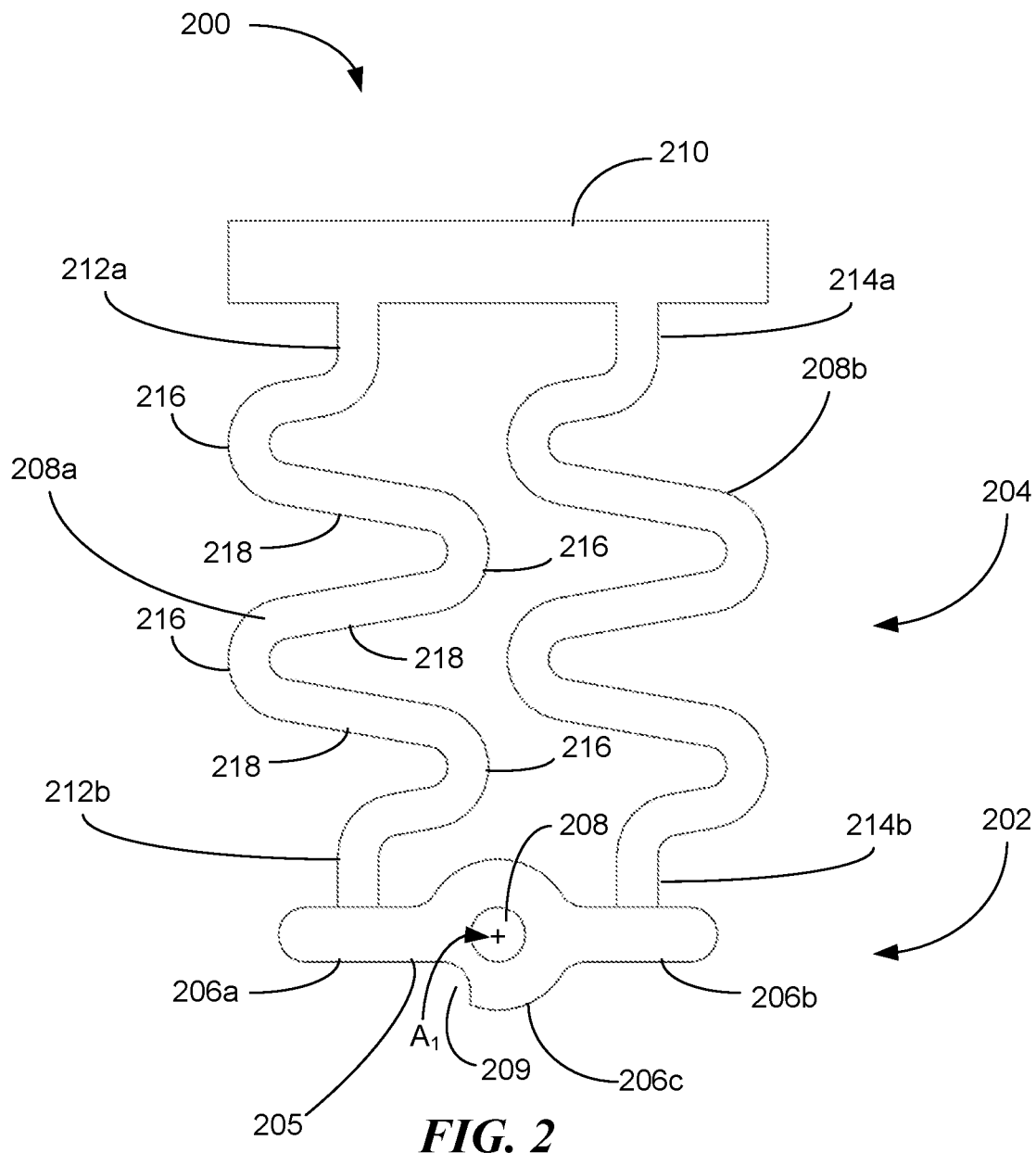
FIG. 2 is a front view of a flow control assembly of an intraocular shunting system configured in accordance with an embodiment of the present technology.

FIG. 2 is a front view of a flow control assembly 200 of an intraocular shunting system configured in accordance with an embodiment of the present technology. The flow control assembly 200 includes a rotational control element 202 coupled to an actuation structure 204. The rotational control element 202 can include an elongated member 205 having a first end portion 206a, a second end portion 206b, and a cam portion 206c disposed between the first and second end portions 206a-b. The elongated member 205 can be configured to rotate about a rotational axis $A_1$ (e.g., in a clockwise and/or counterclockwise direction). In some embodiments, the cam portion 206c includes an aperture 208 configured to receive a fastener (e.g., a pin, screw, pivot, etc.—not shown) allowing for rotation of the elongated member 205 about the rotational axis $A_1$.

The rotational control element 202 can be operably coupled to an outflow portion of a drainage element (not shown) to selectively control fluid flow therethrough (e.g., to modulate pressure within the anterior chamber of the eye). For example, the outflow portion can include one or more apertures formed therein to permit fluid outflow (e.g., similar to the outflow ports 102 described with respect to FIGS. 1A and 1B). The rotational control element 202 can be positioned near or adjacent to the aperture(s) such that, depending on the orientation of the rotational control element 202, one or more apertures can be obstructed or unobstructed by the rotational control element 202. When rotated to a first orientation, the rotational control element 202 can partially or completely cover the aperture(s) to partially or completely obstruct fluid flow therefrom. When rotated to a second orientation, the rotational control element 202 can be spaced away from the aperture(s) such that the aperture(s) are accessible and fluid can flow therefrom with little or no obstruction. As a result, the amount of fluid flow through the outflow portion can vary based on the number of obstructed aperture(s) and/or the extent to which each aperture is obstructed. In other embodiments, the rotational control element 202 is coupled to an inflow portion of a drainage element (not shown) such that one or more inflow apertures (not shown) can be unobstructed or partially to fully obstructed or unobstructed by the rotational control element 202.

In the illustrated embodiment, for example, the elongated member 205 or a component thereof (e.g., the cam portion 206c, the first end portion 206a, and/or the second end portion 206b) can be positioned near or adjacent to the aperture(s) of an outflow portion of a drainage element (not shown). When the elongated member 205 is rotated to a first orientation, the cam portion 206c can partially or completely cover the aperture(s). In some embodiments, when the elongated member 205 is rotated to a second orientation, a notch 209 formed in the cam portion 206c can be positioned over the aperture(s) such that the cam portion 206c is spaced apart from the aperture(s) and no longer obstructs fluid flow therethrough.

The actuation structure 204 can be configured to implement rotation of the rotational control element 202. In the illustrated embodiment, for example, the actuation structure 204 includes a first actuation element 208a and a second actuation element 208b coupled to the rotational control element 202 (e.g., to elongated member 205). The first and second actuation elements 208a-b can each be carried by a base support 210 and can extend longitudinally between the base support 210 and the rotational control element 202. For example, the first actuation element 208a can include a first end portion 212a coupled to the base support 210 and a second end portion 212b coupled to the first end portion 206a of the elongated member 205. The second actuation element 208b can include a first end portion 214a coupled to the base support 210 and a second end portion 214b coupled to the second end portion 206b of the elongated member 205.

In some embodiments, the first and second actuation elements 208a-b include one or more shape memory materials configured to at least partially transition from a first phase/state (e.g., a martensitic or intermediate state) to a second phase/state (e.g., an intermediate or austenitic state) upon application of energy, as previously described. The first and second actuation elements 208a-b can each be configured to change in shape or otherwise transform between a first configuration (e.g., a memory shape, a preferred geometry, etc.) and a second configuration (e.g., a shape different from the memory shape, a deformed geometry, etc.) via a shape memory effect (e.g., when heated). For example, in some embodiments, the memory shape is a lengthened configuration, while in other embodiments the memory shape is a shortened configuration.

In the illustrated embodiment, the first actuation element 208a can be configured to transform to a lengthened configuration when heated to rotatably move the rotational control element 202 along a first direction (e.g., counter-clockwise), and the second actuation element 208b can be configured to transform to a lengthened configuration when heated to rotatably move the rotational control element 202 along a second, opposite direction (e.g., clockwise). In other embodiments, the first actuation element 208a can be configured to transform to a shortened configuration when heated to rotatably move the rotational control element 202 along a first direction (e.g., clockwise), and the second actuation element 208b can be configured to transform to a shortened configuration when heated to rotatably move the rotational control element 202 along a second, opposite direction (e.g., counterclockwise). Optionally, the first and second actuation elements 208a-b can be configured to oppose each other, such that actuation of one actuation element via the shape memory effect produces a corresponding deflection and/or deformation in the other actuation element. For example, transformation of one actuation element into a lengthened configuration can cause the other actuation element to transform into a shortened configuration, and/or transformation of one actuation element into a shortened configuration can cause the other actuation element to transform into a lengthened configuration.

The geometry of the first and second actuation element 208a-b can be configured in a number of different ways. For example, in the illustrated embodiment, the first and second actuation elements 208a-b each include a plurality of apices or bend regions 216 and a plurality of struts 218 interconnected with each other to form a serpentine or "zig-zag"-shaped structure (reference numbers are shown only for the apices and struts of the first actuation element 208a merely for purposes of clarity). The first and second actuation elements 208a-b can each be transformed to the lengthened configuration by moving the apices 216 and/or struts 218 further away from each other (e.g., along a longitudinal direction). Conversely, the first and section actuation elements 208a-b can each be transformed to the shortened configuration by moving the apices 216 and/or struts 218 closer to each other (e.g., along a longitudinal direction).

In some embodiments, the first and second actuation elements 208a-b are each individually actuated by applying a stimulus to the entire actuation element. In other embodiments the stimulus can be applied to only a portion of the actuation element. For example, a stimulus can be applied to a plurality of different locations, such as to one or more apices 216 and/or to one or more struts 218 of the selected actuation element(s). In such embodiments, the stimulus can be applied to each of the different locations simultaneously or can be applied to different locations at different times (e.g., sequentially). As a result, the extent of the shape change can be modulated based on the number of locations at which the stimulus is applied. For example, applying a stimulus to a greater number of locations can produce a greater shape change, while applying a stimulus to a fewer number of locations can produce a smaller shape change.

It will be appreciated that the first and second actuation elements 208a-b can be configured in a number of different ways to allow for rotation-based actuation of the rotational control element 202. For example, although FIG. 2 illustrates the first and second actuation elements 208a-b as each having four apices 216 and three struts 218, in other embodiments the first and second actuation elements 208a-b can include a different number of apices (e.g., one, two, three, five, or more) and/or a different number of struts (e.g., one, two, four, five, or more). Additionally, although FIG. 2 illustrates the apices 216 as being curved and the struts 218 as being linear, in other embodiments the apices 216 and/or struts 218 can have other geometries (e.g., curved, linear, curvilinear, angular, etc.).

Figure 3:
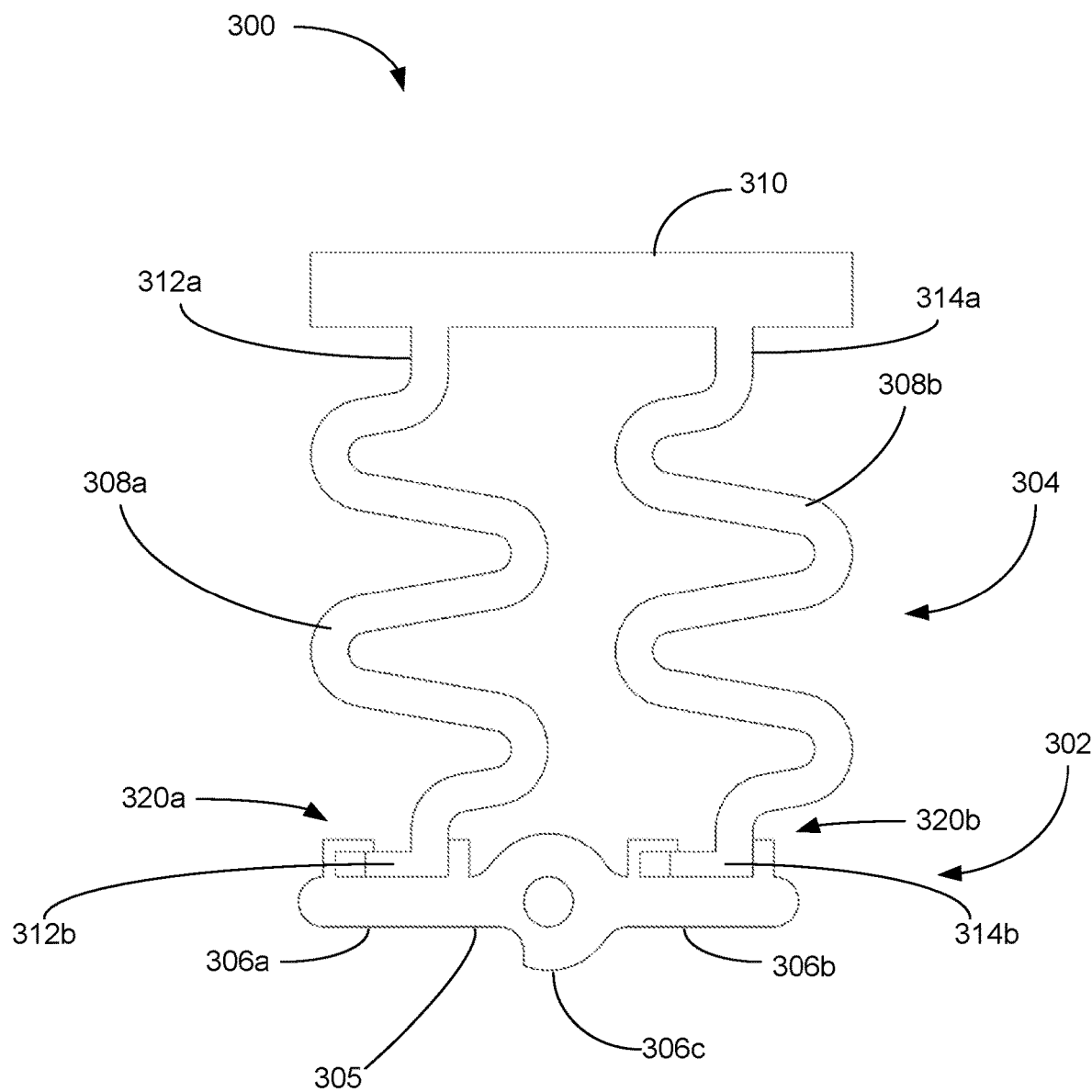
FIG. 3 is a front view of a flow control assembly of an intraocular shunting system configured in accordance with another embodiment of the present technology.

FIG. 3 is a front view of a flow control assembly 300 of an intraocular shunting system configured in accordance with another embodiment of the present technology. The flow control assembly 300 can be generally similar to the flow control assembly 200 described with respect to FIG. 2 such that like reference numbers (e.g., rotational control element 202 versus rotational control element 302) are used to identify similar or identical components. Accordingly, discussion of the flow control assembly 300 of FIG. 3 will be limited to those features that differ from the flow control assembly 200 of FIG. 2.

The flow control assembly 300 includes a rotational control element 302 having an elongated member 305 with a first end portion 306a, a second end portion 306b, and a cam portion 306c therebetween. The first and second end portions 306a-b can each include a respective retention feature (e.g., first retention feature 320a and second retention feature 320b) formed therein. The flow control assembly 300 further includes an actuation structure 304 having a first actuation element 308a and a second actuation element 308b. The first actuation element 308a can include a first end portion 312a coupled to the base support 310 and a second end portion 312b engaged with the first retention feature 320a. The second actuation element 308b can include a first end portion 314a coupled to the base support 310 and a second end portion 314b engaged with the second retention feature 320b. In some embodiments, the first and second retention features 320a-b each include a channel formed therein, and the second end portions 312b, 314b are each shaped to be received within the corresponding channel. The first and second retention features 320a-b can be sized larger than the respective second end portions 312b, 314b to permit the second end portions 312b, 314b to move therewithin. As the first and second actuation elements 308a-b change in shape (e.g., via the shape memory effect as described herein), the first and second end portions 312b, 314b can slide within their respective channels to rotatably move the rotational control element 302.

Figure 4A:
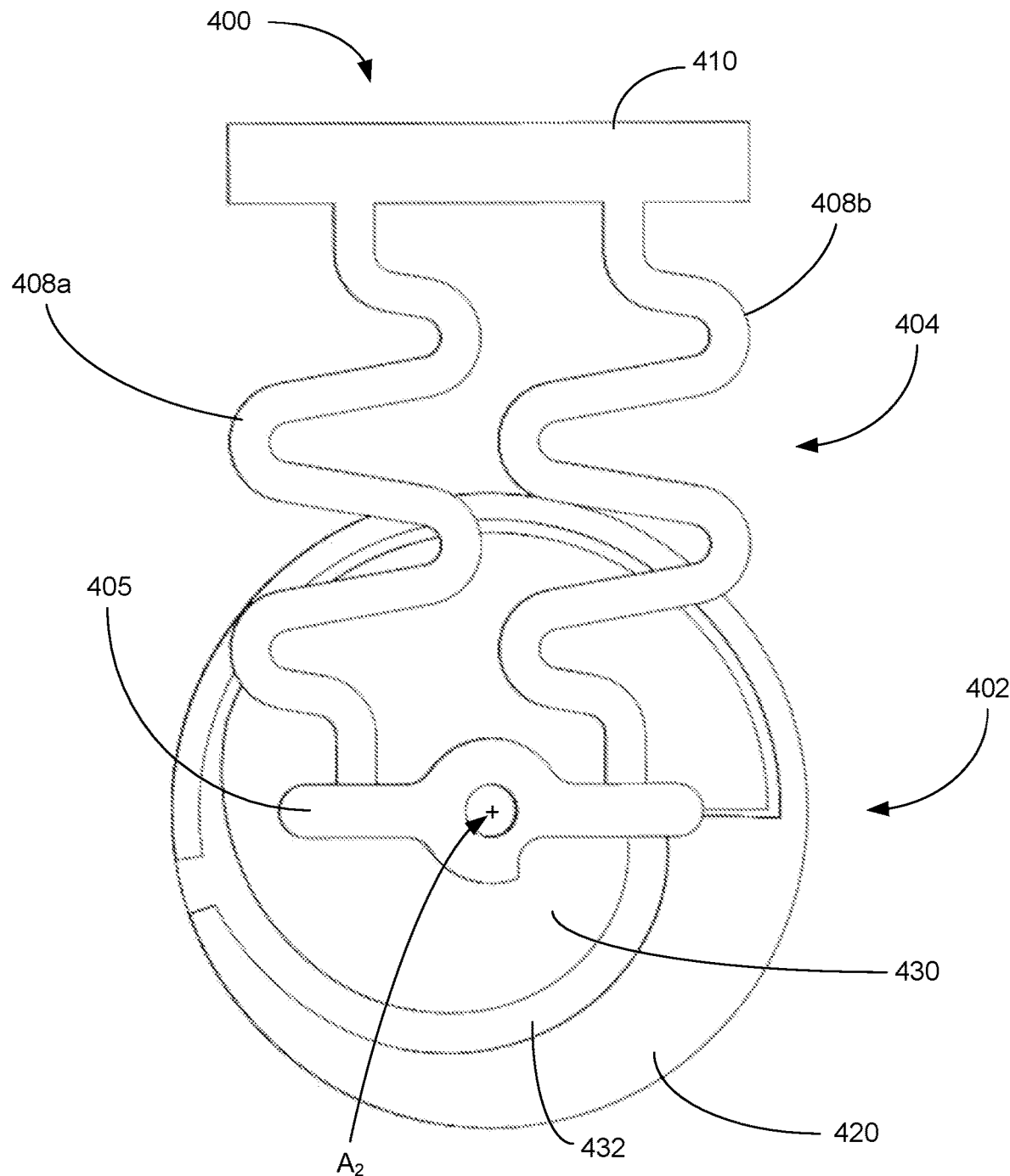
FIG. 4A is a front view of a flow control assembly of an intraocular shunting system configured in accordance with a further embodiment of the present technology.
Figure 4B:
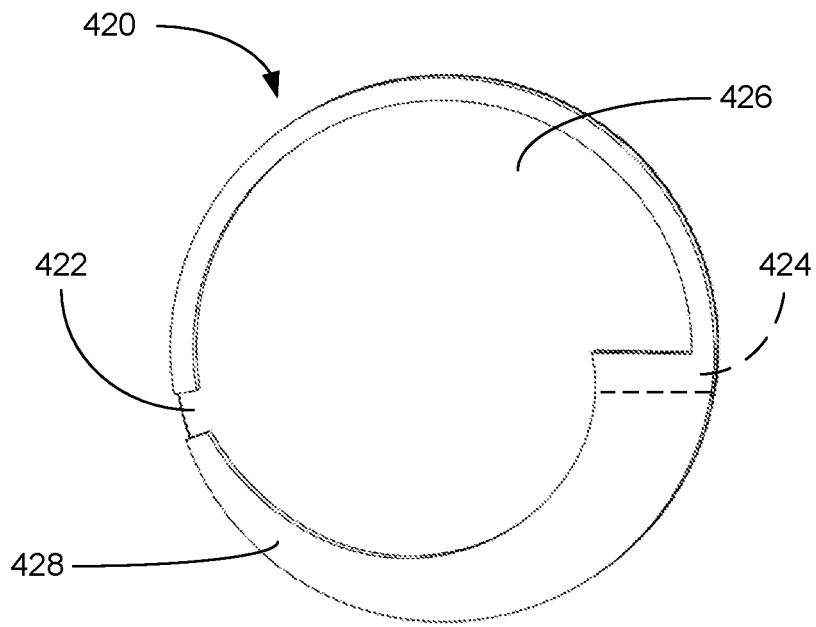
FIG. 4B is a front view of a first plate member of the assembly of FIG. 4A.
Figure 4C:
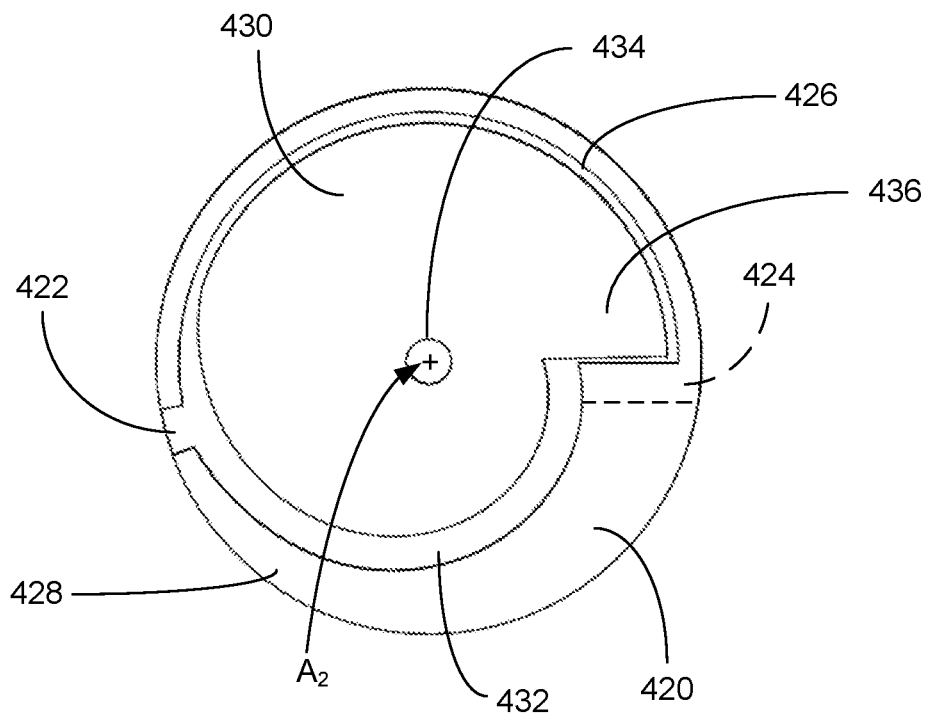
FIG. 4C is a front view of a second plate member positioned within the first plate member of the assembly of FIG. 4A.

FIGS. 4A-4C illustrate a flow control assembly 400 of an intraocular shunting system configured in accordance with a further embodiment of the present technology. More specifically, FIG. 4A is a front view of the assembly 400, FIG. 4B is a front view of a first plate member 420 of the assembly 400, and FIG. 4C is a front view of a second plate member 430 of the assembly 400 positioned within the first plate member 420.

Referring first to FIG. 4A, the flow control assembly 400 includes a rotational control element 402 coupled to an actuation structure 404. The rotational control element 402 can include an elongate member 405 configured to rotate to a plurality of different orientations (e.g., about a rotational axis $A_2$). The actuation structure 404 can include a first actuation element 408a and a second actuation element 408b coupled to the elongate member 405 and carried by a base support 410. The actuation structure 404 and elongate member 405 can be identical or generally similar to the corresponding components previously described with respect to FIGS. 2 and 3. Accordingly, discussion of the flow control assembly 400 of FIG. 4 will be limited to those features that differ from the embodiments of FIGS. 2 and 3.

Referring to FIGS. 4A-4C together, the rotational control element 402 further includes a first plate member 420 and a second plate member 430 configured to rotatably move relative to the first plate member 420. As best seen in FIG. 4B, the first plate member 420 can have a generally flattened shape and can include a flow inlet 422, a flow outlet 424, and a recessed portion 426 between the flow inlet 422 and the flow outlet 424. The flow inlet 422 and flow outlet 424 can each include one or more apertures, openings, ports, channels, etc. formed in a peripheral portion 428 of the first plate member 420 surrounding the recessed portion 426. The flow inlet 422 can be fluidly coupled to an outflow and/or inflow portion of a drainage element (e.g., for shunting fluid from the anterior chamber of the eye—not shown). The flow outlet 424 can be fluidly coupled to a location in the eye (e.g., a subconjunctival bleb space).

As best seen in FIG. 4C, the second plate member 430 can have a generally flattened shape and can be positioned within the recessed portion 426 of the first plate member 420. The positioning of the second plate member 430 within the recessed portion 426 can define a flow channel 432 fluidly coupling the flow inlet 422 and the flow outlet 424. For example, in the illustrated embodiment, the second plate member 430 is shaped similarly to the recessed portion 426 but has a smaller size (e.g., smaller surface area) such that the flow channel 432 is at least partially defined by the gap between the second plate member 430 and the peripheral portion 428 of the first plate member 430. In the illustrated embodiment, the gap extends around the entire periphery of the second plate member 430. In other embodiments the gap can extend only partially around the periphery of the second plate member 430.

The rotational control element 402 can be configured to control the amount of fluid flow through the flow channel 432 based on the orientation of the second plate member 430 relative to the first plate member 420. In some embodiments, the second plate member 430 can be configured to rotate about a rotational axis $A_2$ (e.g., in a clockwise and/or counterclockwise direction) relative to the first plate member 420. Optionally, the second plate member 430 can be rotatably coupled to the first plate member 420, such as by a fastener (e.g., a pin, screw, pivot, etc.—not shown) received within an aperture 434 formed in the second plate member 430.

The second plate member 430 can have a shape configured such that the geometry (e.g., size and/or shape) of the flow channel 432 changes as the second plate member 430 rotates. As a result, fluid flow through the flow channel 432 can be selectively adjusted by rotating the second plate member 430 to a plurality of different orientations. For example, rotation of the second plate member 430 can cause a cross-sectional area of the flow channel 432 to increase or decrease. As another example, rotation of the second plate member 432 can cause one or more portions of the flow channel 432 to become obstructed or unobstructed. As yet another example, rotation of the second plate member 430 can cause the flow inlet 422 and/or flow outlet 424 to become obstructed or unobstructed. In the illustrated embodiment, the second plate member 430 includes a protruding portion 436. When in a first orientation (e.g., as shown in FIG. 4C), the protruding portion 436 can be positioned away from the flow outlet 424, thus allowing fluid flow therethrough with little or no obstruction. When rotated to a second orientation (e.g., rotated clockwise), the protruding portion 436 can move near or adjacent the flow outlet 424 and/or into a portion of the flow channel 432 near the flow outlet 424, thereby partially or completely obstructing fluid flow through the flow outlet 424.

Referring again to FIG. 4A, the rotation of the second plate member 430 can be actuated by the actuation structure 404. In some embodiments, the second plate member 430 is coupled to the actuation structure 404 via elongated member 405. For example, the first and second actuation elements 408a-b can be coupled to the elongated member 405 to control the rotation thereof. The elongated member 405 can be coupled to the second plate member 430 such that rotation of the elongated member 405 produces a corresponding rotation of the second plate member 430 (e.g., in a clockwise or counterclockwise direction about rotational axis $A_2$). In other embodiments the elongated member 405 can be omitted such that the actuation structure 404 is directly coupled to the second plate member 430 to control the rotation thereof. The techniques by which the actuation structure 404 actuates the rotation of the elongated member 405 and/or second plate member 430 can be identical or generally similar to the embodiments previously described with respect to FIGS. 2 and 3. For example, the first and second actuation elements 408a-b can include shape memory materials configured to change in shape when heated to rotate the elongated member 405 and/or second plate member 430.

It will be appreciated that the flow control assembly 400 can be configured in a number of different ways. For example, although FIG. 4A-4C illustrate the first plate member 420 as having a generally circular shape, in other embodiments the first plate member 420 can have a different shape (e.g., elliptical, square, rectangular, polygonal, etc.). The shape of the second plate member 430 can also be varied as desired. Additionally, the geometry of the recessed portion 426 and/or second plate member 430 can be configured in a number of different ways to selectively modify the geometry and/or flow resistance characteristics of the flow channel 432. For example, in other embodiments the protruding portion 436 can be located near the flow inlet 422 instead of the flow outlet 424, or the second plate member 430 can include a plurality of protruding portions at different locations relative to the flow inlet 422, flow outlet 424, and/or flow channel 432.

Figure 5A:
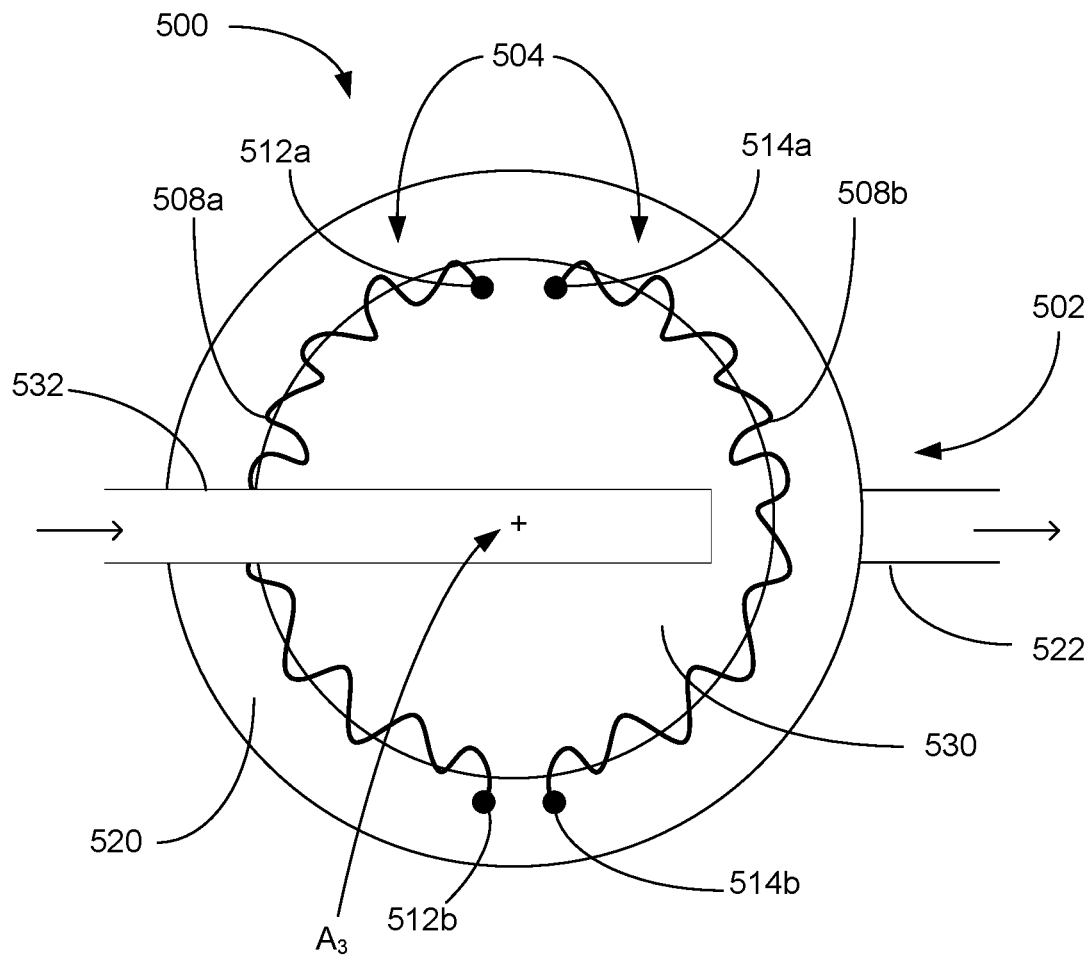
FIG. 5A is a top view of a flow control assembly of an intraocular shunting system configured in accordance with a further embodiment of the present technology.
Figure 5B:
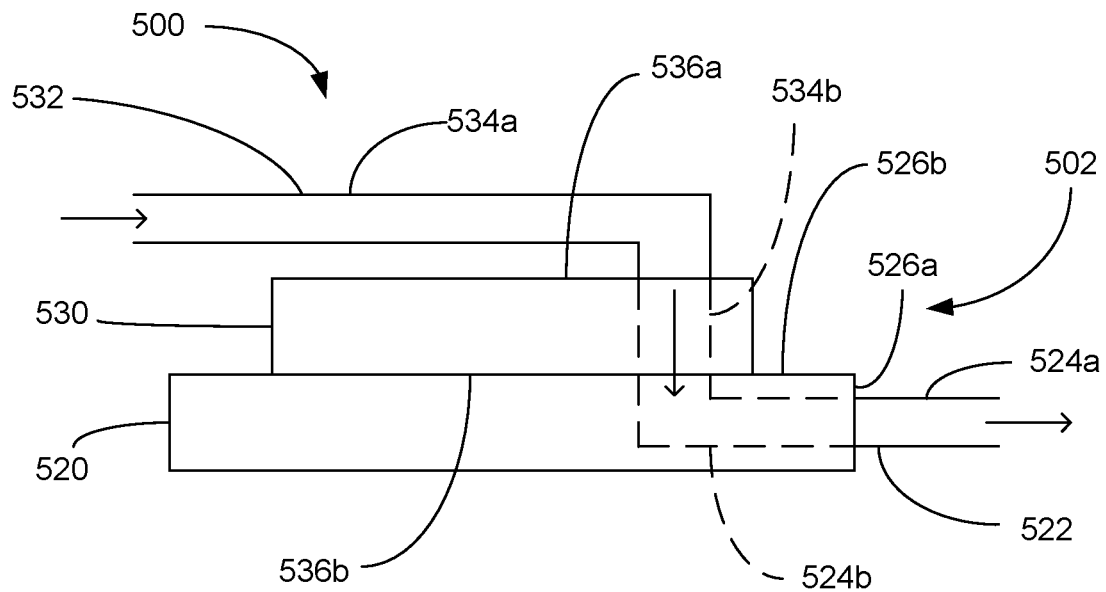
FIG. 5B is a side cross-sectional view of the assembly of FIG. 5A.

FIGS. 5A and 5B are a top view and a side cross-sectional view, respectively, of a flow control assembly 500 of an intraocular shunting system configured in accordance with a further embodiment of the present technology. Referring to FIGS. 5A and 5B together, the flow control assembly 500 includes a rotational control element 502 coupled to an actuation structure 504 (the actuation structure 504 is omitted from FIG. 5B merely for purposes of clarity). The rotational control element 502 can include a first plate member 520 coupled to a second plate member 530. The first plate member 520 can be positioned beneath the second plate member 530. The first and second plate members 520, 530 can each have a generally flattened shape (e.g., a circular, elliptical, square, rectangular, polygonal, or other shape). In the illustrated embodiment, the first and second plate members 520, 530 have the same shape but with different sizes (e.g., the first plate member 520 is larger than the second plate member 530). In other embodiments, the first and second plate members 520, 530 can have different shapes.

The first plate member 520 can include a first flow channel 522. The first flow channel 522 can be fluidly coupled to a location in the eye (e.g., a subconjunctival bleb space). As best seen in FIG. 5B, the first flow channel 522 can include an exterior section 524a located outside the first plate member 520 and an interior section 524b formed in the first plate member 520. In the illustrated embodiment, the exterior section 524a is coupled to a lateral surface 526a of the first plate member 520 and the interior section 524b extends through the first plate member 520 from the lateral surface 526a to an upper surface 526b of the first plate member 520. In other embodiments the exterior section 524a can be coupled to a different portion of the first plate member 520 (e.g., to a different lateral surface or a bottom surface) and the interior section 524b can extend through the first plate member 520 from that portion to the upper surface 526b. Alternatively, the exterior section 524a can be omitted, such that the first flow channel 522 only includes the interior section 524b.

The second plate member 530 can include a second flow channel 532. The second flow channel 532 can be fluidly coupled to an outflow portion of a drainage element (e.g., for shunting fluid from the anterior chamber of the eye—not shown). As best seen in FIG. 5B, the second flow channel 532 can include an exterior section 534a located outside the second plate member 530 and an interior section 534b formed in the second plate member 530. In the illustrated embodiment, the exterior section 534a is coupled to an upper surface 536a of the second plate member 530 and the interior section 534b extends through the second plate member 530 from the upper surface 536a to a lower surface 536b of the second plate member 530. In other embodiments the exterior section 534a can be coupled to a different portion of the second plate member 530 (e.g., to a lateral surface) and the interior section 534b can extend through the second plate member 530 from that portion to the lower surface 526b. Alternatively, the exterior section 534a can be omitted, such that the second flow channel 532 only includes the interior section 534b.

In some embodiments, the second plate member 530 is configured to rotatably move relative to the first plate member 520 (e.g., about rotational axis $A_3$) to change the position of the second flow channel 532 relative to the first flow channel 522. As a result, depending on the orientation of the second plate member 530 relative to the first plate member 520, the first and second flow channels 522, 532 can be aligned with each other (e.g., as shown in FIG. 5B) to permit fluid therethrough, or can be offset from each other to reduce or prevent fluid flow therethrough. For example, when the first and second flow channels 522, 532 are aligned, the interior section 524b of the first flow channel 522 can be aligned with and fluidly coupled to the interior section 534b of the second flow channel 532, thereby creating an unobstructed flow path permitting fluid flow therethrough. As a result, fluid can flow from a portion of the eye (e.g., the anterior chamber), through the second flow channel 532, through the first flow channel 522, and out to a different location of the eye. Conversely, when the first and second flow channel 522, 532 are offset from each other, the interior section 524b of the first flow channel 522 can be offset and fluidly decoupled from the interior section 534b of the second flow channel 532, thereby reducing or preventing fluid flow therethrough.

Referring again to FIG. 5A, the rotation of the second plate member 530 can be actuated by the actuation structure 504. The actuation structure 504 can include a first actuation element 508a and a second actuation element 508b. In the illustrated embodiment, the first and second actuation elements 508a-b each include respective first end portions 512a, 514a coupled to the second plate member 530 and respective second end portions 512b, 514b coupled to the first plate member 520. In other embodiments, the first end portions 512a, 514a can be coupled to the first plate member 520 and the second end portions 512b, 514b can be coupled to the second plate member 530. The first and second actuation elements 508a-b can each be elongated structures (e.g., struts, springs such as flat springs or helical springs wrapped around a guidewire, coils, wires, etc.) extending at least partially along the periphery of the second plate member 530. In the illustrated embodiment, the first and second actuation elements 508a-b are positioned at opposite peripheral portions of the second plate member 530.

In some embodiments, the first and second actuation elements 508a-b include one or more shape memory materials configured to at least partially transition from a first phase/state (e.g., a martensitic or intermediate state) to a second phase/state (e.g., an intermediate or austenitic state) upon application of energy, as previously described. The first and second actuation elements 208a-b can each be configured to change in shape or otherwise transform between a first configuration (e.g., a memory shape, a preferred geometry, etc.) and a second configuration (e.g., a shape different from the memory shape, a deformed geometry, etc.) via a shape memory effect (e.g., when heated) to drive the rotation of the second plate member 530. For example, in some embodiments, the memory shape is a lengthened configuration, while in other embodiments the memory shape is a shortened configuration.

For example, in the illustrated embodiment, the first actuation element 508a is configured to transform to a lengthened configuration when heated to rotate the second plate member 530 along a first direction (e.g., clockwise), and the second actuation element 508b is configured to transform to a lengthened configuration when heated to rotate the second plate member 530 along a second, opposite direction (e.g., counterclockwise). Alternatively or in combination, the first actuation element 508a can be configured to transform to a shortened configuration when heated to rotate the second plate member 530 along a first direction (e.g., counterclockwise), and the second actuation element 508b can be configured to transform to a lengthened configuration when heated to rotate the second plate member 530 along a second, opposite direction (e.g., clockwise). Optionally, the first and second actuation elements 508a-b can be configured to oppose each other, such that actuation of one actuation element via the shape memory effect produces a corresponding deflection and/or deformation in the other actuation element. For example, transformation of one actuation element into a lengthened configuration can cause the other actuation element to transform into a shortened configuration, and/or transformation of one actuation element into a shortened configuration can cause the other actuation element to transform into a lengthened configuration. The changes in shape of the first and second actuation elements 508a-b can drive the rotation of the first plate member 530 to control the alignment of the first and second flow channels 522, 532.

Figure 6A:
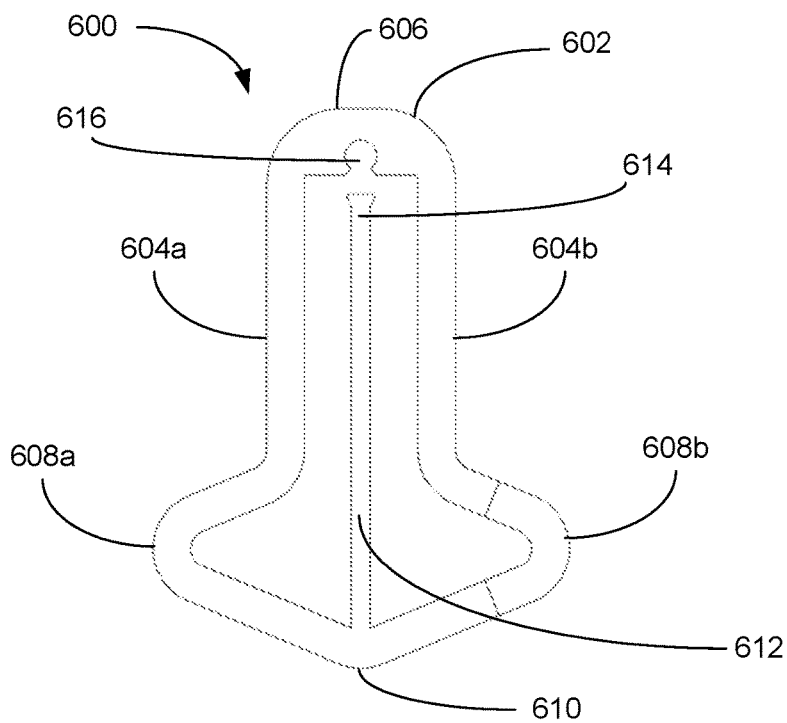
FIG. 6A is a flow control assembly of an intraocular shunting system configured in accordance with another embodiment of the present technology.
Figure 6B:
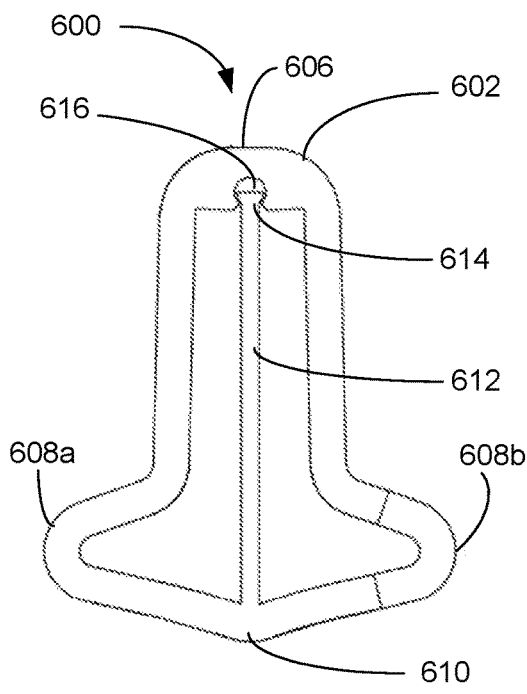
FIG. 6B is a front view of the assembly of FIG. 6A in a loaded and/or compressed configuration.
Figure 6C:
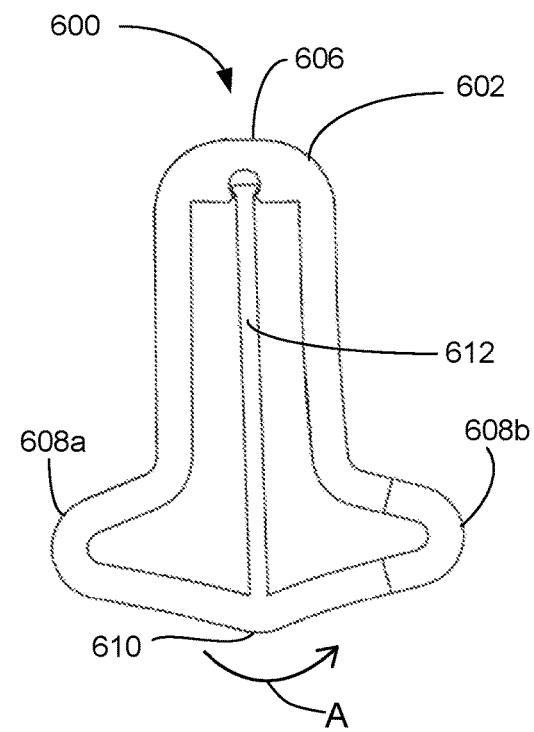
FIG. 6C is a front view of the assembly of FIG. 6B in a rotated configuration.

FIGS. 6A-6C illustrate a flow control assembly 600 of an intraocular shunting system configured in accordance with another embodiment of the present technology. More specifically, FIG. 6A is a front view of the assembly 600 in an unloaded and/or uncompressed configuration, FIG. 6B is a front view of the assembly 600 in a loaded and/or compressed configuration, and FIG. 6C is a front view of the assembly 600 in a rotated configuration.

Referring to FIGS. 6A-6C together, the flow control assembly 600 includes a frame structure 602. The frame structure 602 can include a first strut 604a and a second strut 604b coupled to each other by an upper segment 606. The first and second struts 604a-b can each have a generally linear shape. The first and second struts 604a-b can each extend along a longitudinal axis of the frame structure 602 and couple respectively to first and second curved segments 608a-b. The first and second curved segments 608a-b can be connected to each other by a base segment 610. The base segment 610 can be coupled to a pin element 612. The pin element 612 can be an elongated, generally linear structure that extends along the longitudinal axis of the frame structure 602 towards the upper segment 606 and terminates in an end portion 614. In some embodiments, the first and second struts 604a-b, upper segment 606, first and second curved segments 608a-b, base segment 610, and pin element 612 are integrally formed with each other such that the frame structure 602 is manufactured as a single unitary component. In other embodiments, one or more of the components of the frame structure 602 are manufactured separately and subsequently coupled to each other to form the frame structure 602.

The frame structure 602 can initially be in a fabricated or non-tensioned configuration (e.g., an unloaded and/or uncompressed configuration as shown in FIG. 6A) in which the pin element 612 is positioned away from the upper segment 606. The frame structure 602 can subsequently be placed into a tensioned configuration (e.g., a loaded and/or compressed configuration as shown in FIG. 6B) by moving the base segment 610 and pin element 612 towards the upper segment 606 until the end portion 614 of the pin element 612 is engaged with a retention feature 616 formed in the upper segment 606. For example, the retention feature 616 can be a notch, groove, aperture, or any other structure suitable for retaining end portion 614 therein. The end portion 614 of the pin element 612 can include a flange, lip, protrusion, or any other structure suitable for engaging the retention feature 616 to secure the pin element 612 thereto. In some embodiments, the frame structure 602 is manufactured in the non-tensioned configuration and subsequently placed into the tensioned configuration for use (e.g., prior to, concurrently with, or after implantation in the patient's eye).

In some embodiments, the base segment 610 serves as a rotational control element for selectively controlling fluid flow through a drainage element (e.g., for shunting fluid from the anterior chamber of the eye—not shown). For example, the base segment 610 can be positioned near or adjacent to one or more apertures of an outflow or inflow portion of the drainage element (not shown). When in a first orientation (e.g., as shown in FIG. 6B), the base segment 610 can partially or completely cover the aperture(s) to partially or completely obstruct fluid flow therefrom. When rotated to a second orientation (e.g., along a counterclockwise direction as shown in FIG. 6C), the base segment 610 can be spaced apart from the aperture(s) to permit fluid flow therefrom with little or no obstruction.

The first curved segment 608a and/or second curved segment 608b can serve as an actuation structure for rotating the base segment 610 to selectively adjust fluid flow. In the illustrated embodiment, for example, the second curved segment 608b is made from one or more shape memory materials configured to at least partially transition from a first phase/state (e.g., a martensitic or intermediate state) to a second phase/state (e.g., an intermediate or austenitic state) upon application of energy, as previously described. When the energy is applied, the second curved segment 608b can undergo a phase transition causing it to stiffen and/or change in shape to a contracted configuration. As a result, the base segment 610 can rotate/pivot along a counterclockwise direction towards the second curved segment 608b, e.g., as shown in FIG. 6C and indicated by arrow A. Optionally, in some embodiments, the first curved segment 608a is also made from a shape memory material configured to actuate rotation of the base segment 610. When energy is applied to the first curved segment 608a, it can stiffen and/or change in shape to a contracted configuration, thus causing the base segment 610 to rotate/pivot along a clockwise direction towards the first curved segment 608a. As a result, the first and second curved segments 608a-b can oppose each other to allow the base segment 610 to be rotated/pivoted in two opposite directions.

Figure 7A:
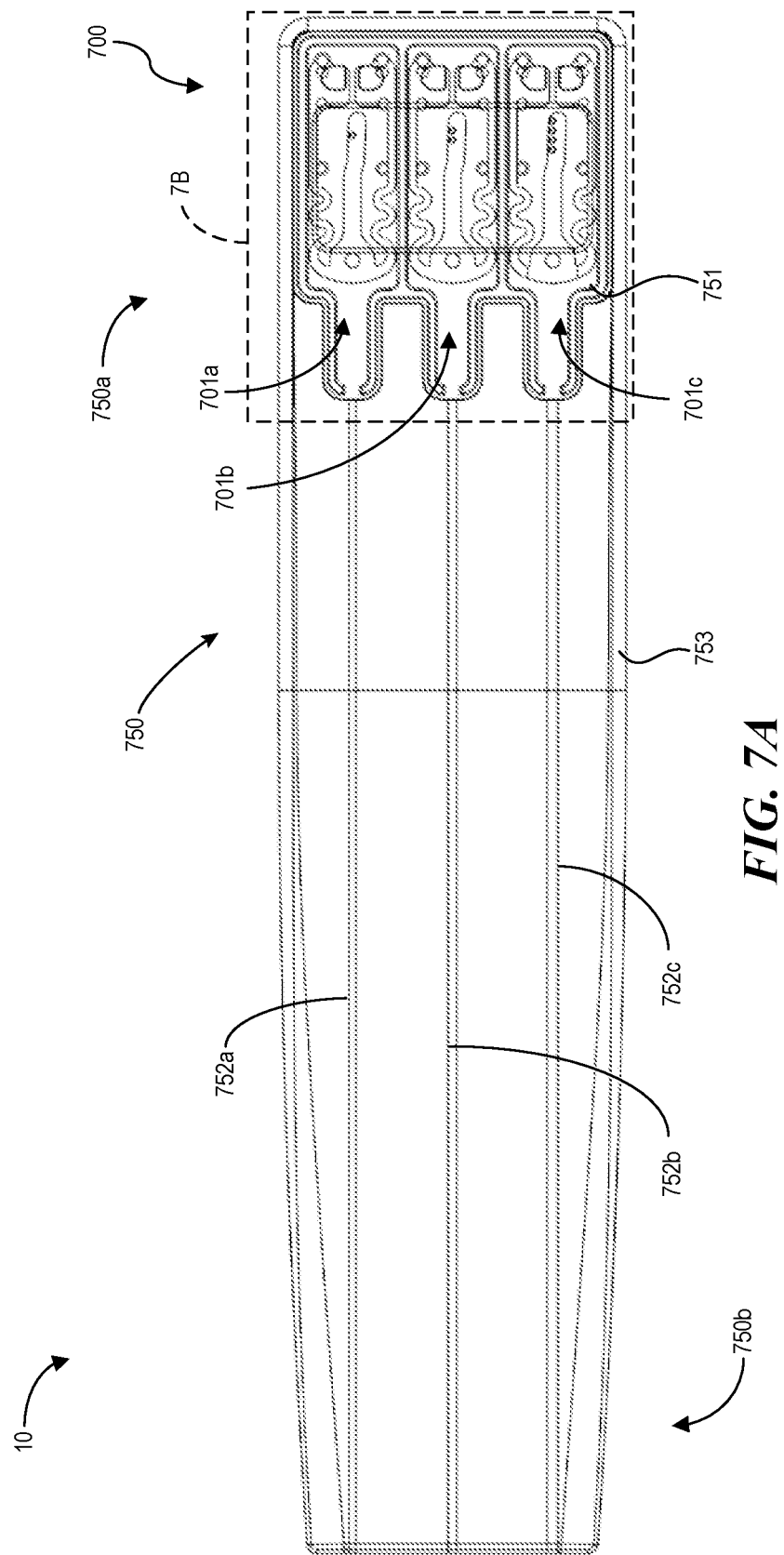
FIG. 7A is a front view of an intraocular shunting system configured in accordance with select embodiments of the present technology.
Figure 7B:
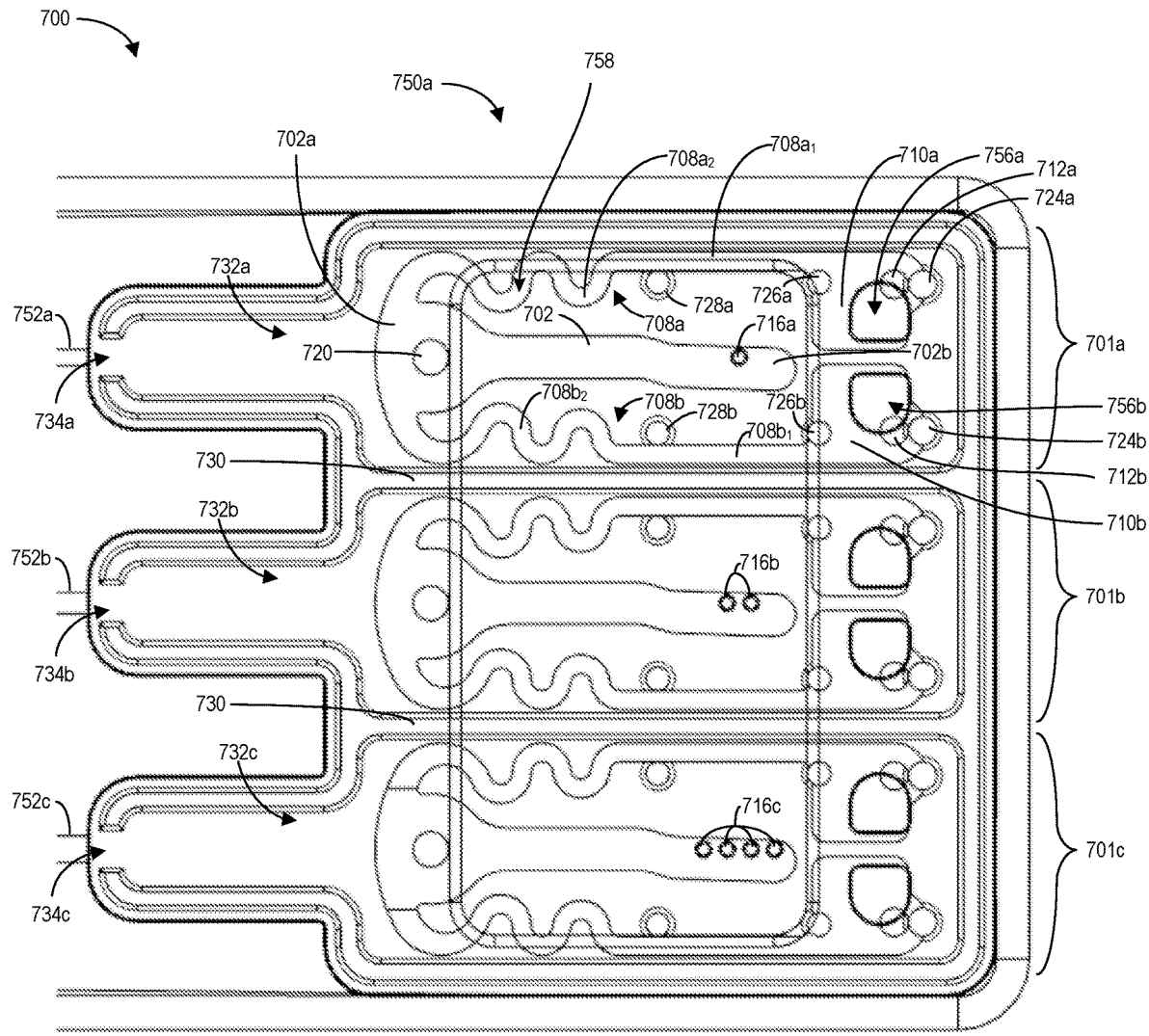
FIG. 7B is an enlarged view of a flow control assembly of the intraocular shunting system shown in FIG. 7A.
Figure 7C:
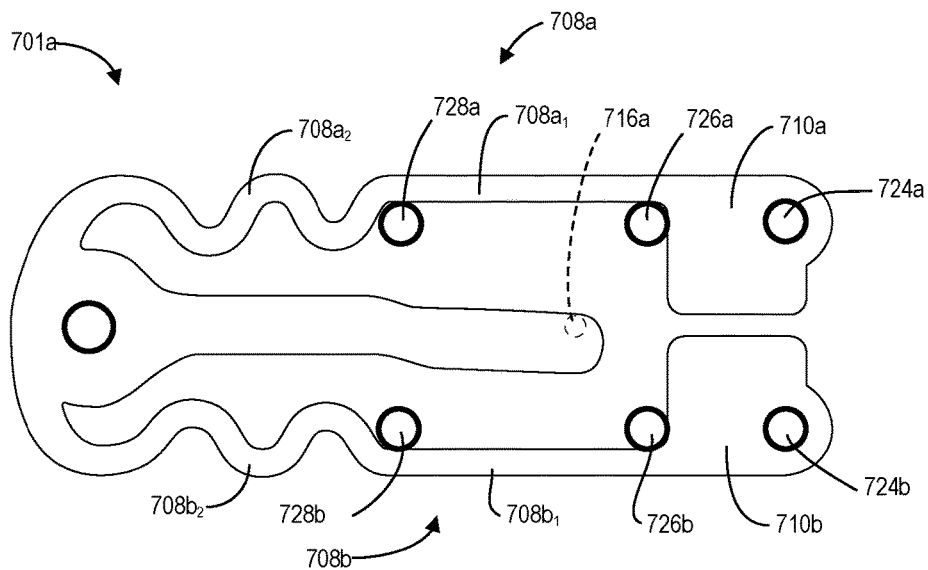
FIG. 7C is an enlarged view of a portion of the flow control assembly shown in FIG. 7B.
Figure 7D:
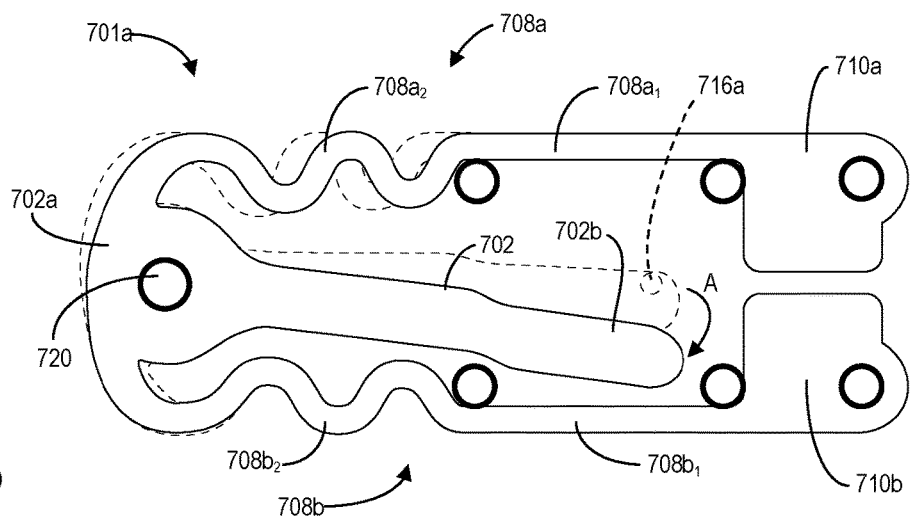
FIG. 7D is an enlarged view of an actuation assembly of the intraocular shunting system of FIG. 7A in a first configuration.
Figure 7E:
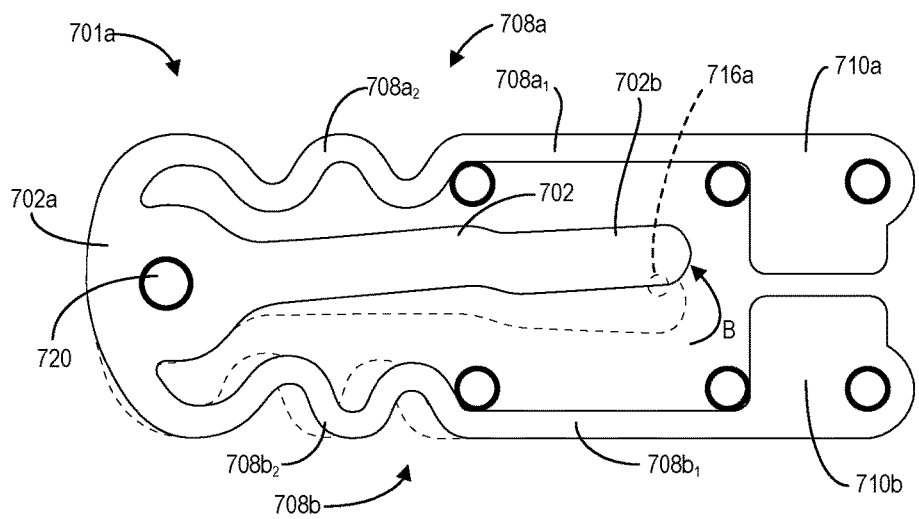
FIG. 7E is an enlarged front view of the actuation assembly of FIG. 7D in a second configuration.

FIGS. 7A-7E illustrate an intraocular shunting system 10 (the "system 10") configured in accordance with select embodiments of the present technology. More specifically, FIG. 7A is a front view of the system 10, FIG. 7B is an enlarged front view of a flow control assembly 700 of the system 10 taken from the region identified in FIG. 7A, FIG. 7C is an enlarged front view of an actuator 701a of the flow control assembly 700, FIG. 7D is an enlarged front view of the actuator 701 in a first configuration, and FIG. 7E is an enlarged front view of the actuator 701 in a second, different configuration.

Referring first to FIG. 7A, the system 10 includes a flow control assembly 700 and a casing, plate, or drainage element 750. The drainage element 750 can extend between a first end portion 750a and a second end portion 750b, and can have a generally flat profile. When implanted in a patient's eye, the first end portion 750a can reside at least partially within an interior region of the eye (e.g., the anterior chamber), and the second end portion 750b can reside at least partially within and/or be in fluid communication with a desired outflow location (e.g., a subconjunctival bleb space).

In some embodiments, the drainage element 750 can include multiple discrete components. For example, the drainage element 750 may include a generally rigid inner structure 751 (e.g., a plastic or other rigid block, plate, etc.) that encases or is configured to encase the flow control assembly 700 and is positioned at the first end portion 750a of the drainage element 750. The drainage element 750 may further include a semi-flexible outer structure 753 (e.g., a silicone or other flexible shell, casing, etc.) that holds the first inner structure and extends between the first end portion 750a and the second end portion 750b of the drainage element 750. For example, the generally rigid inner structure 751 can have a length between about 1 mm to about 5 mm, such as between about 2 mm and 3 mm, and the semi-flexible outer structure 753 may have a length between about 6 mm and about 13 mm, such as between about 8 mm and 10 mm. In such embodiments, the generally rigid inner structure 751 may form a fluid seal with the semi-flexible outer structure 753 to prevent fluid from leaking therebetween.

The drainage element 750 can have a plurality of lumens or channels extending between the first end portion 750a and the second end portion 750b. In the illustrated embodiment, for example, the drainage element 750 includes a first channel 752a, a second channel 752b, and a third channel 752c (collectively referred to herein as the channels 752). As described in greater detail below, aqueous can drain through the channels 752 from the anterior chamber to the desired outflow location when the system 10 is implanted in the patient's eye. The channels 752 can have the same or different cross-sectional dimensions and/or areas. For example, in some embodiments the first channel 752a has a first diameter, the second channel 752b has a second diameter greater than the first diameter, and the third channel 752c has a third diameter greater than the second diameter. In embodiments in which the channels 752 have different dimensions (e.g., diameters), the fluid resistance through each of the channels 752 may be different. Although shown as having three channels 752, the system 10 can include more or fewer channels 752, such as one, two, four, five, six, seven, eight, or more.

As described in greater detail with respect to FIG. 7B, the flow control assembly 700 can include one or more actuators for controlling the flow of aqueous into the channels 752. For example, the flow control assembly 700 can include a first actuator 701a for controlling the flow of aqueous through the first channel 752a, a second actuator 701b for controlling the flow of aqueous through the second channel 752b, and a third actuator 701c for controlling the flow of aqueous through the third channel 752c (collectively referred to as the actuators 701). Although shown as having three actuators 701, the system 10 can include more or fewer actuators 701, such as one, two, four, five, six, seven, eight, or more. In some embodiments, the number of actuators 701 can be same as the number of channels 752, although in other embodiments the system 10 can have a different number of actuators 701 and channels 752. In some embodiments, the system 10 includes a single actuator 701 for controlling flow through a single channel extending through a drainage element.

Referring now to FIG. 7B, the actuators 701 are positioned in respective chambers defined by the drainage element 750 and one or more internal wall structures 730 (e.g., which may be part of the generally rigid inner structure 751). For example, the first actuator 701a is positioned in a first chamber 732a, the second actuator 701b is positioned in a second chamber 732b, and the third actuator 701c is positioned in a third chamber 732c (collectively referred to herein as chambers 732). The first chamber 732a can be in fluid communication with the first channel 752a (e.g., via a first port 734a), the second chamber 732b can be in fluid communication with the second channel 752b (e.g., via a second port 734b), and the third chamber 732c can be in fluid communication with the third channel 752c (e.g., via a third port 734c). In some embodiments, the chambers 732 can be fluidly isolated from one another to prevent fluid from flowing between the chambers 732. As provided below, fluidly isolating the chambers 732 enables the system 10 to provide a more titratable/granular therapy by enabling a healthcare provider to select between a plurality of therapy levels.

The drainage element 750 can include a first fluid inlet 716a (shown as a single aperture 716a) that in at least some configurations can fluidly connect the first chamber 732a to an environment external to the first end portion 750a of the drainage element 750. The drainage element 750 can further include a second fluid inlet 716b (shown as two apertures) that in at least some configurations can fluidly connect the second chamber 732b to the environment external to the first end portion 750a of the drainage element 750. The drainage element 750 can further include a third fluid inlet 716c (shown as four apertures 716c) that in at least some configurations can fluidly connect the third chamber 732c to the environment external to the first end portion 750a of the drainage element 750. When the system 10 is implanted in the eye, the environment external to the first end portion 750a of the drainage element 750 can include the anterior chamber of the eye. Accordingly, in at least some configurations, aqueous can flow into the chambers 732 via the respective fluid inlets in the drainage element 750. The aqueous can then drain from the chambers 732 via the respective channels 752. As described in greater detail below, the fluid resistance of the system 10, and thus the drainage of aqueous through the system 10, can be selectively controlled by selectively blocking and/or unblocking the fluid inlets 716 by selectively actuating the actuators 701.

The drainage element 750 can also include a first transmission region 756a and a second transmission region 756b (collectively referred to as transmission regions 756). In some embodiment, the transmission regions 756 can have a lower absorbance than the surrounding structure such that energy (e.g., light, laser energy, etc.) can pass through the transmission region with relatively less absorbance or deflection. In some embodiments, the transmission regions 756 can be a different material and/or different properties than the surrounding structure. In some embodiments, the transmission regions 756 are composed of the same material as the surrounding structure, but nevertheless provide a target for a user to direct energy toward. In some embodiments, the transmission regions 756 are an opening in the drainage element 750. When the first actuator 701a is secured to the drainage element 750, target regions on the first actuator 701a align with the transmission regions 756, as described below. This enables energy delivered from a source external to the drainage element 750 to pass through the transmission regions 756 and energize (e.g., heat) the targets.

The drainage element 750 can further include a window 758. The window 758 may be composed of a transparent or semi-transparent material that permits a user (e.g., a physician) to visualize the orientation of the actuators 701. In some embodiments, the window 758 may align with the target regions of the actuators 701, and the transmission regions 756 can be omitted. In embodiments in which the drainage element 750 includes the generally rigid inner structure 751 and the semi-flexible outer structure 753, the window 758 may be an opening in the semi-flexible outer structure 753, and the fluid inlets 716 may be in the generally rigid inner structure 751.

The first actuator 701a includes a projection 702 (e.g., a finger, a tongue, a lever, a gating element, a control element, etc.), a first actuation element 708a, a second actuation element 708b, a first target 710a, and a second target 710b. The first actuation element 708a extends between the first target 710a and a proximal region 702a of the projection 702, and the second actuation element 708b extends between the second target 710b and the proximal region 702a of the projection 702. The projection 702 extends from the proximal region 702a to a distal region 702b configured to interface with the first fluid inlet 716a to control the flow of fluid therethrough. In the illustrated embodiment, the projection 702 extends toward the first target 710a and the second target 710b (e.g., the distal region 702b is between the proximal region 702a and the first and second targets). In other embodiments, the projection 702 extends away from the first target 710a and the second target 710b (e.g., the proximal region 702a is between the distal region 702b and the first and second targets). In such embodiments, the first fluid inlet 716a would also be positioned distally (e.g., closer to the first port 734a and the first channel 752a) such that the distal region 702b still is configured to interface with the first fluid inlet 716a. Regardless of its orientation, the distal region 702b of the projection is a free end (e.g., it is not connected to another portion of the first actuator 701a or other portion of the system 700) such that it can pivotably/rotatably move relative to the drainage element 750 and the first fluid inlet 716a, as described in greater detail below. In some embodiments, the first actuation element 708a and the second actuation element 708b are connected via a connector region. In such embodiments, the projection 702 can extend from the connector region. The connector region can be contiguous with the first actuation element 708a, the second actuation element 708b, and/or the projection 702, or can be a separate element coupled to the first actuation element 708a, the second actuation element 708b, and/or the projection 702 via suitable connection techniques.

The first actuator 701a can be secured to or otherwise at least partially restrained relative to the drainage element 750. For example, in the illustrated embodiment, the proximal region 702a of the projection 702 is pivotably/rotatably secured to the drainage element 750 via a restraint 720 (e.g., an anchor, pin, etc.) such that the projection 702 can pivot/rotate relative to the drainage element 750. Accordingly, the projection 702 can also be referred to as a rotational control element. In some embodiments, the proximal region 702a can include an aperture (not shown) through which the restraint 720 can be inserted to facilitate coupling of the proximal region 702a to the drainage element 750 via the restraint 720.

The first target 710a is secured to drainage element 750 via a first target first restraint 724a (e.g., an anchor, pin, etc.) and a corresponding first aperture 712a in the first target 710a. The first target first restraint 724a and the first aperture 712a are shown as decoupled in FIG. 7B to more clearly illustrate both components. However, as shown in FIG. 7C—which illustrates the first actuator 701a and select restraints with the other features of the system 10 omitted for clarity—the first target first restraint 724a is configured to extend through the first aperture 712a (not visible in FIG. 7C) to secure the first target 710a to the drainage element 750. Accordingly, securing the first actuator 701a to the drainage element 750 therefore includes deforming it (e.g., stretching it) relative to its preferred or fabricated geometry such that the first aperture 712a aligns with the first target first restraint 724a, and securing it to the drainage element using one or more pins or anchors. As described in greater detail below, this deformation tensions the first actuation element 708a and prepares it to undergo a geometric change when the first target 710a is heated. The second target 710b is also secured to the drainage element 750 via a second target first restraint 724b and a corresponding second aperture 712b in the second target 710b. The second target first restraint 724b and the second aperture 712b are shown as decoupled in FIG. 7B to more clearly illustrate both components. However, as shown in FIG. 7C, the second target first restraint 724b is configured to extend through the second aperture 712b (not visible in FIG. 7C) to secure the second target 710b to the drainage element 750. Accordingly, securing the first actuator 701a to the drainage element 750 therefore includes deforming it (e.g., stretching it) relative to its preferred or fabricated geometry such that the second aperture 712b aligns with the second target first restraint 724b, and securing it to the drainage element 750 using one or more pins or anchors. As described in greater detail below, this deformation tensions the second actuation element 708b and prepares it to undergo a geometric change when the second target 710b is heated.

Accordingly, in the illustrated embodiment, the first actuator 701a is anchored to the drainage element 750 in at least three locations/regions (e.g., at the first target 710a, at the second target 710b, and at the proximal region 702a of the projection 702). Without being bound by theory, anchoring the first actuator 701a to the drainage element 750 at three locations or regions permits the first actuator 701a to operate via a pivoting motion that, as described below, can translate a relatively small movement of a first portion of the actuator (e.g., the first actuation element 708a) into a relatively large movement of a second portion of the actuator (e.g., the distal region 702b of the projection 702). Anchoring the first actuator 701a at three locations also permits the first target 710a and the second target 710b to be substantially thermally isolated (as opposed to if the first target 710a and the second target 710b were directly connected and anchored at a single location), which enables the first actuation element 708a and the second actuation element 708b to be selectively and independently actuated. In other embodiments, the first actuator 701a can be anchored to the drainage element 750 at fewer or more positions, such as one, two, four, five, six, seven, eight, or more locations. Moreover, although shown as being anchored by first and second restraints 724, 726, the first and second targets 710a, 710b can be anchored via other suitable means. For example, in some embodiments the first and second targets 710a, 710b can be connected to an interior surface of the drainage element 750 via an adhesive (e.g., glue, tape, staple, etc.).

As best shown in FIG. 7C, the first target 710a can also be at least partially restrained by a first target second restraint 726a, and the second target 710b can also be at least partially restrained by a second target second restraint 726b. The first target second restraint 726a does not necessarily directly couple the first actuator 701a to the drainage element 750, but rather reduces or prevents the first target 710a and/or the second actuation element 708a from rotating or bending inwardly toward the projection 702. Likewise, the second target second restraint 726b does not necessarily directly couple the first actuator 701a to the drainage element 750, but rather reduces or prevents the second target 710b from rotating or bending inwardly toward the projection 702.

In some embodiments, the first actuation element 708a may optionally be at least partially restrained by a first actuation element restraint 728a, and the second actuation element 708b may optionally be at least partially restrained by a second actuation element restraint 728b. Like the first target second restraint 726a, the first actuation element restraint 728a does not necessarily directly couple the first actuation element 708a to the drainage element 750, but nevertheless can prevent or reduce the first actuation element 708a from bowing or otherwise migrating inwardly toward the projection 702. Likewise, the second actuation element restraint 728b does not necessarily directly couple the second actuation element 708b to the drainage element 750, but nevertheless can prevent or reduce the second actuation element 708b from bowing or otherwise migrating inwardly toward the projection 702. As a result of the first actuation element restraint 728a, the first actuation element 708a includes a first (e.g., generally linear) region $708a_1$ extending from the first target 710a and a second (e.g., non-linear or curved region) $708a_2$ extending between the first region $708a_1$ and the projection 702. Likewise, as a result of the second actuation element restraint 728b, the second actuation element 708b includes a first (e.g., generally linear) region $708b_1$ extending from the second target 710b and a second (e.g., non-linear or curved region) region $708b_2$ extending between the first region $708b_1$ and the projection 702. The first actuation element 708a and the second actuation element 708b may also be at least partially constrained by the walls 730 shown in FIG. 7B (e.g., preventing external bending or flexion of the first region $708a_1$ and the first region $708b_1$). By at least partially constraining the actuation elements 708 from flexing inwardly or outwardly in the first regions $708a_1$, $708b1$, more of the strain in the actuator 701a is translated into a larger displacement of the projection 702 during actuation of the first actuator 701a, described below.

The first actuation element 708a and the second actuation element 708b generally act in opposition. For example, as described in greater detail below, the first actuation element 708a can be actuated to rotate the projection 702 in a first direction (e.g., clockwise) to change (e.g., decrease) the fluid resistance through the first fluid inlet 716a (e.g., by unblocking, at least partially unblocking, or further unblocking the first fluid inlet 716a). The second actuation element 708b can be actuated to rotate the projection 702 in a second direction (e.g., counterclockwise) generally opposite the first direction to change (e.g., increase) the fluid resistance through the first fluid inlet 716b (e.g., by blocking, further blocking, and/or interfering with the first fluid inlet 716a).

To facilitate the foregoing movement of the projection 702, the first actuator 701a can be composed at least partially of a shape memory material or alloy (e.g., nitinol). Accordingly, the first actuator 701a (and/or select regions thereof) can be transitionable at least between a first material phase or state (e.g., a martensitic state, a R-phase, a composite state between martensitic and R-phase, etc.) and a second material phase or state (e.g., an austenitic state, an R-phase state, a composite state between austenitic and R-phase, etc.). In the first material state, the first actuator 701a or select region thereof may be deformable (e.g., plastic, malleable, compressible, expandable, etc.). In the second material state, the first actuator 701a or select region thereof may have a preference toward a specific preferred geometry (e.g., original geometry, manufactured or fabricated geometry, heat set geometry, etc.). As described in greater detail below, select regions of the first actuator 701a can be transitioned between the first material state and the second material state by applying energy (e.g., heat) to the first actuator 701a to heat the assembly above a transition temperature. In some embodiments, the transition temperature is a temperature greater than an average body temperature (e.g., an average temperature in a human eye).

In some embodiments, the first actuation element 708a and the second actuation element 708b of the first actuator 701a can be selectively and independently actuated (e.g., transitioned between the first material state and the second material state). For example, to actuate the first actuation element 708a, heat/energy can be applied to the first target 710a, such as from an energy source positioned external to the patient's eye (e.g., a laser). The heat applied to the first target 710a spreads through at least a portion of the first actuation element 708a, which can heat the first actuation element 708a above its transition temperature. To actuate the second actuation element 708b heat/energy can be applied to the second target 710b. The heat applied to the second target 710b spreads through the second actuation element 708b, which can heat at least the portion of the second actuation element 708b above its transition temperature.

FIGS. 7D and 7E illustrate the first actuator 701a after actuation of the first actuation element 708a and the second actuation element 708b, respectively. If the first actuation element 708a is deformed relative to its preferred geometry (e.g., as shown in FIG. 7B), actuating the first actuation element 708a causes the first actuation element 708a to move toward its preferred geometry. For example, if the first actuation element 708a is stretched (e.g., tensioned) relative to its preferred geometry, actuating the first actuation element 708a causes it to contract (e.g., shorten). The contraction of the first actuation element 708a generally occurs in the second non-linear region $708a_2$ because the first generally linear region 708a₁ is held in place via one or more restraints (e.g., the first actuation element restraint 728a). Additionally, because the first actuator 701a is rotatably coupled to the drainage element 750 at the restraint 720, contracting the first actuation element 708a induces a rotational motion in the projection 702. In particular, the distal region 702b of the projection 702 is rotated in a clockwise direction (as shown by arrow A) toward the second actuation element 708b. This can transition the projection 702 from a first position in which it confers a first fluid resistance through the first fluid inlet 716a to and/or toward a second position in which it confers a second fluid resistance through the first fluid inlet 716b that is less than the first fluid resistance. For example, the projection 702 may block or substantially block the first fluid inlet 716a in the first position, and unblock or at least partially unblock the first fluid inlet 716a in the second position. Following actuation of the first actuation element 708a, the projection 702 may recoil (e.g., rotate in a counterclockwise direction) at least slightly toward the first position, but nevertheless remains rotated downwardly relative to the first position such that the first fluid inlet 716a remains at least partially unblocked. In other embodiments, the projection 702 remains in the second position without exhibiting substantial recoil. In addition to moving the projection 702 toward the second actuation element 708b, actuating the first actuation element 708a can also induce a corresponding deformation (e.g., stretching, lengthening, tensioning, etc.) in the second actuation element 708b, which remains in the first material state and thus is generally malleable (e.g., actuating the first actuation element 708a decreases strain in the first actuation element 708a and increases strain in the second actuation element 708b).

The operation can be reversed by actuating the second actuation element 708b, causing it to contract (e.g., shorten) toward its preferred geometry, as shown in FIG. 7E. The contraction of the second actuation element 708b predominantly occurs in the second non-linear region 708b₂ because the first generally linear region 708b₁ is held in place via one or more restraints (e.g., the second actuation element restraint 728b). Because the first actuator 701a is rotatably secured at restraint 720, contracting the second actuation element 708b induces a rotational motion in the projection 702. In particular, the distal region 702b of the projection 702 is rotated in a counterclockwise direction (as shown by arrow B) toward the first actuation element 708a. This can transition the projection 702 from the second position conferring the second relatively lower fluid resistance through the first fluid inlet 716a to and or toward the first position conferring the first relatively higher fluid resistance through the first fluid inlet 716a. In some embodiments, the projection 702 may rotate in a counterclockwise direction to a third position between the first fluid inlet 716a and the first actuation element 708a when the second actuation element 708b is actuated. Accordingly, in some embodiments the system 10 includes a mechanical or other stopping feature that is configured to prevent the projection 702 from rotating too far in the counterclockwise direction, which may cause the projection 702 to not block the first fluid inlet 716a upon actuation of the second target 710b. The mechanical stop can be configured to stop counterclockwise rotation of the projection 702 once the projection 702 blocks or substantially blocks the first fluid inlet 716a following actuation of the second actuation element 708b.

Accordingly, the first actuation element 708a and the second actuation element 708b can be selectively and independently actuated to block or unblock the first fluid inlet 716a to control the flow of fluid therethrough. In some embodiments, the projection 702 can be moved to any number of positions between fully blocking and fully unblocking the first fluid inlet 716a to provide a variety of different outflow resistance levels by incrementally adjusting the projection 702 relative to the first fluid inlet 716a. Additional details regarding the operation of shape memory actuators are described in U.S. Patent Publication No. 2020/0229982 and International Patent Application Nos. PCT/US20/55144 and PCT/US20/55141, the disclosures of which are incorporated by reference in their entireties.

In some embodiments, the first actuator 701a can be a unitary or integral structure (e.g., fabricated from a single piece of material, fabricated using a vapor deposition process, etc.). To assemble the flow control assembly 700, the first actuator 701a can be tensioned (e.g., stretched, lengthened, expanded, etc.) and secured to the drainage element 750 via the restraints while in the first material state. This at least partially deforms the actuation elements 708 relative to their preferred geometries. For example, as described above, both the first actuation element 708a and the second actuation element 708b are stretched (e.g., lengthened) relative to their preferred geometries when loaded onto the drainage element 750. In other embodiments, the first actuator 701a can be compressed and secured to the drainage element 750, rather than tensioned.

Although the foregoing description is directed to the first actuator 701a, the description can also apply to the second actuator 701b and/or the third actuator 701c. Accordingly, the second actuator 701b and/or the third actuator 701c can be the same as, or at least substantially similar to, the first actuator 701a. The drainage of aqueous through the system 10 can therefore be selectively controlled by selectively blocking and/or unblocking the fluid inlets 716 using the actuators 701. For example, to provide a first level of therapy having a first drainage rate and a first flow resistance, the first fluid inlet 716a can be accessible/unblocked, while the second fluid inlet 716b and the third fluid inlet 716c remain inaccessible/blocked. To provide a second level of therapy having a second drainage rate that is greater than the first drainage rate (e.g., a second flow resistance less than the first flow resistance), the second fluid inlet 716b can be accessible/unblocked, while the first fluid inlet 716a and the third fluid inlet 716c remain inaccessible/blocked. To provide a third level of therapy having a third drainage rate greater than the second drainage rate (e.g., a third flow resistance less than the first flow resistance), the first fluid inlet 716a and the second fluid inlet 716b can be unblocked while the third fluid inlet 716c remains blocked. As one skilled in the art will appreciate, the flow control assembly 700 can be actuated such that any combination of the first fluid inlet 716a, the second fluid inlet 716b, and the third fluid inlet 716c are blocked or unblocked to provide at least eight different therapy levels (ranging from all three fluid inlets blocked to all three fluid inlets unblocked).

In some embodiments, the resistances provided by each individual channel 752 can have a predetermined ratio. For example, the resistance provided by the third channel 752c when the third fluid inlet 716c is unblocked, the resistance provided by the second channel 752b when the second fluid inlet 716b is unblocked, and the resistance provided by the first channel when the first fluid inlet 716a is unblocked can have a ratio of 1:2:4. In some embodiments, for a given pressure, the flow rate through the system 10 when only the first fluid inlet 716a is unblocked can be about X, the flow rate through the system when only the second fluid inlet 716a is unblocked can be about 2×, and the flow rate through the system when only the third fluid inlet 716c is unblocked can be about 4×. In this way, the pattern of resistances (and drainage rates) that can be achieved using the system 10 can be adjusted according to a known pattern. For example, the actuators 701 can be actuated such that any combination of fluid inlets 716 are blocked and unblocked, thereby providing any flow rate between X (only the first fluid inlet 716a is unblocked) and 7× (all the fluid inlets 716 are unblocked). Additional details regarding the ability to provide a plurality of therapy levels using intraocular shunting systems having a variety of fluid inlets are described in International Patent Application No. PCT/US21/14774, the disclosure of which is incorporated by reference herein in its entirety.

In some embodiments, the therapy level (e.g., drainage rate, flow resistance, etc.) is determined by the relative dimensions of the channels 752, not the number or size of the fluid inlets 716. For example, as previously described, the channels 752 can have different dimensions. In some embodiments, a diameter or other cross-sectional area of the first channel 752a is smaller than a diameter or other cross-sectional area of the second channel 752b, which itself is smaller than a diameter or other cross-sectional area of the third channel 752c. In embodiments in which the flow resistance is determined by the channels 760, the fluid inlets 716 can nevertheless include a different number of apertures to provide a visual cue to the healthcare provide reflecting the relative fluid resistances of the corresponding channel (e.g., one aperture means the corresponding fluid channel has a first resistance, two apertures means the corresponding fluid channel has a second resistance less than the first, etc.). In other embodiments, the fluid inlets 716 can include another visual cue or indicator to reflect the relative fluid resistances of the corresponding channel.

Without being bound by theory, using a rotational/pivotable motion to selectively block and/or unblock the fluid inlets 716 is expected to provide several advantages relative to actuators operating via linear motion. For example, a relatively small motion in the actuation elements 708 can be translated into a relatively large motion of the distal region 702b of the projection 702. Without being bound by theory, this is expected to decrease the amount of strain required in the first and second actuation elements 708 to move the projection 702 (e.g., to block and/or unblock the fluid inlets 716). In turn, this may further increase the consistency of motion of the projection 702 as compared to an actuator with linearly arranged actuation elements.

Figure 8A:
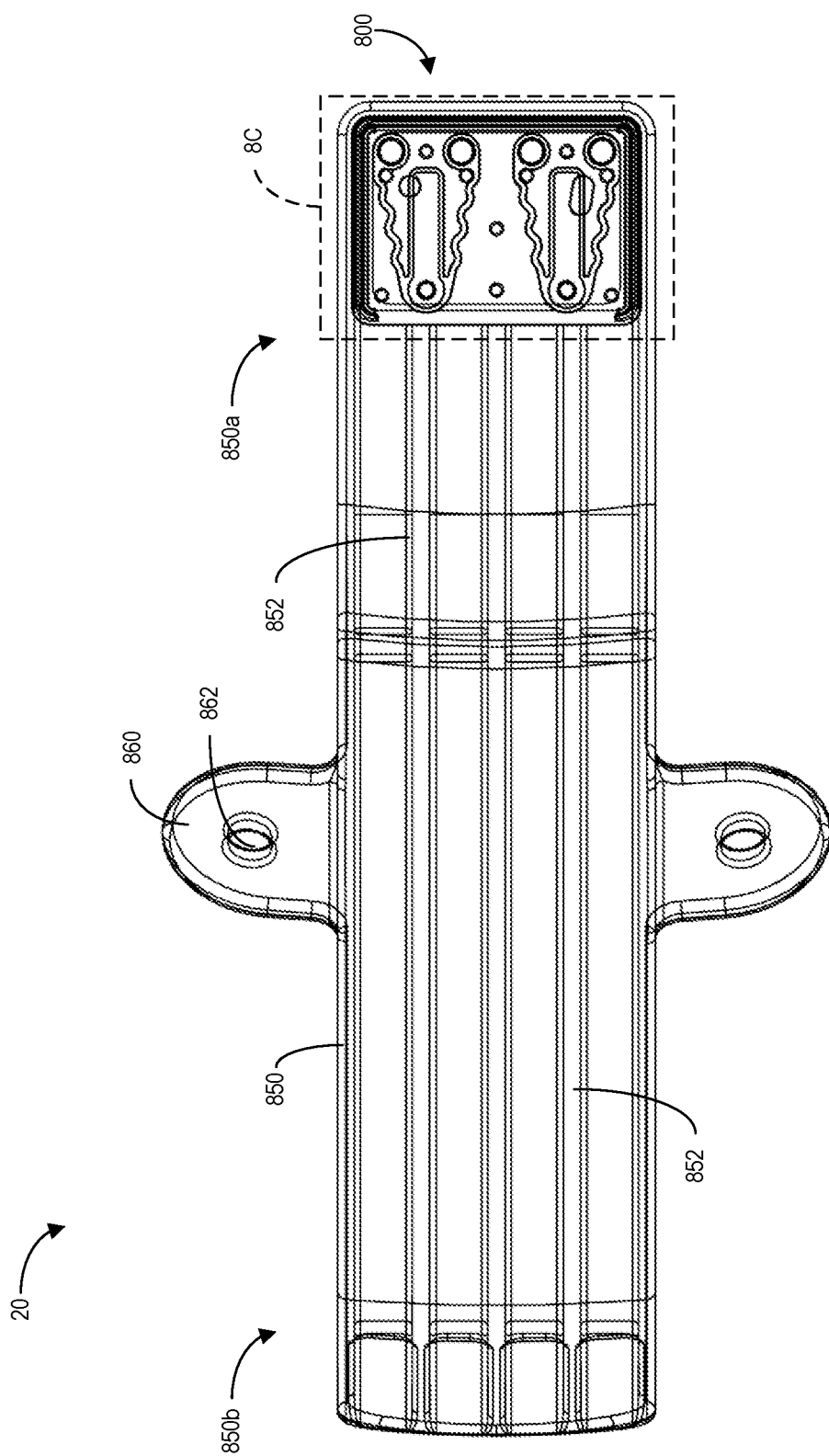
FIG. 8A is a front view of another intraocular shunting system configured in accordance with select embodiments of the present technology.
Figure 8B:
FIG. 8B is a side view of the intraocular shunting system of FIG. 8A.
Figure 8C:
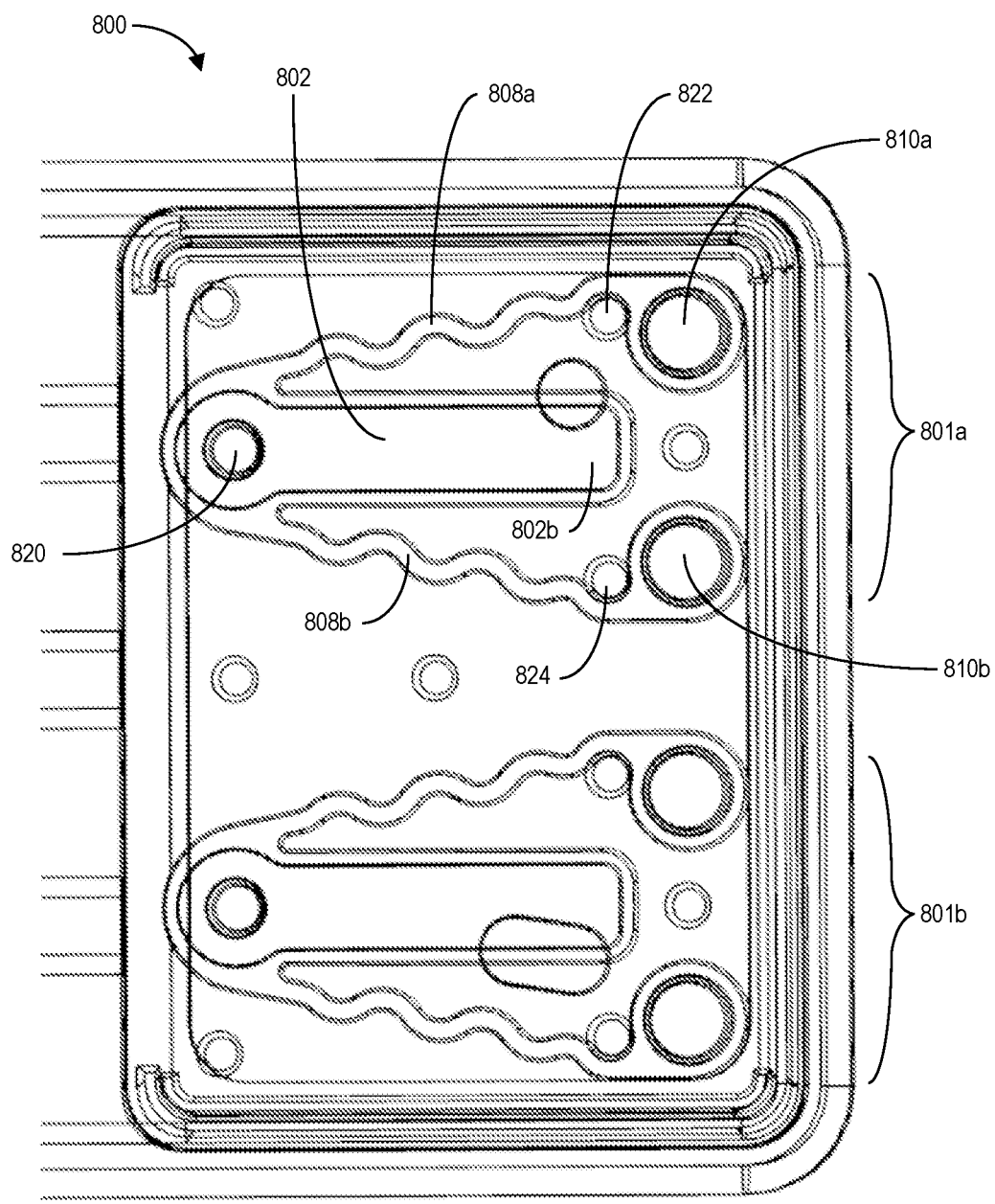
FIG. 8C is an enlarged front view of a flow control assembly of the intraocular shunting system of FIG. 8A.

FIGS. 8A-8C illustrate an intraocular shunting system 20 (the "system 20") configured in accordance with select embodiments of the present technology. More specifically, FIG. 8A is a front view of the system 20, FIG. 8B is a side view of the system 20, and FIG. 8C is an enlarged front view of a flow control assembly 800 of the system 20 taken along the lines indicated in FIG. 8A. The system 20 can be generally similar to the system 10 described with respect to FIGS. 7A-7E. For example, referring to FIG. 8A, the system 20 can include a drainage element 850 and a flow control assembly 800. The drainage element 850 can extend between a first end portion 850a and a second end portion 850b, and can have a generally flat profile. The drainage element 850 can further include one or more channels 852 extending between the first end portion 850a and the second end portion 850b. When implanted in a patient's eye, the first end portion 850a can reside at least partially within an interior region of the eye (e.g., an anterior chamber), and the second end portion 850b can reside at least partially within and/or be in fluid communication with a desired outflow location (e.g., a subconjunctival bleb space). The drainage element 850 can optionally include one or more wings or appendages 860 having holes (e.g. suture holes) for securing the drainage element 850 in a desired position. As best shown in FIG. 8B, the drainage element 850 can have a generally curved profile to better conform to the anatomy of the eye.

Referring to FIG. 8C, the flow control assembly 800 can include a first actuator 801a and a second actuator 801b (collectively referred to as the "actuators 801"). The actuators 801 can be generally similar to the actuators 701 described with respect to FIGS. 7A-7E. For example, the first actuator 801a can include a projection 802 (e.g., a finger, a tongue, a lever, a gating element, a control element, etc.), a first actuation element 808a, a second actuation element 808b, a first target 810a, and a second target 810b. The first actuator 801a can be restrained and/or secured to the drainage element 850 via a first restraint 820, a second restraint 822, and a third restraint 824. The projection 802 can rotate/pivot about the first restraint 820, as described above with respect to FIGS. 7A-7E. However, unlike the actuators 701, the first actuator 801a can also rotate/pivot around the second restraint 822 and the third restraint 824. Accordingly, the actuators 801 can rotate at three locations (e.g., the first actuator 801a has three rotational degrees of freedom).

Figure 9A:
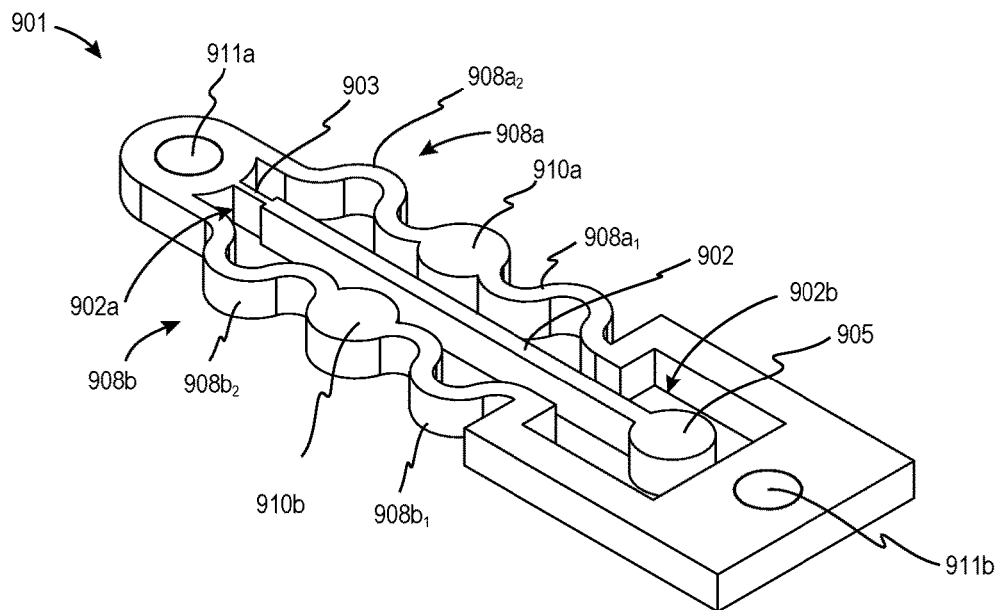
FIGS. 9A-9D illustrate an actuator for selectively controlling the flow of fluid through shunting systems and configured in accordance with select embodiments of the present technology.
Figure 9B:
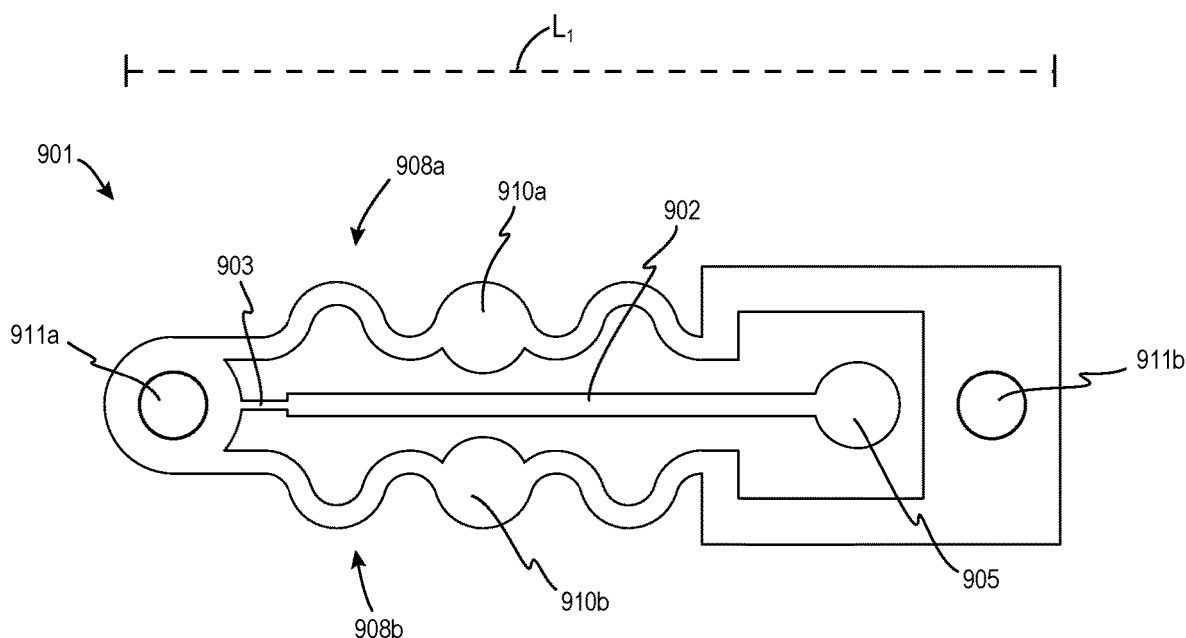
Figure 9C:
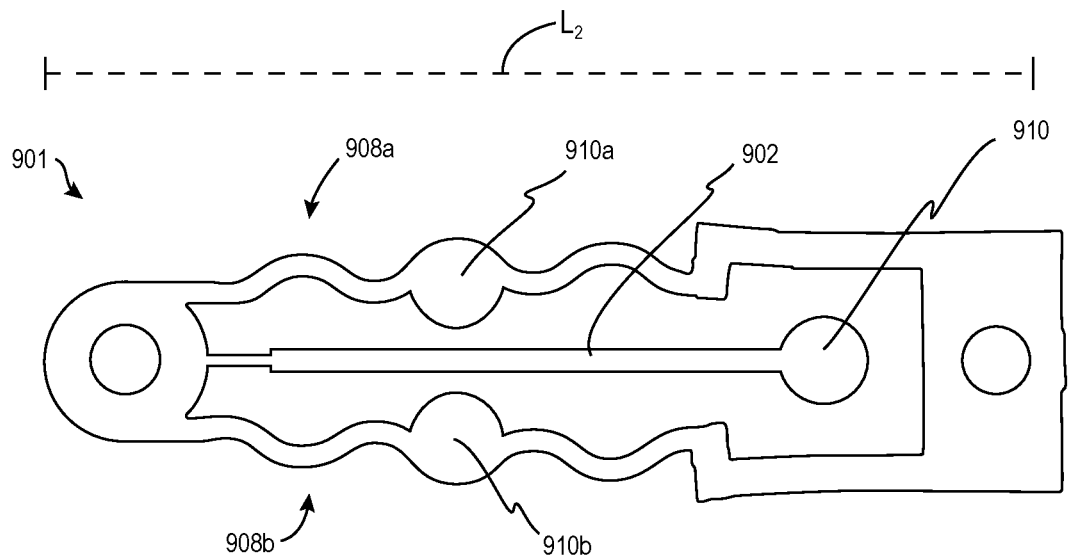
Figure 9D:
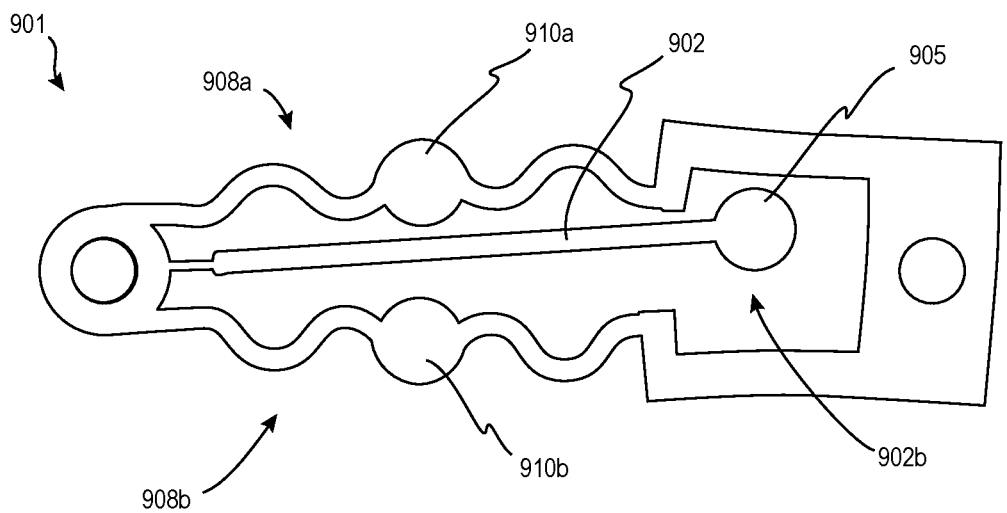

FIGS. 9A-9D illustrate an actuator 901 for controlling the flow of fluid in a shunting system and configured in accordance with select embodiments of the present technology. More specifically, FIG. 9A is an isometric view of the actuator 901, FIG. 9B is a top view of the actuator 901 in a fabricated or non-tensioned configuration, FIG. 9C is a top view of the actuator 901 in a tensioned configuration, and FIG. 9D is a top view of the actuator 901 in an actuated configuration. The actuator 901 is shown in isolation for clarity. However, as one skilled in the art will appreciate, the actuator 901 can be used in systems similar to the system 10 or the system 20 described with reference to FIGS. 7A-7E and FIGS. 8A-8C, respectively (e.g., instead of actuators 701 and 801, respectively). Moreover, the actuator 901 can operate in a manner generally similar to the actuator 701 (FIGS. 7A-7E) and the actuator 801 (FIGS. 8A-8C) previously described. Accordingly, the following description places particular focus on features and functions of the actuator 901 that are different than those previously described.

Referring first to FIG. 9A, the actuator 901 includes a projection 902, a first actuation element 908a, and a second actuation element 908b (collectively referred to as the "actuation elements 908"). In operation, the actuation elements 908 can be selectively and independently actuated to rotate the projection 902 to block (e.g., interfere with, partially interfere with, etc.) or unblock (e.g., clear, avoid, etc.) a fluid inlet (e.g., the fluid inlet 716 of the system 10, shown in FIG. 7A) for controlling the flow of fluid therethrough, as previously described herein. The projection 902 can include select features that in at least some embodiments increase the efficiency and/or flow control imparted by the actuator 901. For example, the projection 902 can include a blocking feature 905 positioned at its distal region 902b. The blocking feature 905 can have an enlarged surface area or volume to better enable the projection 902 to interface with one or more fluid inlets (e.g., the fluid inlets 716 of the system 10) when in a "closed" position to control the flow of fluid therethrough. The blocking feature 905 can nevertheless be configured to permit fluid flow through the one or more fluid inlets when in an "open" position. The projection 902 can also have a neck region 903 at its proximal region 902a that has a thinner cross-section than other portions of the projection 902. Strain induced by the projection 902 contacting another portion of the actuator 901 during operation can be preferentially minimized by the neck region 903, rather than being concentrated into other portions of the actuator 901 (e.g., the actuation elements 908). This is expected to improve the reproducibility and consistency of motion that can be induced during actuation of the actuator 901.

The actuator 901 also includes a first target 910a and a second target 910b (collectively referred to as the "targets 910") for receiving energy to power the actuation elements 908. Unlike the actuators described with respect to FIGS. 7A-8C, the targets 910 of the actuator 901 are positioned along the respective actuation elements 908. In particular, the first target 910a is positioned on the first actuation element 908a such that it divides the first actuation element 908a into a first portion $908a_1$ and a second portion $908a_2$. Likewise, the second target 910b is positioned on the second actuation element 908b such that it divides the second actuation element 908b into a first portion $908b_1$ and a second portion $908b_2$. Energy received at the first target 910a can spread into both the first portion $908a_1$ and the second portion $908a_2$ of the first actuation element 908a, and energy received at the second target 910b can spread into both the first portion $908b_1$ and the second portion $908b_2$ of the second actuation element 908b. Without being bound by theory, placing the targets 910 along the actuation elements 908 is therefore expected to more quickly and/or efficiently spread energy received at the targets 910 into the corresponding actuation elements 908 for driving operation thereof (e.g., by reducing the dissipative loss of heat within the actuation elements 908).

The actuator 901 further includes a first aperture 911a and a second aperture 911b for securing the actuator 901 to a drainage element, plate, or other structure (e.g., the drainage element 750 of the system 10, shown in FIG. 7A). For example, the first aperture 911a can be configured to receive a first pin or other anchoring element, and the second aperture 911b can be configured to receive a second pin or other anchoring element. Accordingly, the actuator 901 is securable to a drainage element or other shunting structure at two locations. In some embodiments, the actuator 901 is configured to be rotatably secured to the drainage element or other shunting structure at least at the first aperture 911a such that the projection 902 can rotate upon actuation of the actuation elements 908, as previously described with respect to the actuator 701 of FIGS. 7A-7E.

The actuator 901 can be manufactured and operated in a manner generally similar to those described for the actuator 701 and 801. FIG. 9B, for example, illustrates the actuator 901 in a fabricated or non-tensioned position, in which the actuator 901 has a first length $L_1$. The actuator 901 can be fabricated from a unitary or contiguous piece of material (e.g., nitinol), as previously described with respect to FIGS. 7A-7E. Once fabricated, the actuator 901 can be manipulated into a different, tensioned configuration before/while being secured to a shunt or other structure (e.g., the actuator 901 may be manipulated such that the first aperture 911a and the second aperture 911b align with and engage pins extending from a drainage element or other shunting structure). FIG. 9C illustrates the actuator 901 in a tensioned configuration in which the actuator 901 has been stretched or otherwise lengthened relative to the fabricated position such that it has a second length $L_2$ that is greater than the first length $L_1$. In other embodiments, the actuator 901 may be compressed relative to the fabricated configuration to form a tensioned configuration in which L2 would be less than $L_1$. In the tensioned position shown in FIG. 9C, the first actuation element 908a and the second actuation element 908b are both lengthened relative to their preferred (e.g., fabricated) geometries. Accordingly, as previously described with respect to FIGS. 7A-7E, the first actuation element 908a and the second actuation element 908b can be selectively actuated by applying energy to the first target 910a or the second target 910b, respectively, to rotate the projection 902 to block or unblock a fluid inlet on the shunt structure (not shown). FIG. 9D, for example, illustrates the actuator 901 following actuation of the second actuation element 908b. Because the second actuation element 908b is lengthened relative to its preferred (e.g., fabricated) geometry, heating at least a portion of the second actuation element 908b above its transition temperature induces a material phase change in the second actuation element 908b, causing the second actuation element 908b to contract toward its preferred (e.g., fabricated) geometry. This causes the distal region 902b of the projection 902 to rotate upwardly. This movement can be reversed by heating at least a portion of the first actuation element 908a above its transition temperature to induce a material phase change therein, causing the first actuation element 908a to contract toward its preferred (e.g., fabricated) geometry and rotate the projection 902 downwardly.

Figure 10A:
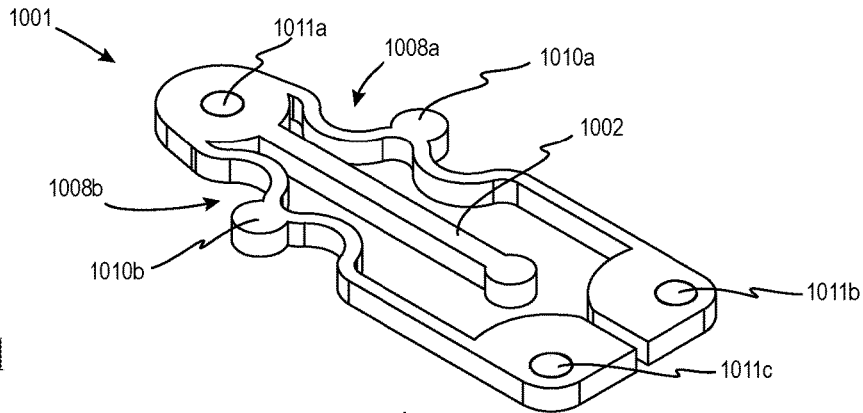
FIGS. 10A-10D illustrate another actuator for selectively controlling the flow of fluid through shunting systems and configured in accordance with select embodiments of the present technology.
Figure 10B:
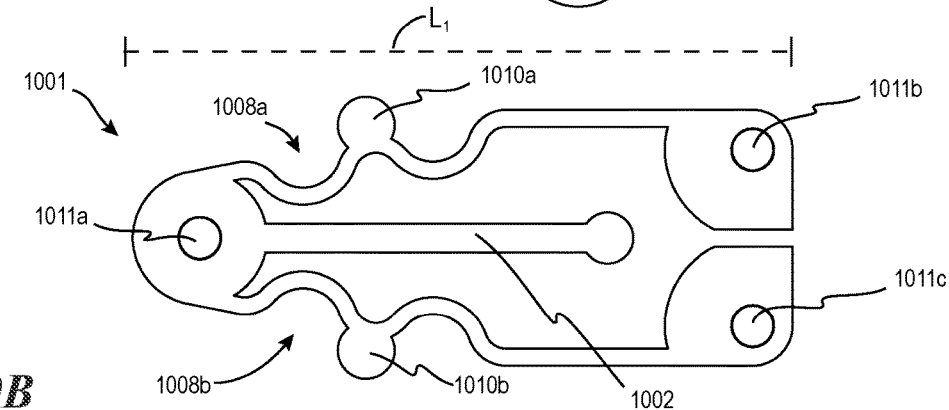
Figure 10C:
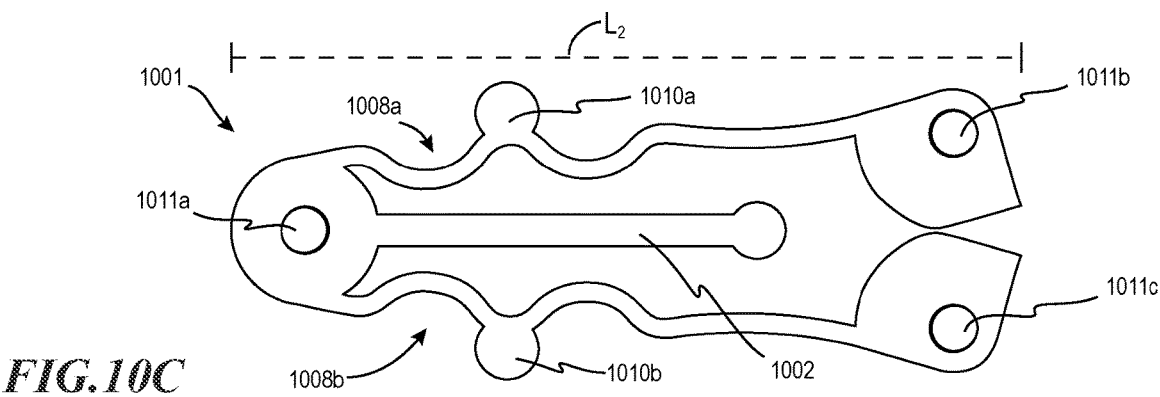
Figure 10D:
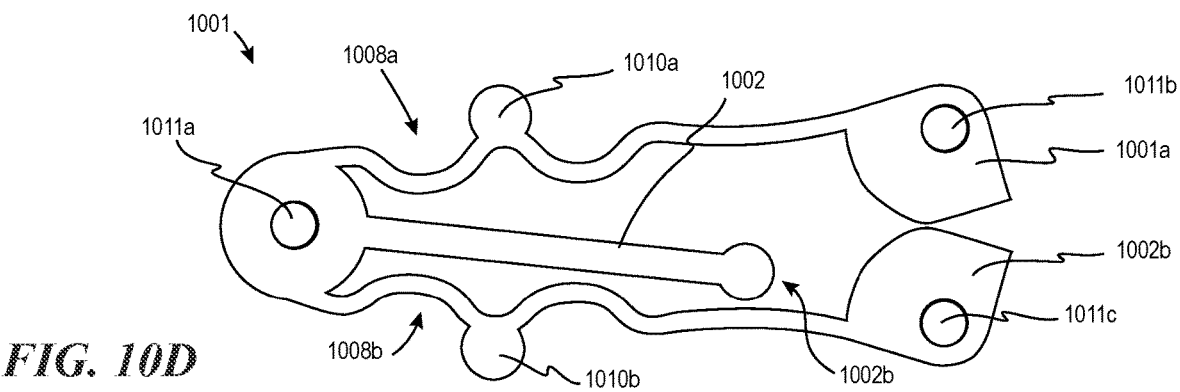

FIGS. 10A-10D illustrate another actuator 1001 for controlling the flow of fluid in a shunting system and configured in accordance with select embodiments of the present technology. More specifically, FIG. 10A is an isometric view of the actuator 1001, FIG. 10B is a top view of the actuator 1001 in a fabricated or non-tensioned configuration, FIG. 10C is a top view of the actuator 1001 in a tensioned configuration, and FIG. 10D is a top view of the actuator 1001 in an actuated configuration. The actuator 1001 is shown in isolation for clarity. However, as one skilled in the art will appreciate, the actuator 1001 can be used in systems similar to the system 10 or the system 20 described with reference to FIGS. 7A-7E and FIGS. 8A-8C, respectively (e.g., instead of the actuators 701 and 801, respectively). Moreover, the actuator 1001 can operate in a manner generally similar to the actuator 701 (FIGS. 7A-7E), the actuator 801 (FIGS. 8A-8C), and/or the actuator 901 (FIGS. 9A-9D) previously described. Accordingly, the following description places particular focus on features and functions of the actuator 1001 that are different than those previously described.

Referring first to FIG. 10A, the actuator 1001 includes a projection 1002, a first actuation element 1008a, and a second actuation element 1008b (collectively referred to as the "actuation elements 1008"). In operation, the actuation elements 1008 can be selectively and independently actuated to rotate the projection 1002 to block or unblock a fluid inlet (e.g., the fluid inlet 716 of the system 10, shown in FIG. 7A) for controlling the flow of fluid therethrough, as previously described herein. The actuator 1001 also includes a first target 1010a and a second target 1010b (collectively referred to herein as the "targets 1010") for receiving energy to power the actuators. Similar to the actuator 901 of FIGS. 9A-9D, the targets 1010 of the actuator 1001 are positioned along the respective actuation elements 1008 to facilitate quicker and/or more efficient heating of the actuation element 1008 upon application of energy to the respective targets 1010.

The actuator 1001 further includes a first aperture 1011a, a second aperture 1011b, and a third aperture 1011c for securing the actuator 1001 to a drainage element, plate, or other structure (e.g., the drainage element 750 of the system 10, shown in FIG. 7A). Accordingly, the actuator 1001 is securable to a drainage element or other shunting structure at least at three locations. In some embodiments, the actuator 1001 is configured to be rotatably secured to the drainage element or other shunting structure at least at the first aperture 1011a such that the projection 1002 can rotate upon actuation of the actuation elements 1008, as previously described with respect to the actuator 701 of FIGS. 7A-7E. In some embodiments, the actuator 1001 is also configured to be rotatably secured to the drainage element or other shunting structure at the second aperture 1011b and the third aperture 1011c, although in other embodiments the actuator 1001 is configured to be fixedly secured to the drainage element at the second aperture 1011b and/or the third aperture 1011c. Accordingly, the actuator 1001 can have between one and three rotational degrees of freedom.

The actuator 1001 can be manufactured and operated in a manner generally similar to those described previously. FIG. 10B illustrates the actuator 1001 in a fabricated or non-tensioned position, in which the actuator 1001 has a first length $L_1$. The actuator 1001 can be fabricated from a unitary or contiguous piece of material (e.g., nitinol), as previously described with respect to FIGS. 7A-7E. Once fabricated, the actuator 1001 can be manipulated into a different, tensioned configuration before/while being secured to a shunt or other structure (e.g., the actuator 100 may be manipulated such that the first aperture 1011a, the second aperture 1011b, and the third aperture 1011c align with and engage pins extending from a plate or other drainage element). FIG. 10C illustrates the actuator 1001 in a tensioned configuration in which the actuator 1001 has been stretched or otherwise lengthened relative to the fabricated position such that it has a second length $L_2$ that is greater than the first length $L_1$. In other embodiments, the actuator 1001 may be compressed relative to the fabricated configuration to form a tensioned configuration in which $L_2$ would be less than $L_1$. In the tensioned position shown in FIG. 10C, the first actuation element 1008a and the second actuation element 1008b are both lengthened relative to their preferred (e.g., fabricated) geometries. Accordingly, as previously described with respect to FIGS. 7A-7E, the first actuation element 1008a and the second actuation element 1008b can be selectively actuated by applying energy to the first target 1010a or the second target 1010b, respectively, to rotate the projection 1002 to block or unblock a fluid inlet on the shunt structure (not shown). FIG. 10D, for example, illustrates the actuator 1001 following actuation of the first actuation element 1008a. Because the first actuation element 1008a is lengthened relative to its preferred geometry, heating at least a portion of the first actuation element 1008a above its transition temperature induces a material phase change in the first actuation element 1008a, causing the first actuation element 1008a to contract toward its preferred geometry. This causes the distal region 1002b of the projection 1002 to rotate downwardly. This movement can be reversed by heating at least a portion of the second actuation element 1008b above its transition temperature to induce a material phase change therein, causing the second actuation element 1008b to contract toward its preferred geometry and rotate the projection 1002 upwardly.

As shown in FIG. 10D, actuating one of the actuation elements 1008 may cause a first end region 1001a and a second end region 1001b of the actuator 1001 to bend or flare inwardly. This can be reduced or prevented by preventing rotation at the second aperture 1011b and the third aperture 1011c (e.g., by preventing rotation about the pins used to secure the actuator 1001 to a drainage element, plate, or other shunting structure), and/or using one or more restraints similar to the first target second restraint 726a and the second target second restraint 726b shown in FIGS. 7B and 7C. Without being bound by theory, preventing rotation at the first end region 1001a and the second end region 1001b is expected to produce greater displacement of the projection 1002 and/or increase strain within unconstrained portions of the actuator 1001.

Figure 11A:
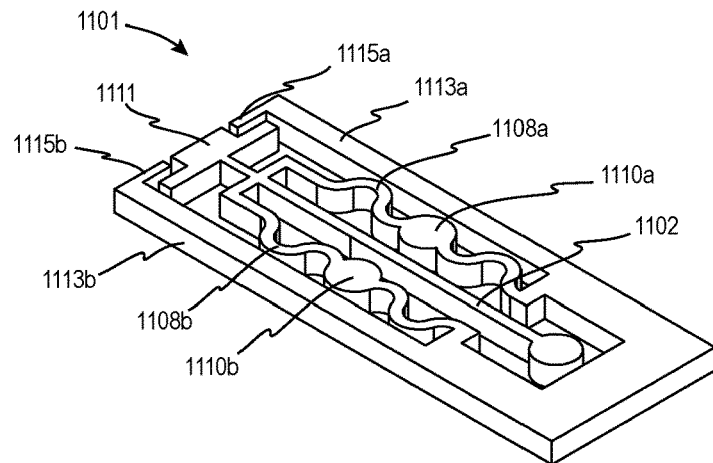
FIGS. 11A-11D illustrate yet another actuator for selectively controlling the flow of fluid through shunting systems and configured in accordance with select embodiments of the present technology.
Figure 11B:
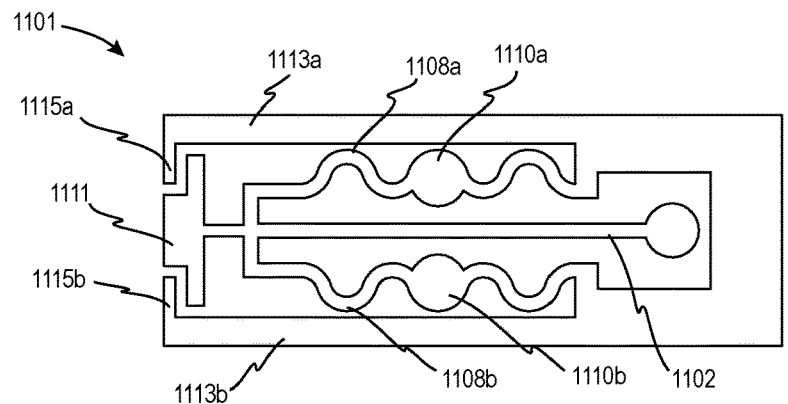
Figure 11C:
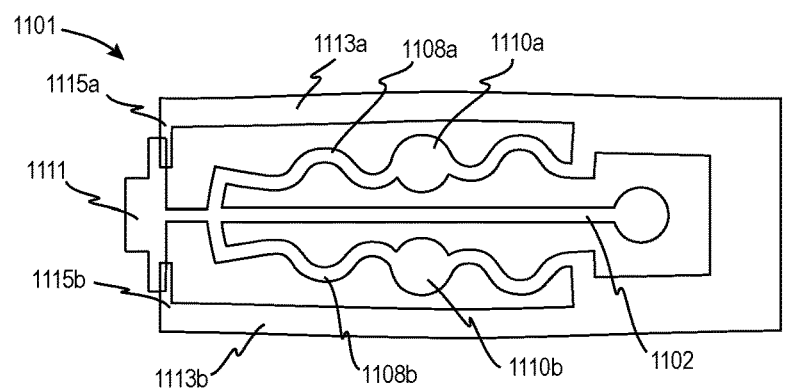
Figure 11D:
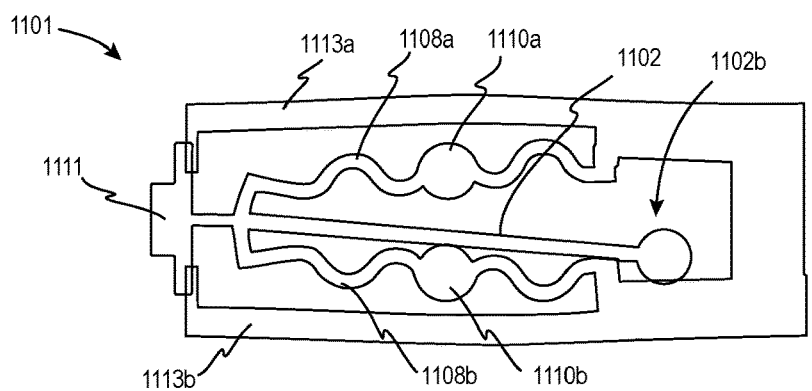

FIGS. 11A-11D illustrate another actuator 1101 for controlling the flow of fluid in a shunting system and configured in accordance with select embodiments of the present technology. More specifically, FIG. 11A is an isometric view of the actuator 1101 in a fabricated or non-tensioned configuration, FIG. 11B is a top view of the actuator 1101 in the fabricated or non-tensioned configuration, FIG. 11C is a top view of the actuator 1101 in a tensioned configuration, and FIG. 11D is a top view of the actuator 1101 in an actuated configuration. The actuator 1101 is shown in isolation for clarity. However, as one skilled in the art will appreciate, the actuator 1101 can be used in systems similar to the system 10 or the system 20 described with reference to FIGS. 7A-7E and FIGS. 8A-8C, respectively (e.g., instead of the actuators 701 and 801, respectively). Moreover, the actuator 1101 can operate in a manner generally similar to the actuator 701 (FIGS. 7A-7E), the actuator 801 (FIGS. 8A-8C), the actuator 901 (FIGS. 9A-9D), and/or the actuator 1001 (FIGS. 10A-10D) previously described. Accordingly, the following description places particular focus on features and functions of the actuator 1101 that are different than those previously described.

Unlike the actuators 701, 801, 901, and 1001, the actuator 1101 can be secured to itself to transform the actuator 1101 from the fabricated configuration to the tensioned configuration. For example, referring to FIGS. 11A and 11B, which shows the actuator 1101 in the fabricated configuration, the actuator 1101 includes a first arm 1113a and a second arm 1113b extending generally parallel to the first actuation element 1108a and the second actuation element 1108b, respectively. A first appendage 1115a extends laterally inward from the first arm 1113a toward the second arm 1113b, and a second appendage 1115b extends laterally inward from the second arm 1113b toward the first arm 1113a. The actuator 1101 further includes an anchoring element 1111 extending in a direction generally opposite of the projection 1102. In the fabricated configuration, the anchoring element 1111 resides on the same side of the first and second appendages 1115 as the projection 1102 and actuation elements 1108. To secure the actuator 1101 in a tensioned configuration as shown in FIG. 11C, the anchoring element 1111 can be stretched and positioned on the side of the first and second appendages 1115 opposite to the projection 1102 and the actuation element 1108. As shown, the appendages 1115 interfere with the anchoring element 1111 and prevent the anchoring element 1111 (and thus the actuation elements 1108) from returning to the fabricated configuration. This deforms (e.g., lengthens) the actuation elements 1108 relative to their preferred (e.g., fabricated) geometries, thereby enabling them to be selectively actuated by heating them above their transition temperatures, as previously described. The actuator 1101 therefore does not require pins or other fastening elements to secure the actuator 1101 in a tensioned configuration. In some embodiments, the anchoring element 1111 can be optionally secured to the appendages 1115 following tensioning of the actuator 1101. The can be done by bonding (e.g., welding, adhesive, etc.). Although FIGS. 11C and 11D show the anchoring element 1111 overlapping with the appendages 1115, the anchoring elements 1111 generally would not overlap the appendages 1115.

Once secured in the tensioned configuration, the actuator 1101 can operate in a generally similar manner as described for the actuator 701. For example, the first actuation element 1108a and the second actuation element 1108b can be selectively actuated by applying energy to the first target 1110a or the second target 1110b, respectively, to rotate the projection 1102 to block or unblock a fluid inlet on the shunt structure (not shown). FIG. 11D, for example, illustrates the actuator 1101 following actuation of the first actuation element 1108a. Because the first actuation element 1108a is lengthened relative to its preferred geometry, heating at least a portion of the first actuation element 1108a above its transition temperature induces a material phase change in the first actuation element 1108a, causing the first actuation element 1108a to contract toward its preferred geometry. This causes the distal region 1102b of the projection 1102 to rotate downwardly. This movement can be reversed by heating at least a portion of the second actuation element 1108b above its transition temperature to induce a material phase change therein, causing the second actuation element 1108b to contract toward its preferred geometry and rotate the projection 1102 upwardly.

In some embodiments, the arms 1113 are not constrained by other aspects of the shunting system (e.g., the system 10 shown in FIG. 7A), and therefore bow slightly outward during operation of the actuator 1101. In other embodiments, the arms 1113 can be constrained by one or more features of the shunting system to prevent the arms 1113 from bowing outward during operation of the actuator 1101. Preventing the arms 1113 from bowing outward shifts more energy into the actuation elements 1108, thereby permitting greater displacement of the projection 1102. Therefore, the arms 1113 can be optionally restrained to create a tuning mechanism for adjusting the range of motion of the projection 1102.

Figure 12A:
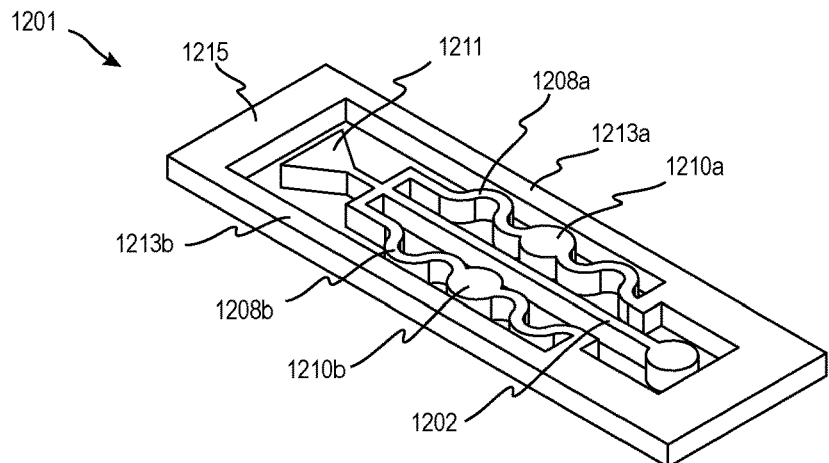
FIGS. 12A-12D illustrate yet another actuator for selectively controlling the flow of fluid through shunting systems and configured in accordance with select embodiments of the present technology.
Figure 12B:
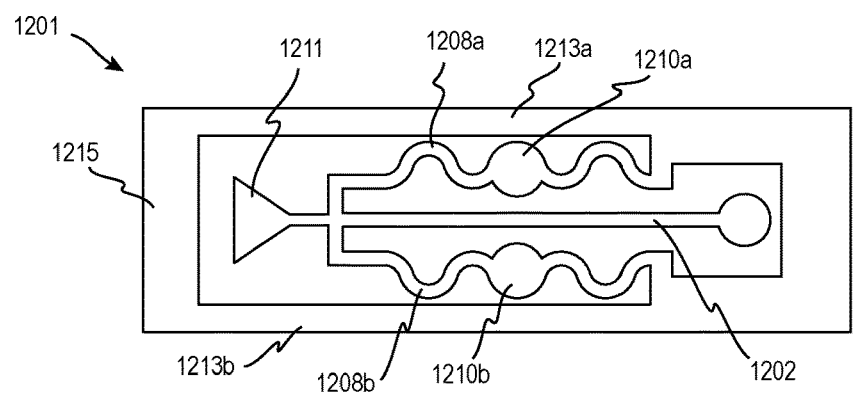
Figure 12C:
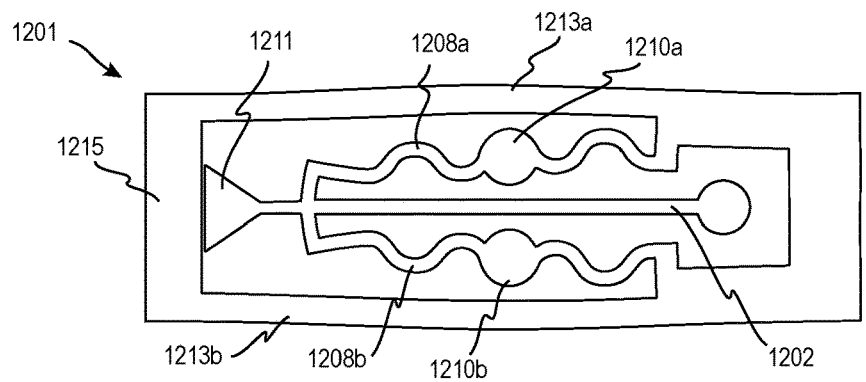
Figure 12D:
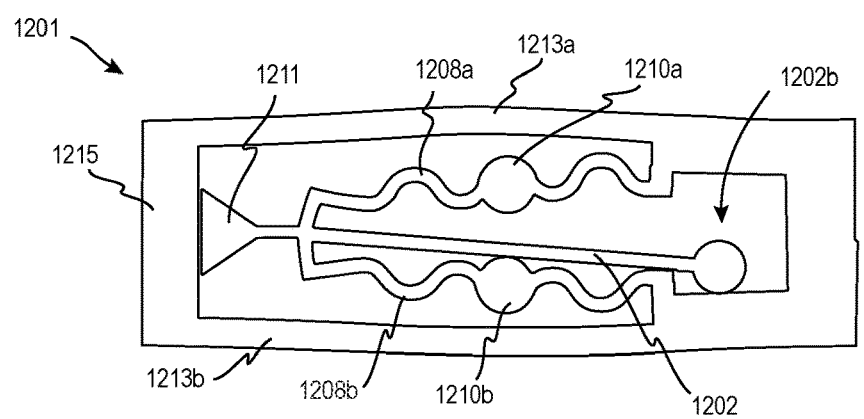

FIGS. 12A-12D illustrate yet another actuator 1201 for controlling the flow of fluid in a shunting system and configured in accordance with select embodiments of the present technology. More specifically, FIG. 12A is an isometric view of the actuator 1201 in a fabricated or non-tensioned configuration, FIG. 12B is a top view of the actuator 1201 in the fabricated or non-tensioned configuration, FIG. 12C is a top view of the actuator 1201 in a tensioned configuration, and FIG. 12D is a top view of the actuator 1201 in an actuated configuration. The actuator 1201 is shown in isolation for clarity. However, as one skilled in the art will appreciate, the actuator 1201 can be used in systems similar to the system 10 or the system 20 described with reference to FIGS. 7A-7E and FIGS. 8A-8C, respectively (e.g., instead of the actuators 701 and 801, respectively). Moreover, the actuator 1101 can operate in a manner generally similar to the actuator 701 (FIGS. 7A-7E), the actuator 801 (FIGS. 8A-8C), the actuator 901 (FIGS. 9A-9D), the actuator 1001 (FIGS. 10A-10D), and/or the actuator 1101 (FIGS. 11A-11D) previously described. Accordingly, the following description places particular focus on features and functions of the actuator 1201 that are different than those previously described.

Similar to the actuator 1101, the actuator 1201 can be secured to itself to transition the actuator 1201 from the fabricated configuration to the tensioned configuration. Referring to FIGS. 12A and 12B, which show the actuator 1201 in a fabricated configuration, the actuator 1201 includes a first arm 1213a and a second arm 1213b extending generally parallel to the first actuation element 1208a and the second actuation element 1208b, respectively. The actuator 1101 further includes an anchoring element 1111 extending in a direction generally opposite of the projection 1102. The actuator 1201 further includes a bridge element 1215 coupling the first arm 1213a to the second arm 1213b and enclosing the anchoring element 1111, the projection 1202, the first actuation element 1208a, and the second actuation element 1208b. To secure the actuator 1201 in a tensioned configuration as shown in FIG. 12C, the anchor element 1211 can be secured to the bridge 1215, thereby deforming (e.g., lengthening) the first actuation element 1208a and the second actuation element 1208b relative to their preferred (e.g., fabricated) geometries. The anchor element 1211 can be secured to the bridge 1215 via a locking mechanism or other suitable adhesion techniques (e.g. welding, suturing, gluing, taping, etc.). In some embodiments, the bridge 1215 may include a recess configured to receive and secure the anchor element 1211.

Once secured in the tensioned configuration, the actuator 1201 can operate in a generally similar manner as described for the actuator 701. For example, the first actuation element 1208a and the second actuation element 1208b can be selectively actuated by applying energy to the first target 1210a or the second target 1210b, respectively, to rotate the projection 1202 to block or unblock a fluid inlet on the shunt structure (not shown). FIG. 12D, for example, illustrates the actuator 1201 following actuation of the first actuation element 1208a. Because the first actuation element 1208a is lengthened relative to its preferred geometry, heating at least a portion of the first actuation element 1208a above its transition temperature induces a material phase change in the first actuation element 1208a, causing the first actuation element 1208a to contract toward its preferred geometry. This causes the distal region 1202b of the projection 1202 to rotate downwardly. This movement can be reversed by heating at least a portion of the second actuation element 1208b above its transition temperature to induce a material phase change therein, causing the second actuation element 1208b to contract toward its preferred geometry and rotate the projection 1202 upwardly. As described above with respect to the FIG. 11D, the arms 1213 can optionally be restrained when the actuator 1301 is positioned within a shunting system (e.g., the system 10) to reduce outward bowing during operation and/or to tune operation of the actuator 1201.

Figure 13A:
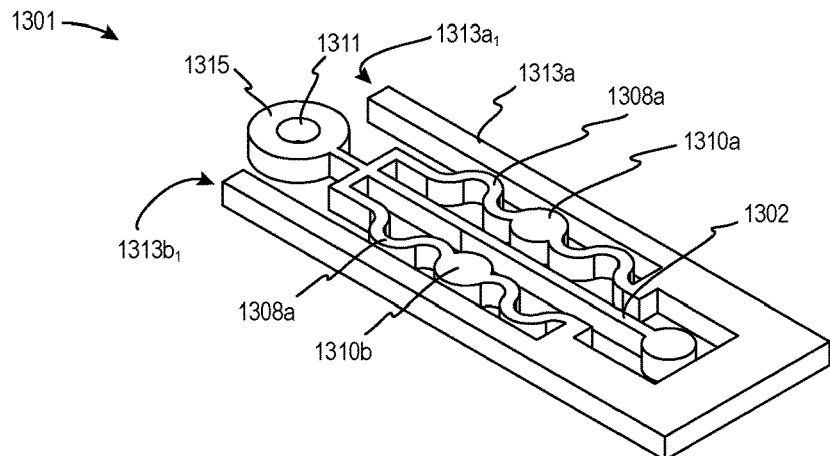
FIGS. 13A-13D illustrate yet another actuator for selectively controlling the flow of fluid through shunting systems and configured in accordance with select embodiments of the present technology.
Figure 13B:
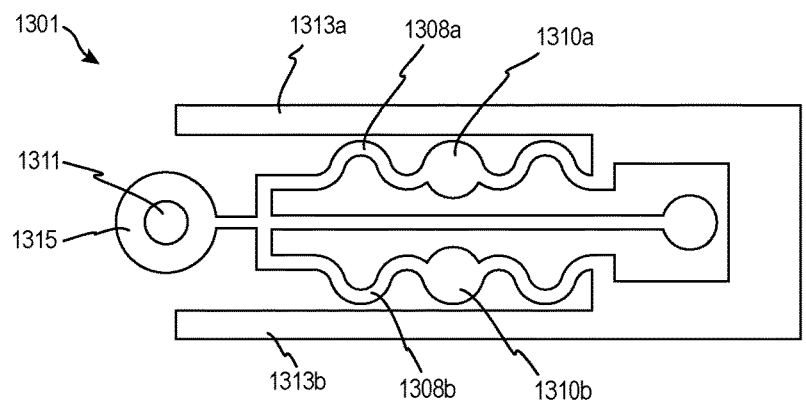
Figure 13C:
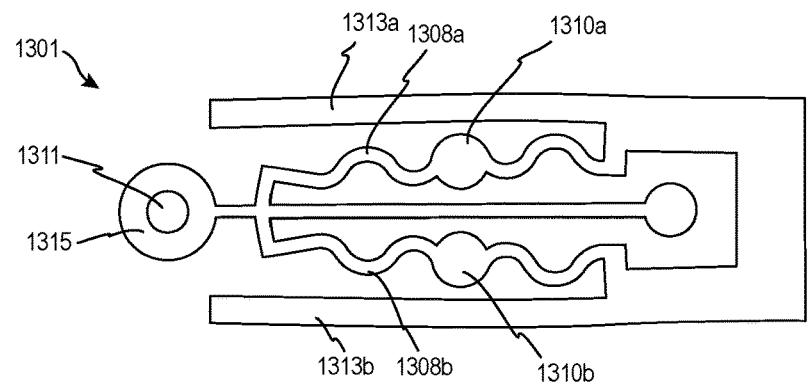
Figure 13D:
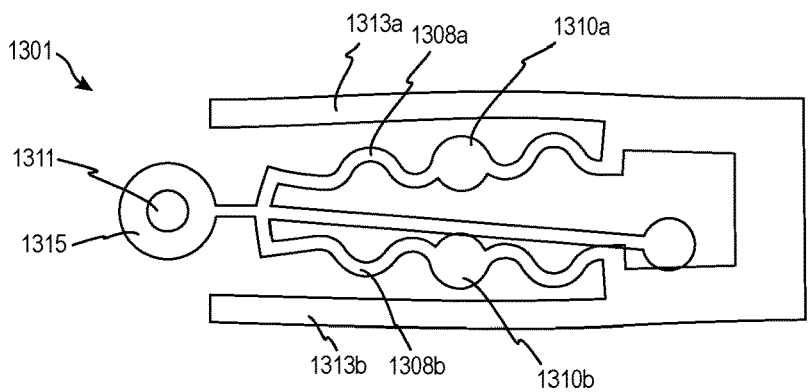

FIGS. 13A-13D illustrate yet another actuator 1301 for controlling the flow of fluid in a shunting system and configured in accordance with select embodiments of the present technology. More specifically, FIG. 13A is an isometric view of the actuator 1301 in a fabricated or non-tensioned configuration, FIG. 13B is a top view of the actuator 1301 in the fabricated or non-tensioned configuration, FIG. 13C is a top view of the actuator 1301 in a tensioned configuration, and FIG. 13D is a top view of the actuator 1301 in an actuated configuration. The actuator 1301 is shown in isolation for clarity. However, as one skilled in the art will appreciate, the actuator 1301 can be used in systems similar to the system 10 or the system 20 described with reference to FIGS. 7A-7E and FIGS. 8A-8C, respectively (e.g., instead of the actuators 701 and 801, respectively). Moreover, the actuator 1101 can operate in a manner generally similar to the actuator 701 (FIGS. 7A-7E), the actuator 801 (FIGS. 8A-8C), the actuator 901 (FIGS. 9A-9D), the actuator 1001 (FIGS. 10A-10D), the actuator 1101 (FIGS. 11A-11D), and/or the actuator 1201 (FIGS. 12A-12D) previously described. Accordingly, the following description places particular focus on features and functions of the actuator 1301 that are different than those previously described.

The actuator 1301 includes a first arm 1313a and a second arm 1313b extending generally parallel to the first actuation element 1308a and the second actuation element 1308b, respectively. The actuator 1301 also includes an anchoring element 1315 having an aperture 1311 extending therethrough. To secure the actuator 1301 to a drainage element, plate, or other shunting structure (not shown) in a tensioned configuration, the anchoring element 1315 can be secured to the drainage element via one or more pins inserted into the aperture 1311. This can include deforming the actuator 1301 relative to its fabricated configuration to occupy a tensioned configuration (shown in FIG. 13C). The actuator 1301 can be retained in its tensioned configuration by virtue of free end regions $1313a_1$ and $1313b_1$ of the first and second arms 1313a, 1313b engaging one or more features on the drainage element. Once secured in the tensioned configuration, the actuator 1301 can operate in a generally similar manner as described for the other actuators herein (e.g., the actuator 1301 can be actuated to move the projection 1302, as shown in FIG. 13D).

Figure 14A:
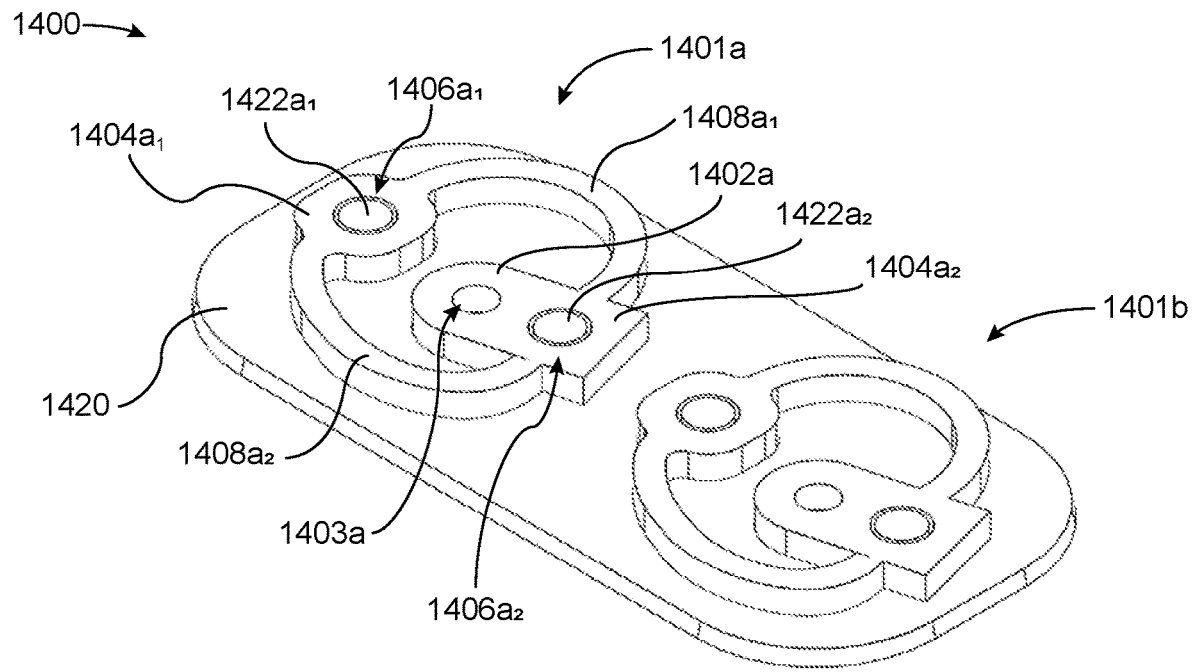
FIGS. 14A-14E illustrate a flow control assembly for selectively controlling the flow of fluid through shunting systems and configured in accordance with select embodiments of the present technology.
Figure 14B:
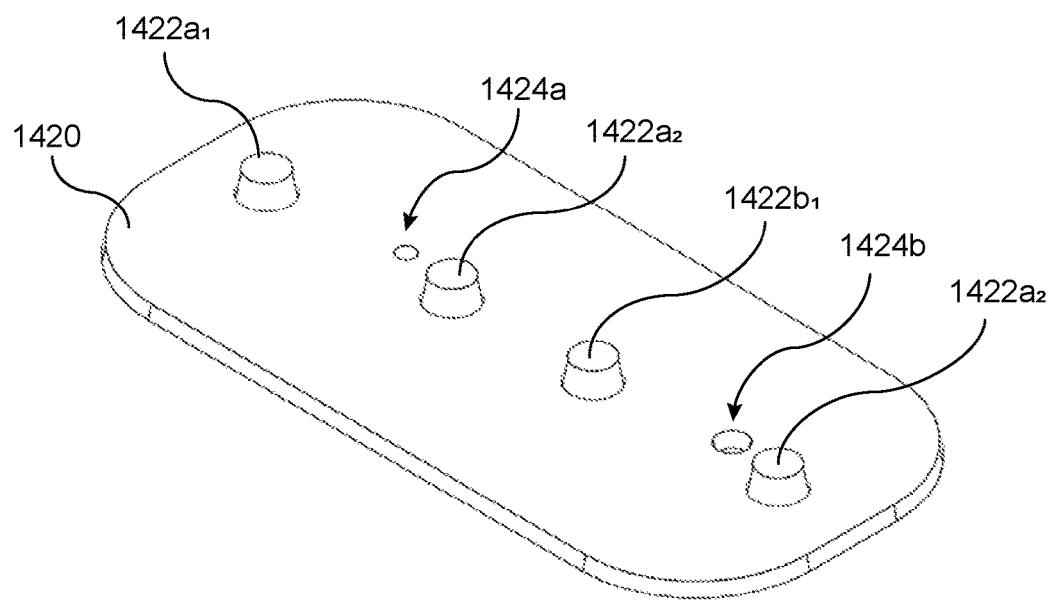
Figure 14C:
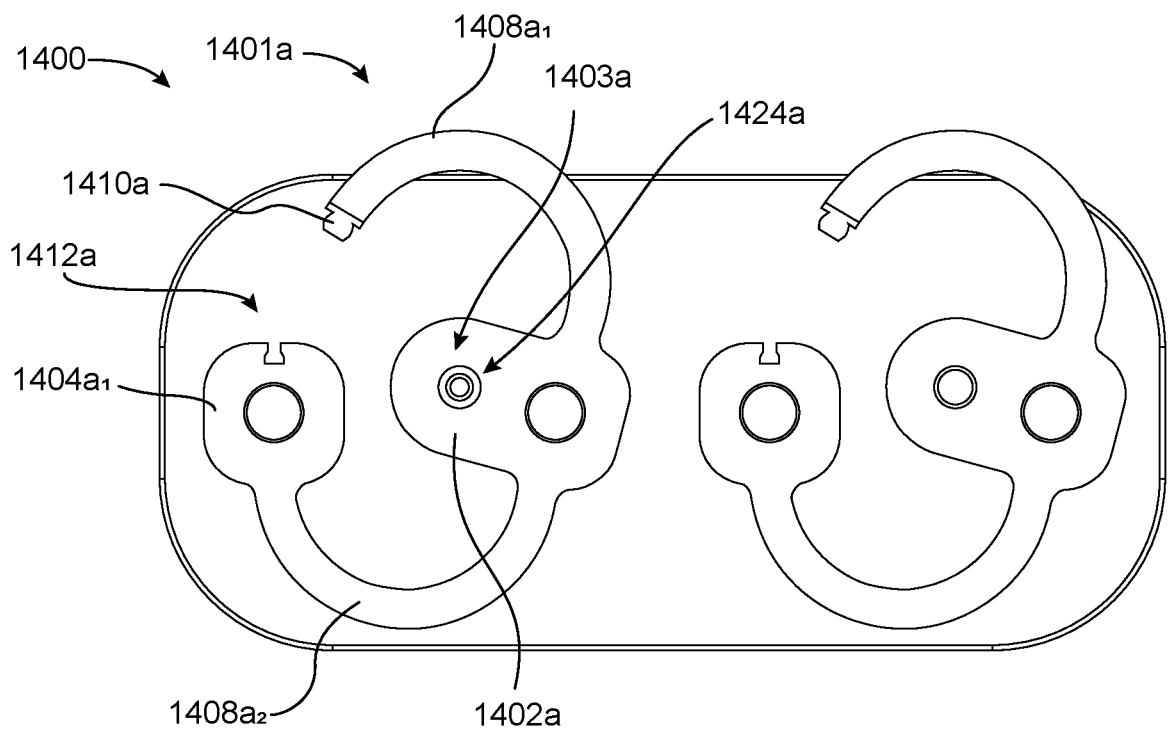
Figure 14D:
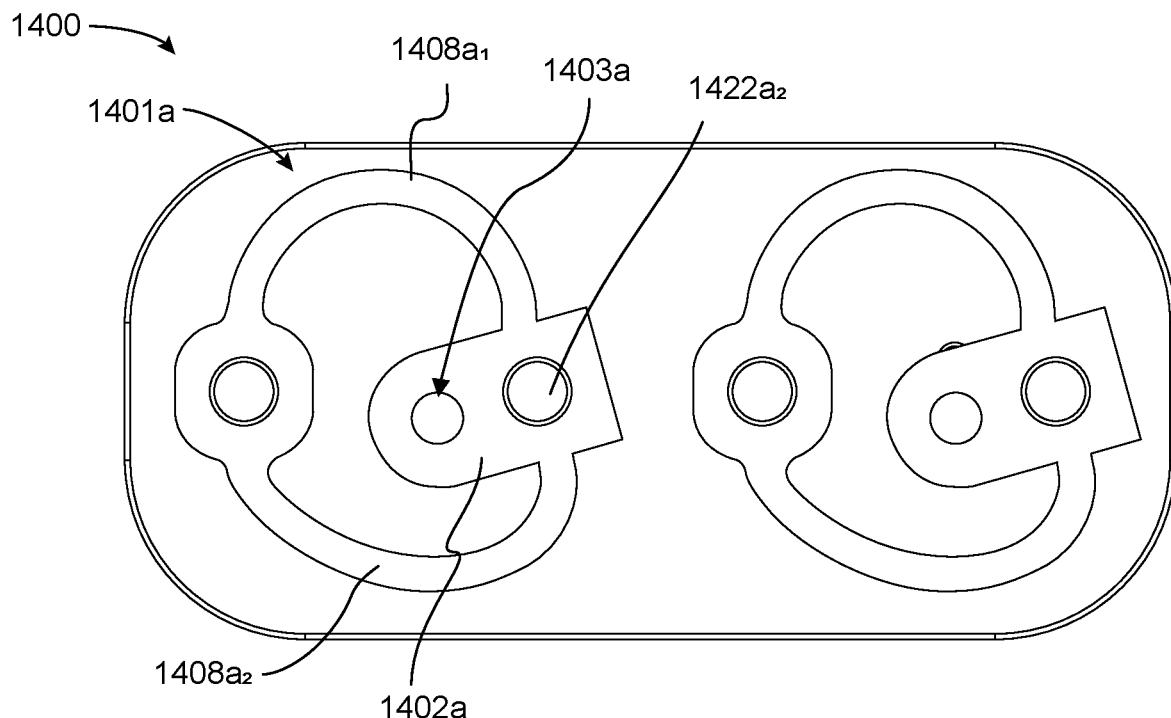
Figure 14E:
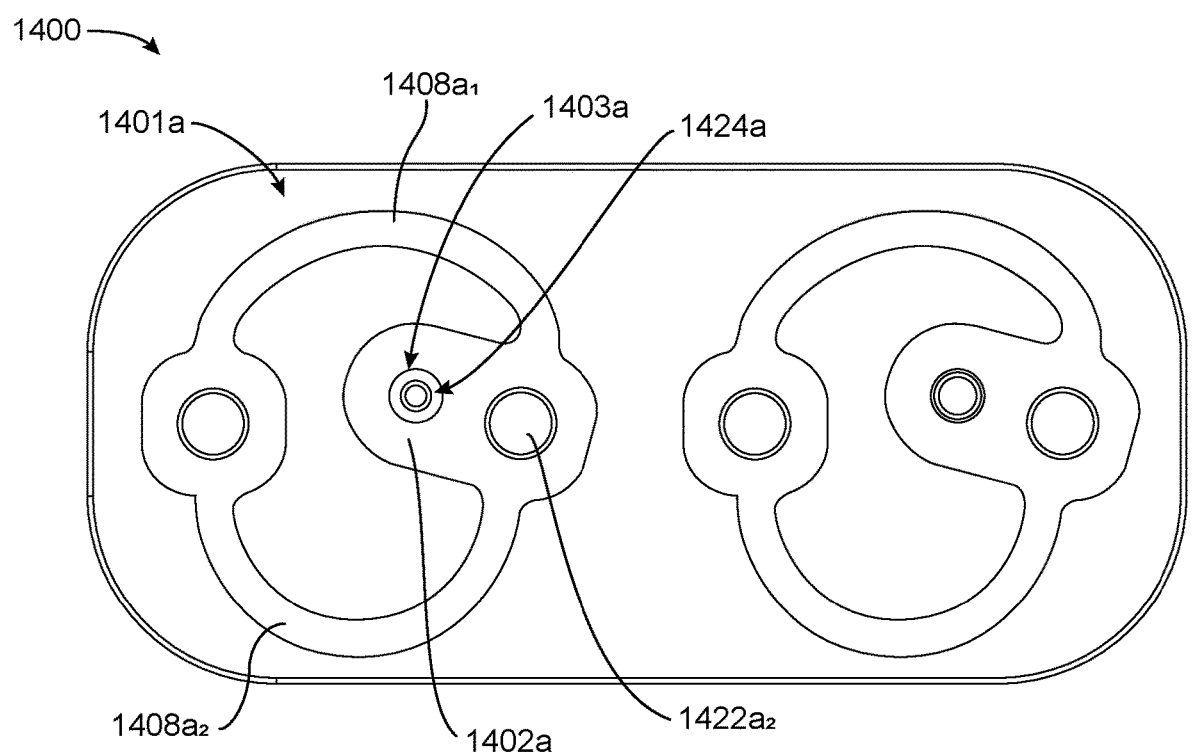

FIGS. 14A-14E illustrate a flow control assembly 1400 ("the assembly 1400") for controlling the flow of fluid in a shunting system and configured in accordance with select embodiments of the present technology. More specifically, FIG. 14A is an isometric view of the assembly 1400, FIG. 14B is an isometric view of a base structure 1420 of the assembly 1400 with the other features omitted for clarity, FIG. 14C is a top down view of the assembly 1400 in a fabricated or non-tensioned configuration, FIG. 14D is a top down view of the assembly 1400 in a loaded or tensioned configuration, and FIG. 14E is a top down view of the assembly 1400 in the loaded or tensioned configuration after it has been actuated relative to the configuration shown in FIG. 14D.

Referring first to FIG. 14A, the assembly 1400 includes a first actuator 1401a, a second actuator 1401b, and a base structure 1420. The first actuator 1401a and the second actuator 1401b (referred to collectively as "the actuators 1401") can be coupled to the base structure 1420, which is described in greater detail below with reference to FIG. 14B. In some embodiments, the assembly 1400 can be used in systems similar to the system 10 or the system 20 described with reference to FIGS. 7A-7E and FIGS. 8A-8C, respectively (e.g., instead of the actuators 701 and 801, respectively). In other embodiments, the assembly 1400 can be coupled to another drainage element or shunting structure for draining fluid.

The first actuator 1401a can include a first anchoring region $1404a_1$ and a second anchoring region $1404a_2$. The first actuator 1401a can be coupled to the base structure 1420 at the first anchoring region $1404a_1$ and the second anchoring region $1404a_2$. For example, the first anchoring region $1404a_1$ can have a first opening $1406a_1$ extending therethrough that is configured to receive a first anchoring mechanism or pin $1422a_1$ extending from the base structure 1420. Likewise, the second anchoring region $1404a_2$ can include a second opening $1406a_2$ extending therethrough that is configured to receive a second anchoring mechanism or pin $1422a_2$ extending from the base structure 1420. In some embodiments, the first actuator 1401a may alternatively or additionally be coupled to the base structure 1420 via other suitable connection mechanisms, such as gluing, welding, or the like. In some embodiments, the first anchoring region $1404a_1$ and/or the second anchoring region $1404a_2$ is rotatably/pivotably coupled to the base structure 1420 such that the first anchoring region $1404a_1$ and/or the second anchoring region $1404a_2$ can rotate about the first pin $1422a_1$ and/or the second pin $1422a_2$, respectively. In some embodiments, the second anchoring region $1404a_2$ is rotatably coupled to the base structure 1420 and the first anchoring region $1404a_1$ is fixedly coupled to the base structure (e.g., to prevent rotation of the first anchoring region $1404a_1$ relative to the base structure 1420).

The first actuator 1401a further includes a projection 1402a extending from the second anchoring region $1404a_2$. The projection 1402a can be or include a finger, a tongue, a lever, a gating element, a control element, or the like. The projection 1402a can further include an opening or aperture 1403a extending therethrough. The projection 1402a can be configured to control the flow of fluid through a first fluid inlet 1424a (shown in FIG. 3B) on the base structure 1420. For example, as described in greater detail below with reference to FIGS. 14D and 14E, the projection 1402a can be moved between a first (e.g., open) position in which the opening 1403a at least partially aligns with the first fluid inlet 1424a (permitting fluid to flow through the first fluid inlet 1424a) and a second (e.g., closed) position in which the opening 1403a does not align with the first fluid inlet 1424a (substantially preventing fluid to flow through the first fluid inlet 1424a).

The first actuator 1401a further includes a first actuation element $1408a_1$ and a second actuation element $1408a_2$ (collectively referred to as the actuation elements 1408a) to induce movement of the projection 1402. The actuation elements 1408a can extend between the first anchoring region $1404a_1$ and the second anchoring region $1404a_2$. The actuation elements 1408a can be composed of a shape memory material (e.g., nitinol), and can be actuated via a shape memory effect, as previously described in detail herein. In operation, the actuation elements 1408a can be selectively and independently actuated to rotate the projection 1402a such that the opening 1403a at least partially aligns with the first fluid inlet 1424a or such that the opening 1403a does not align with the first fluid inlet 1424a, thereby controlling the flow of fluid through the first fluid inlet 1424a.

The second actuator 1401b can be generally similar to and/or the same as the first actuator 1401a, and can be configured to control the flow of fluid through a second fluid inlet 1424b of the base structure 1420 (FIG. 14B). Moreover, although shown has having two actuators 1401, the assembly 1400 can have fewer or more actuators, such as one, three, four, five, six, or more actuators.

Referring next to FIG. 14B, the base structure 1420 can be a generally flat or plate-like structure having one or more retention features for securing the actuators 1401 to the base structure 1420. The retention features can include the first pin $1422a_1$ and the second pin $1422a_2$ for securing the first actuator 1401a to the base structure 1420, as previously described. The retention features can also include a third pin $1422b_1$ and a fourth pin $1422b_2$ for securing the second actuator 1401b to the base structure 1420. Although shown as pins, the base structure 1420 can include other suitable anchoring or retention features for securing the actuators 1401 thereto. As described above, the base structure 1420 also includes the first fluid inlet 1424a and the second fluid inlet 1424b. When the assembly 1400 is secured to or positioned within a drainage element, the first fluid inlet 1424a and/or the second fluid inlet 1424b can align with or otherwise be in fluid communication with one or more channels or lumens that transport fluid entering the drainage element via the first fluid inlet 1424a and/or the second fluid inlet 1424b to a desired outflow location.

FIG. 14C illustrates the actuators 1401 coupled to the base structure 1420 in a nontensioned or uncoupled configuration in which the first actuation element $1408a_1$ of the first actuator 1401a is not coupled to the first anchoring region $1404a_1$. As illustrated, the first actuation element $1408a_1$ can include a locking feature $1410a_1$ (e.g., a flange, lip, protrusion, key, etc.) configured engage (e.g., releasably engage) a retention feature 1412a (e.g., a groove, notch, aperture, etc.) on the first anchoring region $1404a_1$. In other embodiments, the first anchoring region $1404a_1$ can include the locking feature 1410a, and the first actuation element $1408a_1$ can include the retention feature 1412b. In yet other embodiments, the second actuation element $1408a_2$ may include a locking feature and be decoupled from the first or second anchoring region. In some embodiments, the first actuator 1401a is fabricated in the uncoupled or nontensioned configuration. For example, the first actuator 1401a may be laser cut from a single piece of material, such that the first actuator 1401a comprises a unitary structure.

To transition the first actuator 1401a from the nontensioned configuration shown in FIG. 14C to the tensioned configuration shown in FIG. 14D, the locking feature 1410a can be positioned within or otherwise interfaced with the retention feature 1412a. The act of positioning the locking feature 1410a in the retention feature 1412a can deform at least one of the actuation elements 1408a relative to their preferred or fabricated geometry. For example, positioning the locking feature 1410a in the retention feature 1412a can stretch (e.g., tension) the first actuation element $1408a_1$ relative to its preferred geometry and/or can stretch (e.g., tension) the second actuation element $1408a_2$ relative to its preferred geometry. In some embodiments, both the first actuation element $1408a_1$ and the second actuation element $1408a_2$ are under substantially equal tension when in the tensioned configuration shown in FIG. 14C. As shown in FIG. 14D, in the coupled or tensioned configuration, the projection 1402a blocks the first fluid inlet 1424a (e.g., the opening 1403a does not align with the first fluid inlet 1424a). In use, this prevents or substantially prevents fluid from flowing through the first fluid inlet 1424a. The second actuator 1401b can be transitioned between the nontensioned and tensioned configurations in the same or similar manner as described for the first actuator 1401a.

Because the actuators 1401 are deformed relative to their preferred geometries in the tensioned configuration, movement of the actuators 1401 can be induced via the shape memory effect, as previously described herein for other shape memory actuators. For example, heating the second actuation element $1408a_2$ above its transition temperature can induce a phase transformation therein and cause it to move toward its preferred geometry. In particular, as shown in FIG. 14E, applying energy to the second actuation element $1408a_2$ causes it to contract toward its preferred geometry. Because the second actuation element $1408a_2$ is coupled to the second anchoring region $1404a_2$, contraction of the second actuation element $1408a_2$ causes the second anchoring region $1404a_2$ to pivot or otherwise rotate about the second pin $1422a_2$ as it contracts. This causes the projection 1402a, which extends from the second anchoring region $1404a_2$, to also rotate relative to the base structure 1420. In the illustrated embodiment, the projection 1402a rotates in a clockwise direction relative to the base structure 1420 upon actuation of the second actuation element $1408a_2$ such that the opening 1403a aligns with the first fluid inlet 1424a. In use, this permits fluid to flow through the first fluid inlet 1424a. The operation can be reversed (e.g., the first actuator 1401a can be moved to and/or toward the configuration shown in FIG. 14D) by actuating the first actuation element $1408a_1$. The actuation elements 1408 can therefore be selectively actuated to permit or prevent fluid from flowing through the first fluid inlet 1424a.

Although the projection 1402a is shown as having an opening 1403a that aligns with the first fluid inlet 1424a, in other embodiments the opening 1403a can be omitted from the projection 1402a, and the projection 1402a can simply move between a first position blocking (or substantially blocking) the first fluid inlet 1424a, and a second position unblocking (or substantially unblocking) the first fluid inlet 1424a, as previously described in detail herein. The second actuator 1401b can operate in the same or similar manner as the first actuator 1401a to control the flow of fluid through the second fluid inlet 1424b.

Figure 15A:
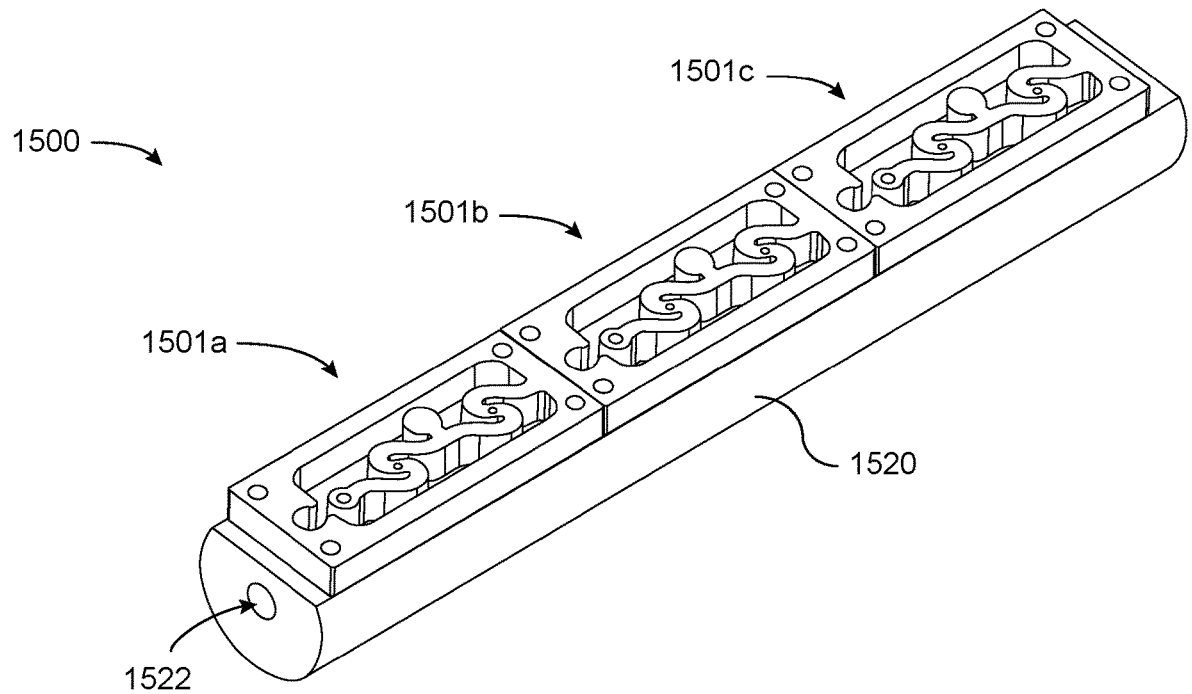
FIGS. 15A-15D illustrate another flow control assembly for selectively controlling the flow of fluid through shunting systems and configured in accordance with select embodiments of the present technology.
Figure 15B:
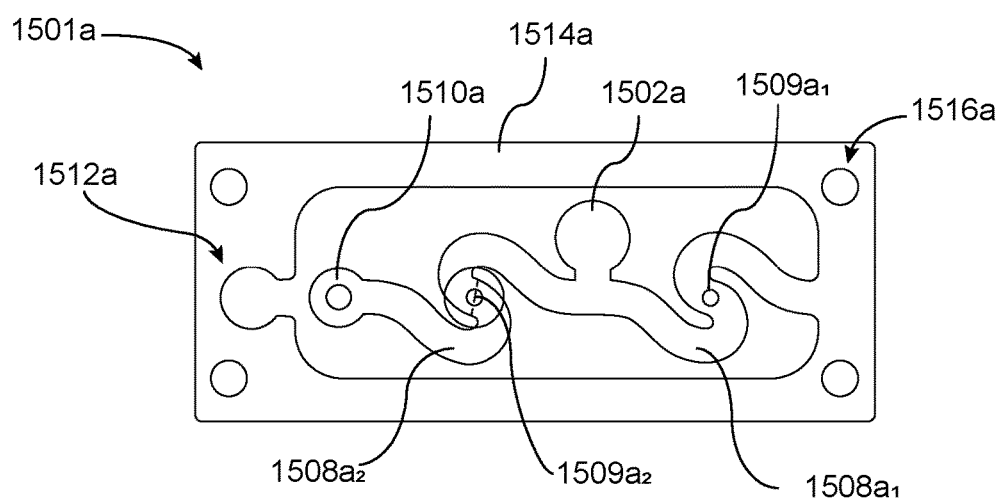
Figure 15C:
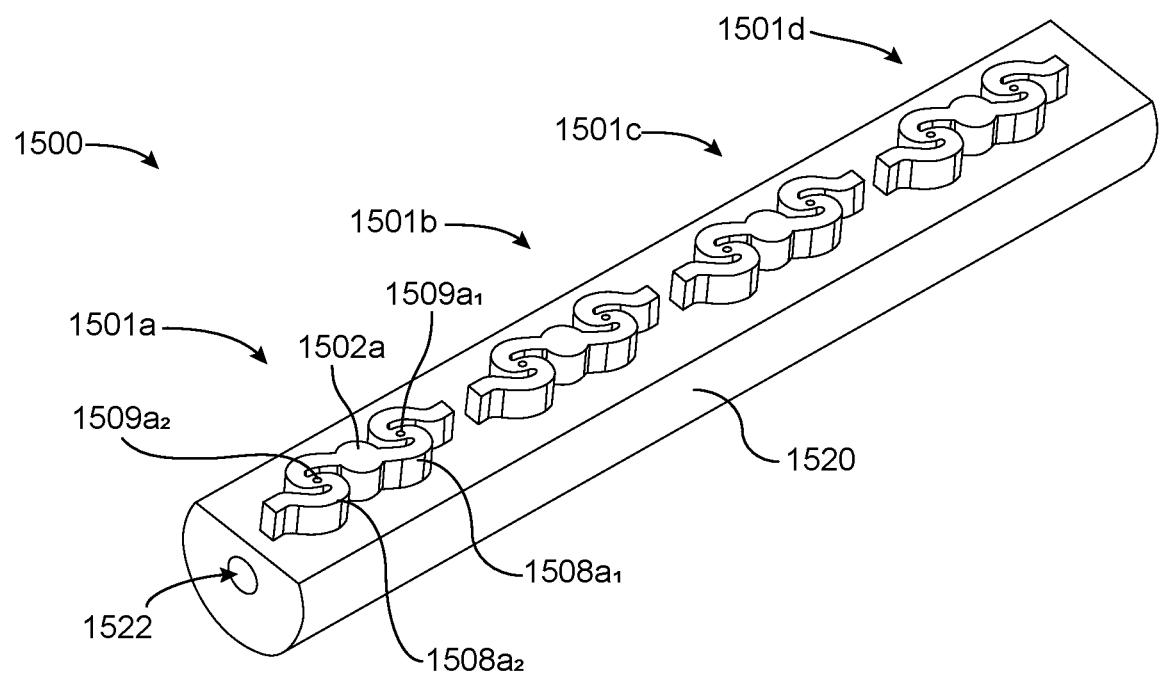

FIGS. 15A-15D illustrate another flow control assembly ("the assembly 1500") for controlling the flow of fluid in a shunting system and configured in accordance with select embodiments of the present technology. More specifically, FIG. 15A is an isometric view of the assembly 1500, FIG. 15B is an enlarged top down view of an actuator 1501a of the assembly 1500, FIG. 15C is an isometric view of a variation of the assembly 1500, and FIG. 15C is a series of top down views illustrating an actuation element 1508 during operation of the assembly 1500.

Referring first the FIG. 15A, the assembly 1500 includes a first actuator 1501a, a second actuator 1501b, a third actuator 1501c, and a base structure 1520. The first actuator 1501a, the second actuator 1501b, and the third actuator 1501c (referred to collectively as "the actuators 1501") can be coupled to the base structure 1520. The base structure 1520 can be or include a drainage element having a central lumen 1522 extending therethrough. In some embodiments, the base structure 1520 is a first drainage element, and the assembly 1500 is configured for use with a second drainage element or shunting structure for draining fluid, such as those described with reference to FIGS. 7A-7E and FIGS. 8A-8C (e.g., the lumen 1522 drains to another drainage element). Regardless, the base structure 1520 can include a plurality of fluid inlets (not shown) that permit fluid to flow into the lumen 1522. As previously described herein, the actuators 1501 can control the flow of fluid through the fluid inlets to control the therapy level provided by the assembly 1500. For example, the first actuator 1501a can interface with and control the flow of fluid through a first fluid inlet, the second actuator 1501b can interface with and control the flow of fluid through a second fluid inlet, and the third actuator 1501c can interface with and control the flow of fluid through a third fluid inlet.

Referring next to FIG. 15B, the first actuator 1501a can include a first actuation element $1508a_1$, a second actuation element $1508a_2$, and a control element 1502a positioned generally between the first actuation element $1508a_1$ and the second actuation element $1508a_2$. The control element 1502a is configured to interface with (e.g., selectively block and unblock) a fluid inlet on the base structure to control the flow of fluid therethrough. The actuation elements 1508 can be composed at least partially of a shape memory material and may induce movement of the control element 1502a via the shape memory effect, as previously described herein. In some embodiments, the actuation elements 1508 can have a partially wound, nested, S-shape, or other shape (collectively referred to as a "torsional" shape) supporting torsion in a portion of the actuation elements 1508 wherein the amount of strain reflected in the system is captured by the action of twisting (i.e., torsion) in the structure. In some embodiments, the degree to which the actuation elements 1508 are wound can be greater than or less than that illustrated in FIG. 15B.

The first actuation element 1508$a_1$ can further include a first target feature 1509$a_1$ and the second actuation element 1508$a_2$ can further include a second target feature 1509$a_2$ (collectively referred to as "the target features 1509$a$"). The target features 1509$a$ can provide a visual target to aim for when using laser energy to actuate the actuator 1501$a$. The first actuator 1501$a$ further includes an outer perimeter 1514$a$ generally encircling the first actuation element 1508$a_1$ and the second actuation element 1508$a_2$. The perimeter 1514$a$ can further include one or more openings 1516$a$ for securing the first actuator 1501$a$ to the base structure 1520.

The first actuator 1501$a$ is shown in an uncoupled or nontensioned configuration in FIG. 15B. In some embodiments, the first actuator 1501$a$ is fabricated in the uncoupled or nontensioned configuration. For example, the first actuator 1501$a$ may be laser cut from a single piece of material, such that the first actuator 1501$a$ comprises a unitary structure. To transition the first actuator 1501$a$ from the nontensioned configuration to a tensioned configuration (not shown), the actuation elements 1508 can be stretched (e.g., tensioned) and a locking feature 1510$a$ at the distal end portion of the second actuation element 1508$a_2$ can be placed within or otherwise secured to a retention feature 1512$a$ on the perimeter 1514$a$. This secures (e.g., releasably secures) the first actuator 1501 in a tensioned configuration. In particular, in the tensioned configuration, the first actuation element 1508$a_1$ and the second actuation element 1508$a_2$ are deformed relative to their preferred geometries. Therefore, the actuation elements 1508$a$ can be selectively activated via application of energy to inducement movement thereof, as previously described. Because the actuation elements 1508$a$ are coupled to the control element 1502$a$, movement of the actuation elements 1508$a$ can induce a corresponding movement of the control element 1502$a$.

FIG. 15C illustrates a variation of the assembly 1500, in which the perimeter 1514$a$ (FIG. 15A) of the actuation assembly is omitted for clarity. In particular, relative to the assembly 1500 shown in FIG. 15A, the control element 1502$a$ is placed longitudinally inline with the first actuation element 1508$a_1$ and the second actuation element 1508$a_2$.

Figure 15D:
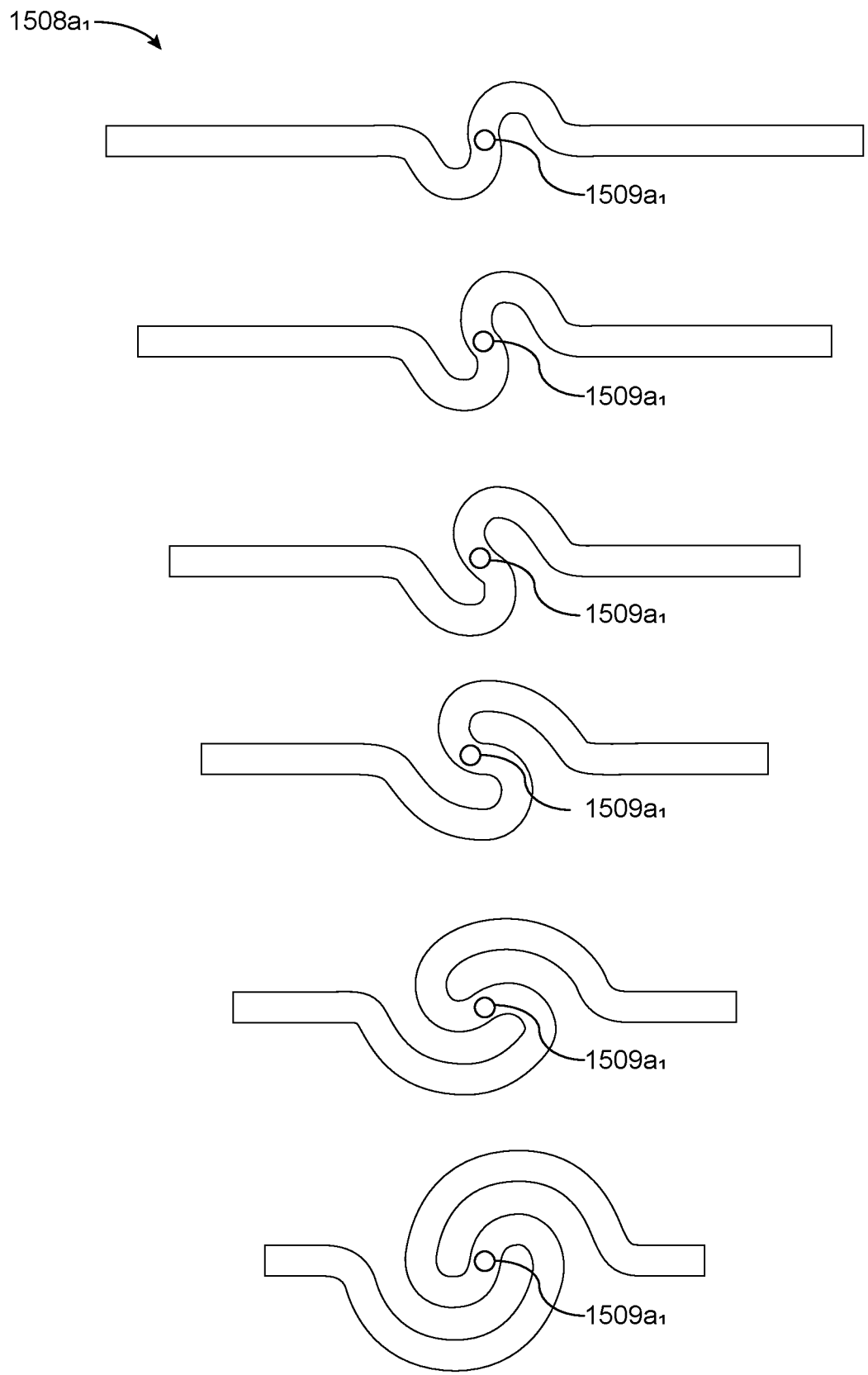

FIG. 15D provides a series of schematic illustrations depicting actuation of the first actuation element 1508$a_1$. In particular, FIG. 15D illustrates the configuration of the first actuation element 1508$a_1$ as it transitions from its tensioned (e.g., stretched) configuration to and/or toward its preferred geometry (e.g., its nontensioned configuration). Because the first actuation element 1508$a_1$ has a torsional shape and is stretched relative to its preferred geometry, transitioning the first actuation element 1508$a_1$ to and/or toward its preferred geometry causes it to decrease in length and rotate or fold about its torsional center point (which can be at or proximate the first target 1509$a_1$). This motion can drive movement of the control element 1502$a$.

The second actuation element 1508$a_2$ can operate in a manner generally similar to the first actuation element 1508$a_1$. However, because the control element 1502$a$ is positioned between the actuation elements 1508, actuation of the first actuation element 1508$a_1$ generally moves the control element 1502$a$ in a first direction, and actuation of the second actuation element 1508$a_2$ generally moves the control element 1502$a$ in a second direction generally opposite the first direction. The second actuator 1501$b$ and the third actuator 1501$c$ can be generally similar to and/or the same as the first actuator 1501$a$. Moreover, although shown has having three actuators 1501, the assembly 1500 can have fewer or more actuators, such as one, two, four, five, six, or more actuators.

Figure 16:
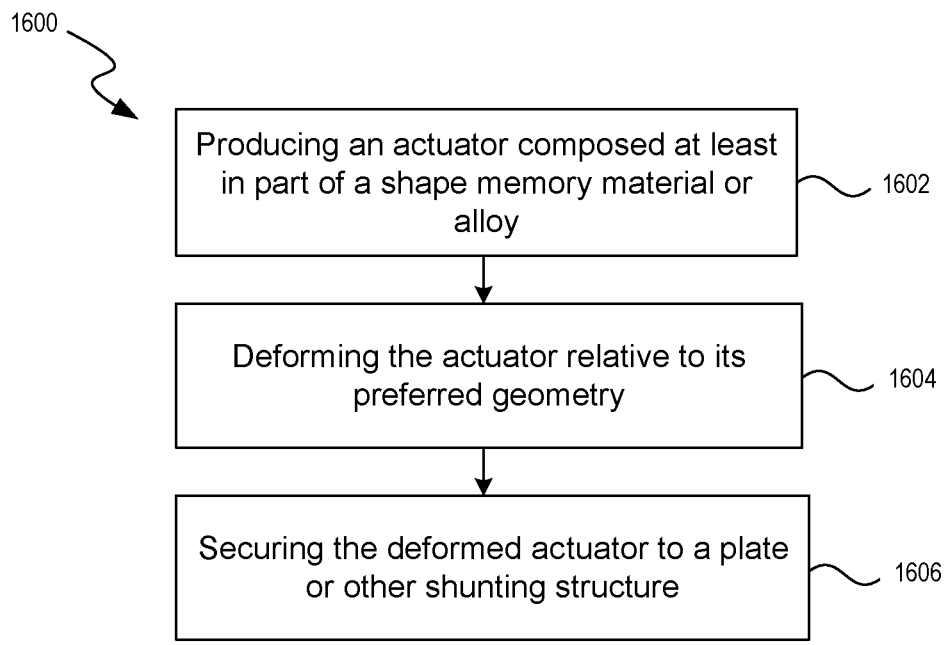
FIG. 16 is a flowchart of a method for manufacturing an adjustable intraocular shunting system in accordance with embodiments of the present technology.

The present technology further provides methods of manufacturing the systems and devices described herein. FIG. 16, for example, is a flowchart of a method 1600 for manufacturing an adjustable intraocular shunting system, such as the systems 700 and 800 described previously. Beginning at step 1602, the method 1600 includes producing (e.g., fabricating) an actuator composed, at least in part, of a shape memory material or alloy. In some embodiments, the actuator is a single or unitary component composed of the shape memory material. The actuator can be produced via a photolithographic process, via a deposition process, via cutting or etching a unitary structure from a sheet or source material, or other suitable techniques. Additional details of producing devices such as actuators via the foregoing techniques are described in U.S. Provisional Patent Application No. 63/039,237, the disclosure of which is incorporated by reference herein in its entirety. The actuator can be any of the actuators described herein, such as those described with respect to FIGS. 2-15D.

The method 1600 can continue at step 1604 by deforming the actuator relative to its fabricated and/or preferred geometry (e.g., to occupy a tensioned configuration) and at step 1606 by securing the deformed actuator to a drainage element, plate, or other shunting structure (e.g., the drainage element 750 or drainage element 850). Deforming the actuator relative to its fabricated geometry can include stretching one or more aspects of the actuator (e.g., the actuation elements 708) relative to their fabricated geometry such that, when the one or more aspects are triggered to move toward their fabricated geometries (e.g., via an induced phase transformation, as previously described), the one or more aspects of the actuator increase in length. Alternatively, deforming the actuator relative to its fabricated geometry can include compressing one or more aspects of the actuator (e.g., the actuation elements 708) relative to their fabricated geometry such that, when the one or more aspects are triggered to move toward their fabricated geometries, the one or more aspects of the actuator decrease in length. In some embodiments, deforming the actuator relative to its preferred geometry includes securing a first portion of the actuator to a second portion of the actuator (e.g., for the actuator 1101 of FIGS. 11A-11D, positioning the anchoring element 1111 on the opposite side of the first and second appendages 1115$a$, 1115$b$ as the projection 1102).

Securing the deformed actuator to the drainage element at step 1606 can include securing the actuator to the drainage element in two or more locations/positions. In some embodiments, the actuator is pivotably/rotatably coupled to the drainage element at least at one of the two or more locations/positions such that a portion of the actuator can pivot or otherwise rotate relative to the drainage element, as previously described. The actuator can be secured to the drainage element via any suitable mechanisms, such as pins, anchors, adhesives, fasteners, or the like. In some embodiments, securing the deformed actuator to the drainage element at step 1606 includes positioning the tensioned actuator in a chamber or other portion of a shunting element or drainage element. After the actuator is secured to the drainage element, the actuator remains at least partially deformed relative to its fabricated geometry so that the actuator can be actuated using its shape memory properties, as described in detail previously.

In some embodiments, steps 1604 and 1606 can be reversed, such that the actuator is secured to the drainage element or other shunting structure and then deformed. In other embodiments, the act of securing the actuator to the drainage element or other shunting structure causes the actuator to deform, and thus steps 1604 and 1606 are performed at substantially the same time.

Figure 17:
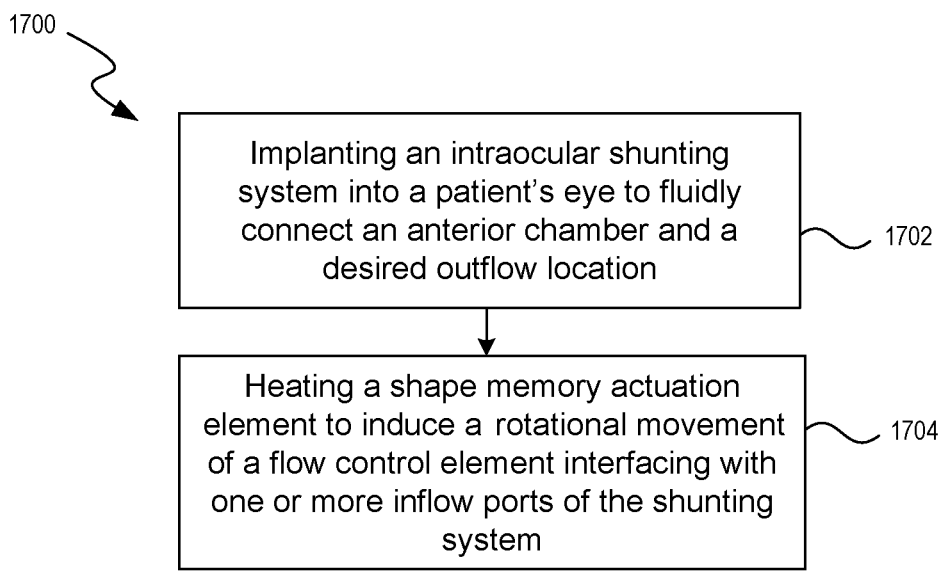
FIG. 17 is a flowchart of a method for treating a patient having glaucoma using an adjustable intraocular shunting system configured in accordance with embodiments of the present technology.

The present technology further provides methods of treating a patient having glaucoma using the intraocular shunting systems described herein. FIG. 17, for example, is a flowchart of a method 1700 of treating a patient having glaucoma. Beginning at step 1702, the method 1700 includes implanting an intraocular shunting system into the patient's eye such that an inflow region of the shunting system (e.g., the first end portion 750a of the drainage element 750) is in fluid communication with an interior of the eye (e.g., the anterior chamber) and an outflow region of the shunting system (e.g., the second end portion 750b of the drainage element 750) is in fluid communication with a desired outflow location, such as a subconjunctival bleb space. Once implanted, the shunting system can fluidly connect the anterior chamber and the desired outflow location and permit aqueous to drain from the anterior chamber to the desired outflow location.

After implanting the shunting system, the method 1700 can continue at step 1704 by heating a shape memory actuation element (e.g., the first actuation element 708a or the second actuation element 708b) to induce a rotational movement of a flow control element (e.g., the projection 702) interfacing with one or more inflow ports at the inflow region. In some embodiments, heating the shape memory actuation element includes heating, via energy applied from an energy source positioned external to the patient's body, the shape memory actuation element above a material transition temperature such that the actuation element changes from a first material state (e.g., a martensitic state, R-phase, etc.) to a second material state (e.g., R-phase, austenitic, etc.). The rotational movement of the flow control element can change a flow resistance through the one or more inflow ports. For example, the rotational movement of the flow control element may further block or unblock the one or more inflow ports, which may permit less or more aqueous from draining via the implanted system.

In some embodiments, heating the shape memory actuation element induces a relatively small geometric change in the actuation element. The relatively small geometric change in the actuation element drives the rotational movement of the flow control element. The rotational movement of a distal end of the flow control element can be a relatively large motion relative to the geometric change in the actuation element. This can be accomplished via an elongated flow control element such as the projection 702 described previously with respect to FIGS. 7A-7E.

The step 1704 can be repeated as many times as necessary to achieve a desired drainage rate and/or to account for changes in a patient's condition. Moreover, the step 1702 and the step 1704 do not necessarily occur at the same time and/or during the patient's same visit to receive therapy. Rather, step 1704 can occur days, months, or even years after the system is implanted in the patient in step 1702. Accordingly, method 1700 enables a healthcare provider to adjust a level of therapy provided by implanted intraocular systems.

As one of skill in the art will appreciate from the disclosure herein, various components of the intraocular shunting systems described above can be omitted without deviating from the scope of the present technology. Likewise, additional components not explicitly described above may be added to the intraocular shunting systems without deviating from the scope of the present technology. Accordingly, the systems described herein are not limited to those configurations expressly identified, but rather encompasses variations and alterations of the described systems.

Conclusion

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, any of the features of the intraocular shunts described herein may be combined with any of the features of the other intraocular shunts described herein and vice versa. Moreover, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions associated with intraocular shunts have not been shown or described in detail to avoid unnecessarily obscuring the description of the embodiments of the technology. Where the context permits, singular or plural terms may also include the plural or singular term, respectively.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An implantable actuator for selectively controlling the flow of fluid through an implantable shunting system, the actuator comprising:

a first actuation element having a first end portion configured to be fixedly coupled to a substrate and a first curved end portion spaced apart from the first end portion by a length of the first actuation element;

a second actuation element having a second end portion configured to be fixedly coupled to the substrate and a second curved end portion spaced apart from the second end portion by a length of the second actuation element; and a rotatable element positioned between and coupled to the first curved end portion and the second curved end portion, wherein the first curved end portion and the second curved end portion are deformable to facilitate rotation of the rotatable element within a plane defined by the actuator.

2. The actuator of claim 1 wherein the rotatable element is a rotatable projection having:

a first portion coupled to the first curved end portion and the second curved end portion, and a second portion extending from the first portion, the second portion configured to have a free end moveable relative to the substrate when the first end portion and the second end portion are coupled to the substrate.

3. The actuator of claim 2 wherein the free end is positioned between the first actuation element and the second actuation element.

4. The actuator of claim 1 wherein the first curved end portion extends orthogonal to an axial length of the first actuation element, and wherein the second curved end portion extends orthogonal to an axial length of the second actuation element.

5. The actuator of claim 1 wherein, when the first end portion of the first actuation element and the second end portion of the second actuation element are fixedly coupled to the substrate:

the first actuation element, upon actuation, is configured to deform at least one of the first curved end portion or the second curved end portion to rotate the rotatable element in a first direction, and the second actuation element, upon actuation, is configured to deform at least one of the first curved end portion or the second curved end portion to rotate the rotatable element in a second direction different than the first direction.

6. The actuator of claim 1 wherein the first actuation element, the second actuation element, and the rotatable element form a single, contiguous component.

7. The actuator of claim 1 wherein the first actuation element and the second actuation element are composed at least in part of a shape memory material.

8. The actuator of claim 1 wherein the substrate includes a surface of the implantable shunting system.

* * * * *